(12) United States Patent
Agamaite et al.

(10) Patent No.: US 9,242,119 B2
(45) Date of Patent: Jan. 26, 2016

(54) ACTIVITY DELIVERY PROGRESS MONITOR

(75) Inventors: James A. Agamaite, Wexford, PA (US);
Scott R. Griffith, Murrysville, PA (US);
Douglas DeScalzi, Pittsburgh, PA (US);
Charles Marsh, Cranberry Township, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 13/700,299

(22) PCT Filed: Jun. 6, 2011

(86) PCT No.: PCT/US2011/039203
§ 371 (c)(1),
(2), (4) Date: Nov. 27, 2012

(87) PCT Pub. No.: WO2011/153519
PCT Pub. Date: Dec. 8, 2011

(65) Prior Publication Data
US 2013/0079581 A1    Mar. 28, 2013

Related U.S. Application Data

(60) Provisional application No. 61/351,480, filed on Jun. 4, 2010.

(51) Int. Cl.
*A61M 3/00* (2006.01)
*A61N 5/10* (2006.01)
(Continued)

(52) U.S. Cl.
CPC .............. *A61N 5/1027* (2013.01); *A61M 5/007* (2013.01); *A61M 5/16831* (2013.01);
(Continued)

(58) Field of Classification Search
CPC ......... A61N 5/00; A61N 5/10; A61N 5/1001; A61N 5/103; A61N 5/1042; A61N 5/1048; A61N 5/1077; A61N 2005/00; A61N 2005/10; A61N 2005/1001; A61N 2005/103; A61N 2005/1048; A61N 2005/1085; A61N 2005/1092; A61K 9/0004; A61K 9/0024; A61K 51/0455; A61B 5/417; A61M 5/1782; A61M 5/1785; G06F 19/3468
USPC ....... 600/1–5; 128/897–899; 137/1; 220/501; 604/19
See application file for complete search history.

(56) References Cited

U.S. PATENT DOCUMENTS 6,162,198 A * 12/2000 Coffey et al. ................. 604/198
6,602,488 B1 * 8/2003 Daghighian ................... 424/9.3
(Continued)

FOREIGN PATENT DOCUMENTS

| EP | 0117752 | | 9/1984 |
|---|---|---|---|
| WO | 2006007750 | | 1/2006 |
| WO | 2008083313 | A2 | 7/2008 |
| WO | 2009042577 | A2 | 4/2009 |

*Primary Examiner* — Navin Natnithithadha
*Assistant Examiner* — Sunita Reddy
(74) *Attorney, Agent, or Firm* — Joseph L. Kent; David Schramm

(57) ABSTRACT

A system and method for monitoring progress of a radiopharmaceutical injection procedure includes: measuring and monitoring radiopharmaceutical activity of a radiopharmaceutical remaining in at least a portion of a disposable administration set used with a radiopharmaceutical fluid delivery system; and displaying the radiopharmaceutical activity remaining in at least the portion of the disposable administration set to an operator.

22 Claims, 33 Drawing Sheets

(51) Int. Cl.
*A61M 5/00* (2006.01)
*A61M 5/168* (2006.01)
*G06F 19/00* (2011.01)
*G21G 1/00* (2006.01)
*A61B 6/03* (2006.01)
*A61M 5/142* (2006.01)

(52) U.S. Cl.
CPC ........... *A61N 5/1064* (2013.01); *A61N 5/1071* (2013.01); *A61B 6/037* (2013.01); *A61M 5/14212* (2013.01); *A61M 2005/16863* (2013.01); *A61M 2205/3327* (2013.01); *G06F 19/3468* (2013.01); *G21G 1/0005* (2013.01)

(56) References Cited

U.S. PATENT DOCUMENTS

| | | | |
|---|---|---|---|
| 2004/0082918 A1* | 4/2004 | Evans et al. | 604/207 |
| 2004/0205343 A1* | 10/2004 | Forth et al. | 713/168 |
| 2005/0129170 A1 | 6/2005 | Watson et al. | |
| 2008/0131362 A1 | 6/2008 | Rousso et al. | |
| 2008/0177126 A1* | 7/2008 | Tate et al. | 600/5 |
| 2009/0257949 A1 | 10/2009 | Hefti et al. | |
| 2010/0185040 A1* | 7/2010 | Uber et al. | 600/5 |
| 2011/0076317 A1 | 3/2011 | Alessi et al. | |
| 2012/0074330 A1* | 3/2012 | Bouton et al. | 250/393 |
| 2013/0123567 A1* | 5/2013 | Agamaite et al. | 600/4 |

* cited by examiner

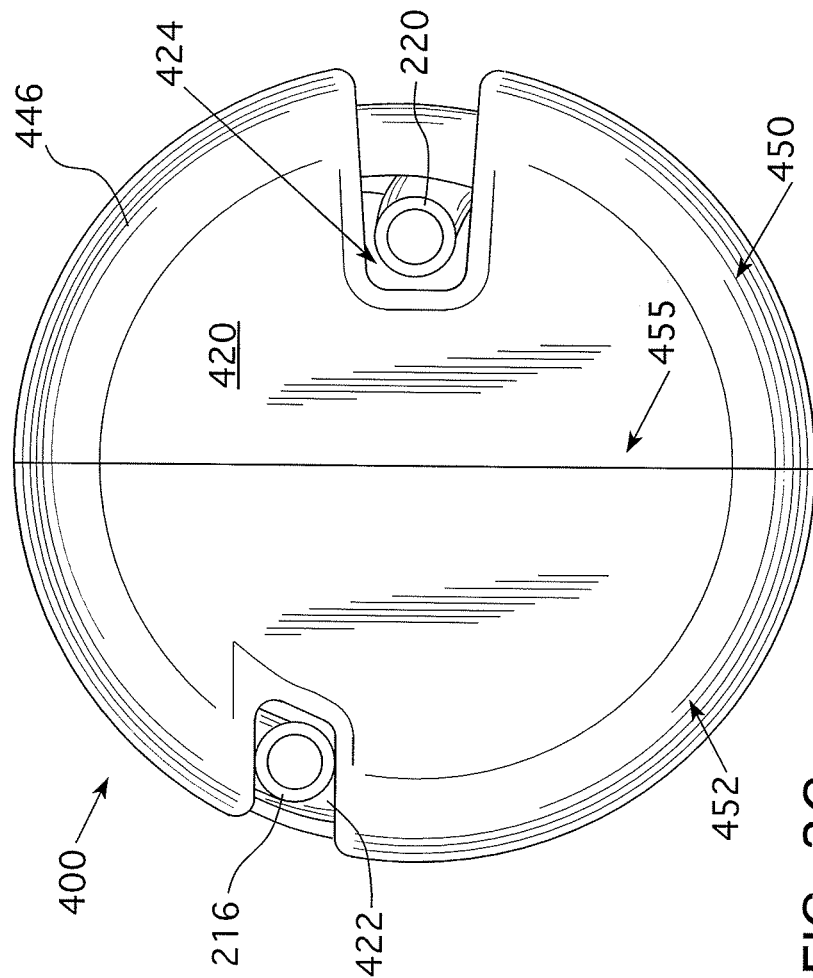
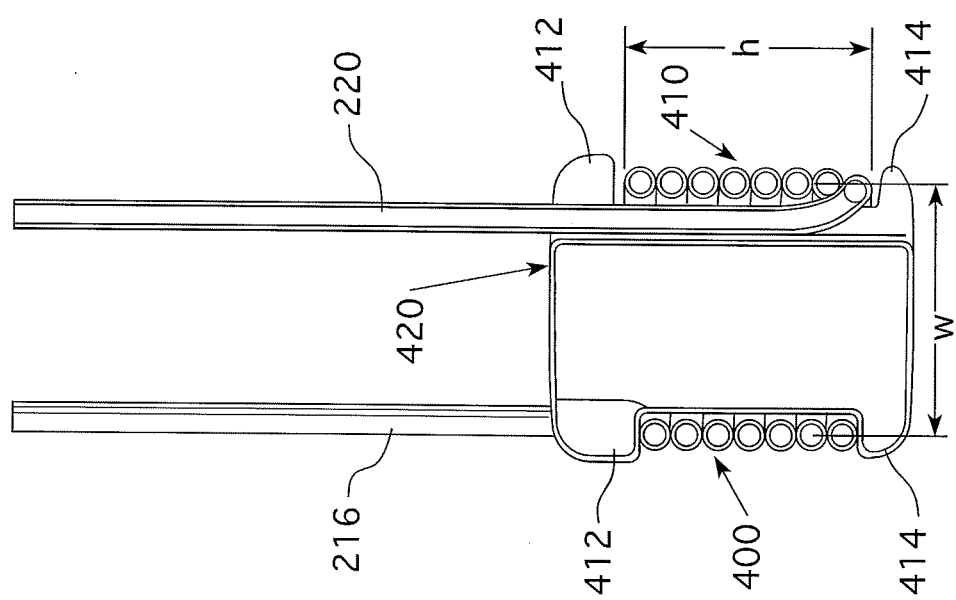
FIG. 3C
FIG. 3B

FIG. 23

- 1240d: 27 March 2010 10:48
- 1245: Dose Discarded / Partial dose delivered to patient
- 1244: Print
- Case ID: 3N
- FDG Lot #: 11
- IV Site: Left Antecubital
- FDG Delivered: 524.0 MBq
- FDG Discarded: 54.0 MBq
- Total Fluid Delivered: 35.7 ml
- 1252: Next Patient
- 1250: Retry Patient

ACTIVITY DELIVERY PROGRESS MONITOR

CLAIM OF PRIORITY

Cross Reference to Related Application

This application is a 371 national phase application of PCT International Application No. PCT/US2011/039203, filed on Jun. 6, 2011, and designating the United States of America, which claims the benefit of U.S. Provisional Application Ser. No. 61/351,480, filed on Jun. 4, 2010, the contents of which are incorporated herein by reference.

BACKGROUND

1. Technical Field

This disclosure relates to the administration of pharmaceutical substances, typically intrinsically harmful or toxic pharmaceutical substances such as radioactive pharmaceutical substances, generally known as radiopharmaceuticals, to human and animal subjects and, more specifically, to a method of and a system for measuring the activity of a radiopharmaceutical during an injection procedure.

2. Description of Related Art

Administration of radioactive pharmaceutical substances or drugs, generally termed radiopharmaceuticals, is often used in the medical field to provide information or imagery of internal body structures and/or functions including, but not limited to, bone, vasculature, organs and organ systems, and other tissue. Additionally, such radiopharmaceuticals may be used as therapeutic agents to kill or inhibit the growth of targeted cells or tissue, such as cancer cells.

Two types of imaging procedures utilizing radiopharmaceuticals are positron emission tomography (PET) or single-photon emission computerized tomography (SPECT) procedures. PET and SPECT are noninvasive, three-dimensional, imaging procedures that provide information regarding physiological and biochemical processes in patients. PET and SPECT images of, for example, the brain or another organ, are produced by injecting the patient with a dose of a radiopharmaceutical and then creating an image based on the radiation emitted by the radiopharmaceutical. The radiopharmaceutical generally includes a radioactive substance, such as a radioisotope, that can be absorbed by certain cells in the brain or other organs, concentrating it there.

Radioisotopes, especially those with short half-lives, can be relatively safely administered to patients in the form of a labeled substrate, ligand, drug, antibody, neurotransmitter, or other compound or molecule that is normally processed or used by the body (for example, glucose). The radioisotope acts as a tracer of specific physiological or biological processes. For example, fluorodeoxyglucose (FDG) is a normal molecule of glucose, the basic energy fuel of cells, to which is attached a radioisotope or radioactive fluorine (i.e., $^{18}$F). The $^{18}$F radioisotope is produced in a cyclotron equipped with a unit to synthesize the FDG molecule.

Cells (for example, in the brain) that are more active in a given period of time after an injection of FDG will absorb more FDG because they have a higher metabolism and require more energy. The $^{18}$F radioisotope in the FDG molecule experiences a radioactive decay, emitting a positron. When a positron collides with an electron, annihilation occurs, liberating a burst of energy in the form of two beams of gamma rays in opposite directions. The PET scanner detects the emitted gamma rays to compile a three dimensional image.

To allow for cell uptake of the radiopharmaceutical, the patient typically rests for a period of time (45-90 minutes for FDG) after the radiopharmaceutical is injected. After sufficient time for cell uptake has elapsed, the patient is typically placed on a movable bed that slides into the PET (or SPECT), or other suitable scanner. The PET scanner includes several rings of radiation detectors. Each detector emits a brief pulse of light every time it is struck with a gamma ray coming from the radioisotope within the patient's body. The pulse of light is amplified by, for example, a photomultiplier, and the information is sent to the computer for forming images of the patient.

To minimize the radiation dose to patients, radiopharmaceuticals containing radioisotopes, such as Flourine-18, Technetium-99, Carbon-11, Copper-64, Gallium-67, Iodine-123, Nitrogen-13, Oxygen-15, Rubidium-82, Thallium-201, Chromium-51, Iodine-131, Iodine-151, Iridium-192, Phosphorus-32, Samarium-153, and Yttrium-90, having relatively short half-lives are typically used for PET and SPECT imaging procedures and other radio-therapies. $^{18}$F, for example, has a half-life of 109.7 minutes.

Because of its short half-life, the radioactivity level of the radioisotope will quickly decrease after it is manufactured in a cyclotron or a reactor. Consequently, the elapsed time (and corresponding decrease in radioactivity level of the radioisotope) after synthesis of the radiopharmaceutical must be factored into calculating the volume of radiopharmaceutical required to be injected into the patient to deliver the desired radioactivity dose. If the time delay after synthesis is long in relation to the radioisotope's half-life or if the calculated volume of radiopharmaceutical to be injected into the patient is insufficient to deliver the desired radioactivity dose, the delivered radioactivity dose may be too low to provide diagnostic-quality images, resulting in wasted time and effort and exposing the patient and medical personnel to unnecessary radiation.

In addition, radiopharmaceutical agents used in imaging procedures and therapeutic procedures are hazardous to attending medical personnel. These agents are toxic and can have physical and/or chemical effects for attending medical personnel such as clinicians, imaging technicians, nurses, and pharmacists. Excessive radiation exposure is harmful to attending medical personnel due to their occupational repeated exposure to the radiopharmaceuticals. However, due to the short half-life of typical radiopharmaceutical agents and small applied dosages, the radiation exposure risk-to-benefit ratio for individual patients is acceptable. The constant and repeated exposure of medical personnel to radiopharmaceuticals over an extended period of time is a significant problem in the nuclear medicine field.

With the foregoing background in place, exemplary current practice of generating, preparing, and administration of radiopharmaceuticals will now be described. Typical radiopharmaceutical treatment practice in the United States includes having the radiopharmaceutical agent initially generated off-site from a treatment location, typically a hospital, by an outside nuclear medicine facility and then delivered to the treatment location for further preparation, for example, individual dosing and administration. The treatment location, for example, a hospital, orders specific radioactive substances to be ready at specific times for specific patients. These substances are prepared by the outside nuclear medicine facility and with sufficient radioactivity that they will have the desired radioactivity level at the targeted time. For example, the outside nuclear medicine provider may have a facility equipped with a cyclotron or radioisotope generator in, for example, a lead-shielded enclosure wherein the radiopharmaceutical agent, namely, a radioactive isotope is generated or created. Further refining or dose preparation steps, namely, placing the radioisotope in injectable form, may occur at the off-treatment site. Thus, the outside provider may provide a radiopharmaceutical substance to the treatment site having a desired radioactivity level at the targeted time. Further "individual" dose preparation of the radiopharmaceutical agent may occur at the treatment site. Alternatively, the outside provider may provide a "finished" radiopharmaceutical agent ready for injection to a specified patient at a specified time so that treatment site personnel are only required to confirm that the correct radioactive dosage is present in the radiopharmaceutical agent, for example, in a stand-alone radiation dosimetry device as described previously. During the forgoing process, there is frequent close-proximity contact with radioactive materials by personnel and, as described previously, handling and transport shielding devices are needed for the protection of these personnel.

Transport pigs are commonly employed to transport the radiopharmaceutical agents, which are individual doses prepared for individual patients, to the treatment facility. At the treatment facility, data about each unit dose is entered into a facility computer either manually or through reading a bar code, floppy disk, or other similar data format, which may accompany or be on the transport pig or the radiopharmaceutical agent container. When it is time to deliver a specified unit dose to a specified patient, treatment facility personnel must remove, for example, a syringe containing the radiopharmaceutical agent from the transport pig and confirm that the dose in the syringe is within the range prescribed for that patient. Alternatively, the attending personnel must transfer the radiopharmaceutical agent to a shielded syringe as identified previously and confirm dosage. If the dose is too high, some is discarded into a shielded waste container. If the dose is too low, either a different syringe is used and/or additional agent is loaded into the syringe if available. While it is possible for the attending treatment site personnel to be involved with dosage preparation, typical United States practice is to have the radiopharmaceutical agent delivered to the treatment site which will have the desired radioactivity level at the targeted time. Manual manipulation of the radiopharmaceutical agent at the treatment site is limited at the treatment site due to this procedure. Nonetheless, various manual checks are required to confirm that a correct radiopharmaceutical dose is ready for injection into a specific patient. These manual checks include visual inspections and radioactivity measurements as noted above.

As an example of the foregoing, in PET imaging, an injectable radiopharmaceutical agent such as, for instance, FDG (fluorodeoxyglucose) is fabricated in a cyclotron device at an outside nuclear medicine facility. Thereafter, the FDG is processed to be in a radiopharmaceutical form and is transferred in an individual dose container (i.e., vial, bottle, syringe, etc.) and the container is loaded into a transport pig to prevent unnecessary radiation exposure to personnel, such as the radio-pharmacist, technician, and driver responsible for creation, handling, and transport of the FDG from the cyclotron site to the PET imaging site. Since the half-life of FDG is short, approximately 110 minutes, it is necessary to quickly transport the FDG to the PET imaging site. Depending upon the elapsed transport time and the initial radioactivity level of the FDG at the time of fabrication, the radioactivity level of the FDG may need to be re-measured at the PET imaging site. As an example, if the radioactivity level is too high, the transport radio-pharmacist or a radio-pharmacist at the PET imaging site may be required to dilute the FDG with a diluent diluent such as, for instance, saline solution, and remove part of the volume or extract fluid to reduce radioactivity prior to patient injection. During this entire process, the handling of FDG from creation to patient injection may be entirely manual. Within this process, shielding products, as described previously (i.e., transport pigs, syringe shields, L-blocks, etc.) are used to shield individuals from FDG. While shielding may reduce the radiation exposure of the radio-pharmacist, the radio-pharmacist may still be exposed to emissions from the radiopharmaceutical agent during the manual mixing, volume reduction, and/or dilution process needed to obtain the required dose. After injection and often after an additional delay to allow the radiopharmaceutical to reach and be absorbed by the desired regions of interest in the body, the patient is typically placed on a moveable bed that slides by remote control into a circular opening of an imaging scanner referred to as the gantry. Positioned around the circular opening and inside the gantry are several rings of radiation detectors. In one type of radiation detector, each detector emits a brief pulse of light every time it is struck with a gamma ray coming from the radionuclide within the patient's body. The pulse of light is amplified by a photomultiplier converted to an electronic signal and the information is sent to the computer that controls the apparatus and records imaging data.

For the sake of completeness, it should be noted that in the United States it also known to have radiopharmaceutical agents delivered in a multi-dose format to the treatment site. As a result, this multi-dose format must be divided into singular doses for individual patients at the treatment site.

The current systems described hereinabove, however, do not provide a system for automatically and continuously monitoring the radioactivity of a radiopharmaceutical within a disposable administration set of a radiopharmaceutical, detect a delivery issue based on the monitored radioactivity of a radiopharmaceutical, and adjust the fluid delivery of the system to cure the delivery issue.

SUMMARY

Therefore, it is an object of the present disclosure to provide a method and system that overcome some or all of the drawbacks and deficiencies evident in the prior art. More specifically, the systems and methods of the present disclosure provide automatic and continuous monitoring of the radioactivity of a radiopharmaceutical within a disposable administration set of a radiopharmaceutical, detection of a delivery issue based on the monitored radioactivity of a radiopharmaceutical, and adjustment of the fluid delivery of the system to cure the delivery issue. Such a system provides early indication of delivery issues, such as an occluded administration set, allowing the operator to have early intervention to cure the delivery issue.

Accordingly, provided is a method for monitoring progress of a radiopharmaceutical injection procedure. The method includes measuring and monitoring radiopharmaceutical activity of a radiopharmaceutical remaining in at least a portion of a disposable administration set used with a radiopharmaceutical fluid delivery system; and displaying the radiopharmaceutical activity remaining in at least the portion of the disposable administration set to an operator.

The method may further include alerting the operator of a delivery issue when the radiopharmaceutical activity remaining in at least a portion of the disposable administration set differs from a known value of radiopharmaceutical activity remaining in at least a portion of the disposable administration set at a given time. The delivery issue may be a full or partial occlusion in the disposable administration set. The method may also include: automatically adjusting at least one of saline volume and saline flow rate to the disposable administration set to flush the radiopharmaceutical remaining in at least a portion of the disposable administration set if the delivery issue occurs; and ending the radiopharmaceutical injection procedure if the step of automatically adjusting at least one of saline volume and saline flow rate fails to cure the delivery issue.

The step of displaying the radiopharmaceutical activity remaining in at least the portion of the disposable administration set to an operator may include displaying a representation of the radiopharmaceutical activity remaining in at least the portion of the disposable administration set on a display device of the radiopharmaceutical fluid delivery system. The representation of the radiopharmaceutical activity remaining in at least the portion of the disposable administration set may be a numeric display, a bar graph, an x-y plot, or a scatter plot. The measured radiopharmaceutical activity of the radiopharmaceutical remaining in at least a portion of a disposable administration set may be the measured activity as a function of time, flow rate, and/or volume.

The measuring and monitoring of the radiopharmaceutical activity of a radiopharmaceutical remaining in at least a portion of a disposable administration set may be performed by an ionization chamber, a CZT crystal detector, a Geiger-Müller counter, or a scintillating counter. The radiopharmaceutical fluid delivery device may include: the disposable administration set for allowing fluid flow from a radiopharmaceutical source of the radiopharmaceutical fluid delivery device to a patient; an activity measuring unit operable to determine a level of radioactivity within at least a portion of the disposable administration set; a control unit operatively coupled to the activity measuring unit for converting activity measurements taken by the activity measuring unit to a representation of the radiopharmaceutical activity remaining in at least the portion of the disposable administration set; and a display unit operatively coupled to the control unit for displaying the radiopharmaceutical activity remaining in at least the portion of the disposable administration set to an operator.

The disposable administration set may be a multi-patient disposable administration set, and may include a medical fluid component; a radiopharmaceutical component; a coil component coupled to the medical fluid component and the radiopharmaceutical component; and a waste component coupled to the medical fluid component, the coil component, and the radiopharmaceutical component. The coil component may be the portion of the disposable administration set that is configured to have the radiopharmaceutical activity of the radiopharmaceutical remaining therein measured and monitored.

Further provided is an article that includes a machine-readable storage medium containing instructions that, if executed, enable a processor to: measure and monitor radiopharmaceutical activity of a radiopharmaceutical remaining in at least a portion of a disposable administration set used with a radiopharmaceutical fluid delivery system; and display the radiopharmaceutical activity remaining in at least the portion of the disposable administration set to an operator.

The machine-readable storage medium may further contain instructions that, if executed, enable a processor to alert the operator of a delivery issue when the radiopharmaceutical activity remaining in at least a portion of the disposable administration set differs from a known value of radiopharmaceutical activity remaining in at least a portion of the disposable administration set at a given time. The delivery issue may be a full or partial occlusion in the disposable administration set. The machine-readable storage medium may also contain instructions that, if executed, enable a processor to: automatically adjust at least one of saline volume and saline flow rate to the disposable administration set to flush the radiopharmaceutical remaining in at least a portion of the disposable administration set if the delivery issue occurs; and end the radiopharmaceutical injection procedure if the step of automatically adjusting at least one of saline volume and saline flow rate fails to cure the delivery issue.

In addition, provided is a progress monitoring software stored on a storage medium to monitor progress of a radiopharmaceutical injection procedure. The software includes programming instructions that, if executed, enable a processor to: measure and monitor radiopharmaceutical activity of a radiopharmaceutical remaining in at least a portion of a disposable administration set used with a radiopharmaceutical fluid delivery system; and display the radiopharmaceutical activity remaining in at least the portion of the disposable administration set to an operator.

The storage medium may include further programming instructions that, if executed, enable a processor to alert the operator of a delivery issue when the radiopharmaceutical activity remaining in at least a portion of the disposable administration set differs from a known value of radiopharmaceutical activity remaining in at least a portion of the disposable administration set at a given time. The delivery issue may be a full or partial occlusion in the disposable administration set. The storage medium may also include programming instructions that, if executed, enable a processor to: automatically adjust at least one of saline volume and saline flow rate to the disposable administration set to flush the radiopharmaceutical remaining in at least a portion of the disposable administration set if the delivery issue occurs; and end the radiopharmaceutical injection procedure if the step of automatically adjusting at least one of saline volume and saline flow rate fails to cure the delivery issue.

Further provided is a radiopharmaceutical fluid delivery device for performing a radiopharmaceutical injection procedure that includes: a disposable administration set for allowing fluid flow from a radiopharmaceutical source of the radiopharmaceutical fluid delivery device to a patient; an activity measuring unit operable to determine a level of radioactivity within at least a portion of the disposable administration set; a control unit operatively coupled to the activity measuring unit for converting activity measurements taken by the activity measuring unit to a representation of the radiopharmaceutical activity remaining in at least the portion of the disposable administration set; and a display unit operatively coupled to the control unit for displaying the radiopharmaceutical activity remaining in at least the portion of the disposable administration set to an operator during an injection procedure.

The operator may be alerted of a delivery issue when the radiopharmaceutical activity remaining in at least a portion of the disposable administration set differs from a known value of radiopharmaceutical activity remaining in at least a portion of the disposable administration set at a given time. The delivery issue may be an occlusion in the disposable administration set. At least one of saline volume and saline flow rate to the disposable administration set may be adjusted to flush the radiopharmaceutical remaining in at least a portion of the disposable administration set if the delivery issue occurs. The radiopharmaceutical injection procedure may be ended if the step of adjusting at least one of saline volume and saline flow rate fails to cure the delivery issue.

The activity measuring unit may be one of an ionization chamber, a CZT crystal detector, a Geiger-Müller counter, and a scintillating counter. The display unit may display a representation of the radiopharmaceutical activity remaining in at least the portion of the disposable administration set on a display device of the radiopharmaceutical fluid delivery system. The representation of the radiopharmaceutical activity remaining in at least the portion of the disposable administration set may be at least one of a numeric display, a bar graph, an x-y plot, and a scatter plot.

The disposable administration set may be a multipatient disposable administration set. The disposable administration set may include: a medical fluid component; a radiopharmaceutical component; a coil component coupled to the medical fluid component and the radiopharmaceutical component; and a waste component coupled to the medical fluid component, the coil component, and the radiopharmaceutical component. The coil component may be the portion of the disposable administration set that is configured to have the radiopharmaceutical activity of the radiopharmaceutical remaining therein measured and monitored.

Also provided is a method of determining a flow rate of a fluid in an injection system. The method includes: pumping a radiopharmaceutical from an ionization chamber by adding saline to the ionization chamber; continuously monitoring the radioactivity of the fluid in the ionization chamber to determine a plurality of measured activity values; calculating a slope of radioactive emissions based on the plurality of measured activity values to determine an emissions slope; and calculating a rate at which the radiopharmaceutical is replaced by the saline based on the emissions slope and the volume of the chamber. The rate at which the marked fluid is replaced by the additional fluid corresponds to a flow rate of the fluid.

Further provided is a method of determining a flow rate of a radiopharmaceutical fluid in an injection system during an injection procedure. The method includes: measuring and monitoring radiopharmaceutical activity of the radiopharmaceutical fluid remaining in at least a portion of a disposable administration set used with a radiopharmaceutical fluid delivery system to determine a plurality of radiopharmaceutical activity values during the injection procedure; and determining a flow rate the radiopharmaceutical fluid passing through the disposable administration set.

The flow rate of the radiopharmaceutical fluid passing through the disposable administration set may be determined using a linear regression model. The method may further include the steps of: determining a location of the radiopharmaceutical volume within the disposable administration set based on the flow rate of the radiopharmaceutical fluid passing through the disposable administration set; and automatically adjusting parameters of the injection procedure based on the location of the radiopharmaceutical fluid within the disposable administration set. The measuring and monitoring of the radiopharmaceutical activity of a radiopharmaceutical remaining in at least a portion of a disposable administration set may be performed by one of an ionization chamber, a CZT crystal detector, a Geiger-Müller counter, and a scintillating counter.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended to limit the scope of this disclosure. As used in the specification and the claims, the singular form of "a", "an", and "the" include plural referents unless the context clearly dictates otherwise.

BRIEF DESCRIPTION OF THE DRAWINGS

FIG. 3B is a partial cross-sectional view of FIG. 3A;

FIG. 3C is a plan view (in partial cross-section) taken along line 3C-3C of FIG. 3A;

FIGS. 12-23 are various depictions of a graphical operator interface for use in injection procedures according to an embodiment;

DETAILED DESCRIPTION

Figure 1A:
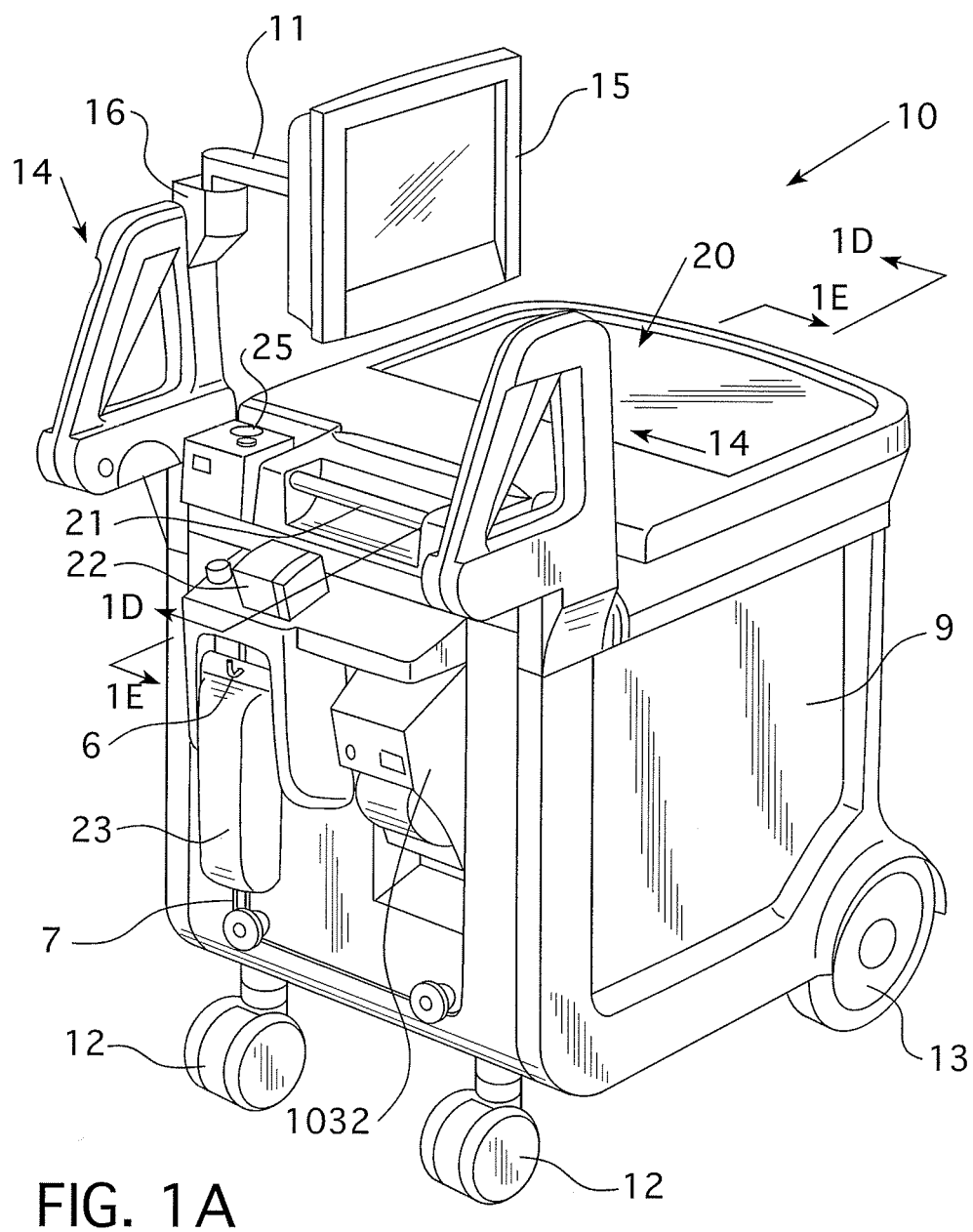
FIG. 1A is a perspective view of a fluid delivery system according to an embodiment.

For purposes of the description hereinafter, the terms "upper", "lower", "right", "left", "vertical", "horizontal", "top", "bottom", "lateral", "longitudinal", and derivatives thereof shall relate to the orientation of embodiments disclosed in the drawing figures. However, it is to be understood that embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

It is to be understood that the disclosed embodiments may assume various alternative variations and step sequences, except where expressly specified to the contrary. It is also to be understood that the specific devices and processes illustrated in the attached drawings, and described in the following specification, are simply exemplary embodiments.

An exemplary radiopharmaceutical fluid delivery system for use with the system disclosed herein is disclosed in United States Patent Application Publication No. 2008/0177126 to Tate et al., the disclosure of which is incorporated herein by reference. More specifically, FIGS. 1A-1F show an exemplary embodiment of such a radiopharmaceutical fluid delivery system 10. The fluid delivery system 10 may be configured as a cart-like apparatus 9 having wheels 13 and/or casters 12 for allowing the system to be movable. One or more of the wheels 13 may be lockable to prevent the system 10 from moving once it is in position. The system 10 also preferably includes one or more handles 14 for allowing an operator to move or position the system 10. Alternately, the fluid delivery system 10 may be a stand-alone or fixed-position apparatus.

The fluid delivery system 10 includes a display or graphical user interface (GUI) 15 for programming and operating the system 10. The GUI display 15 may be attached to one of the handles 14 (as shown) of the system 10. The display 15 may be a color display and incorporate touch-screen capability, as known in the art, for ease of use. The display 15 may be fixed, but is preferably pivotally connected to the fluid delivery system 10 (as shown), by means of a movable arm 11 that is pivotally connected to a joint 16. Further, the display 15 may be tilted or swiveled with respect to the arm 11 to allow for optimal positioning of the display 15 by an operator.

Figure 1B:
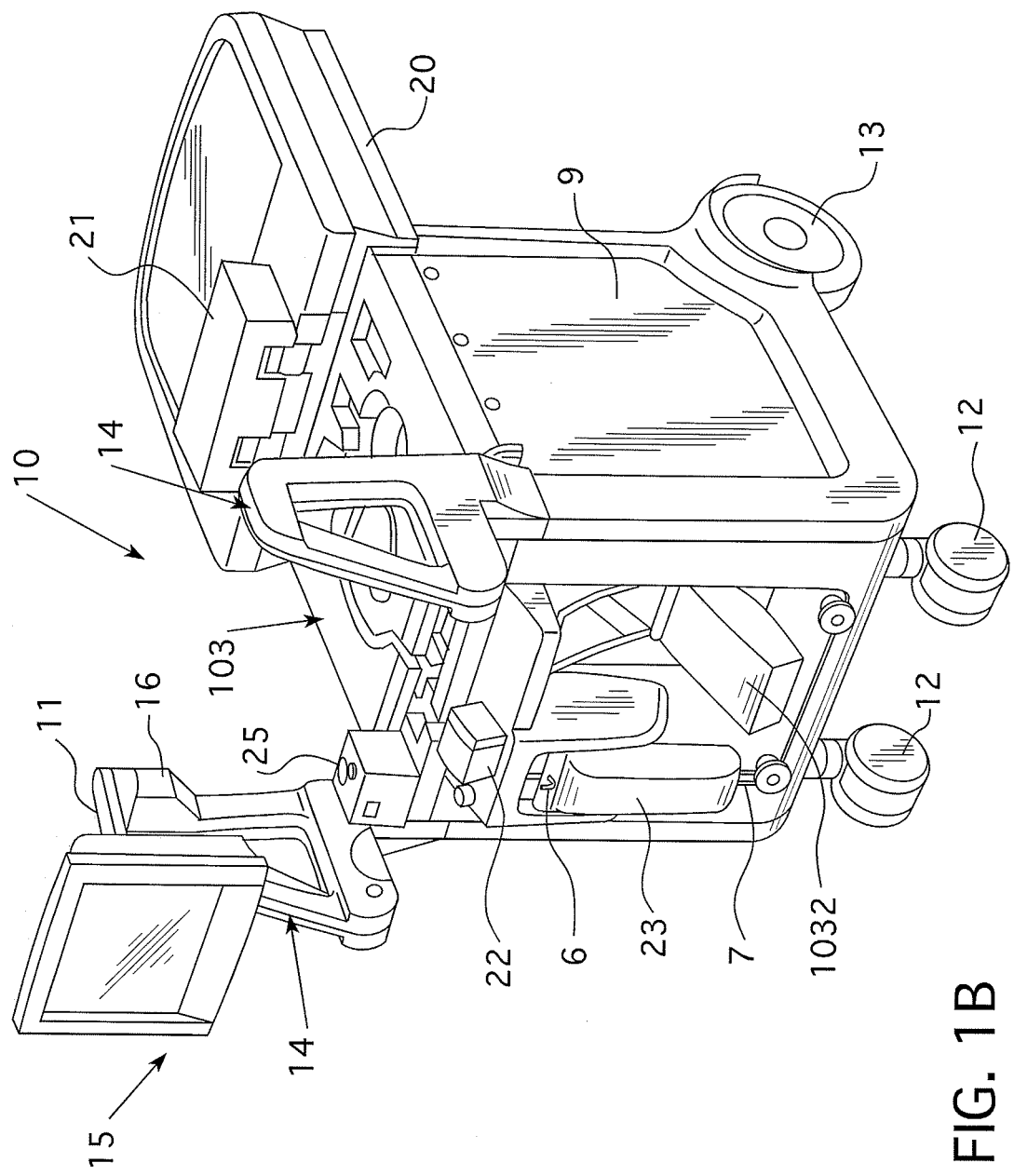
FIG. 1B is another perspective view of the fluid delivery system of FIG. 1A with the shielded cover thereof in a retracted position.
Figure 1C:
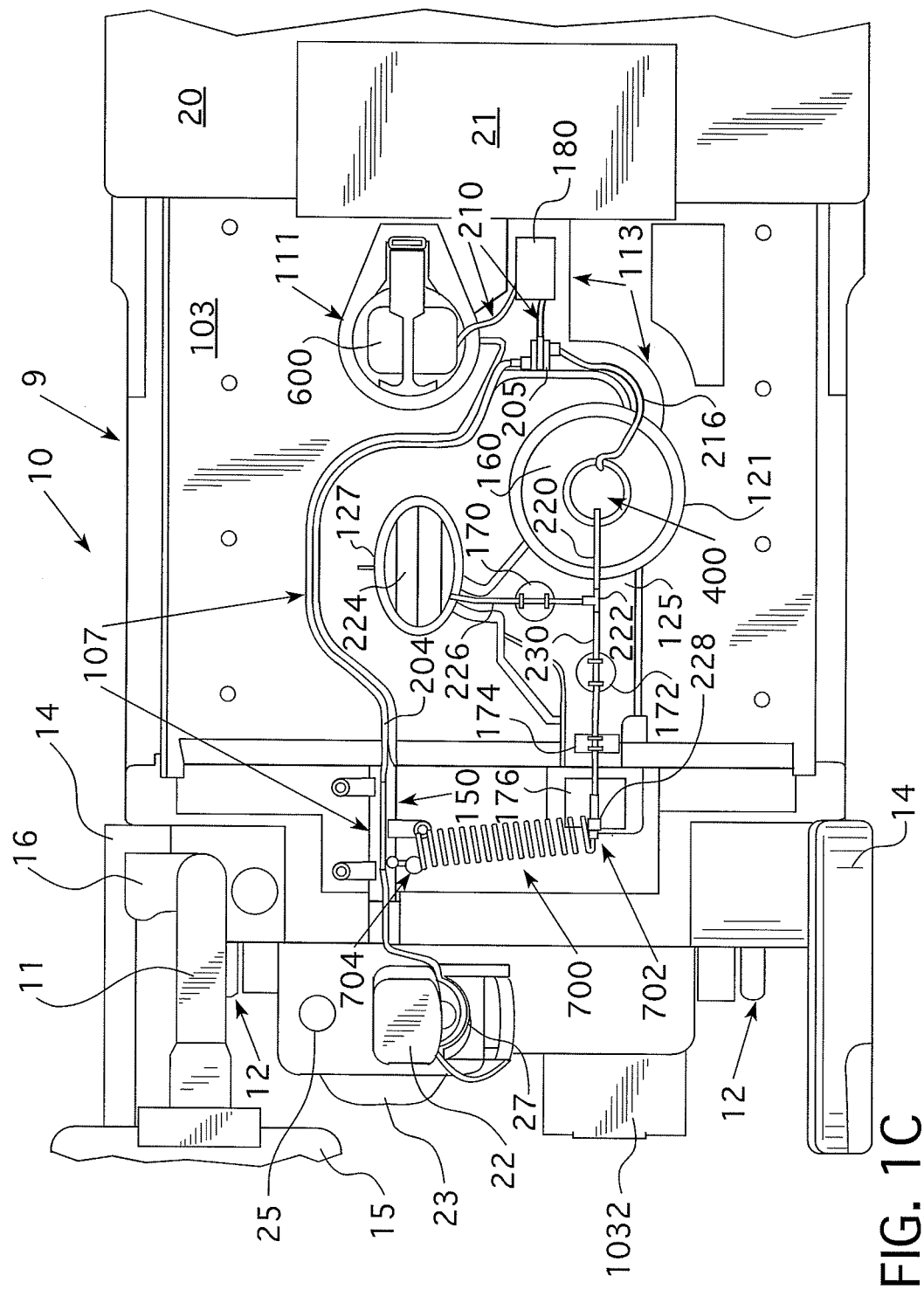
FIG. 1C is a top plan view of the fluid delivery system shown in FIGS. 1A and 1B with various fluid path components positioned therein.
Figure 1D:
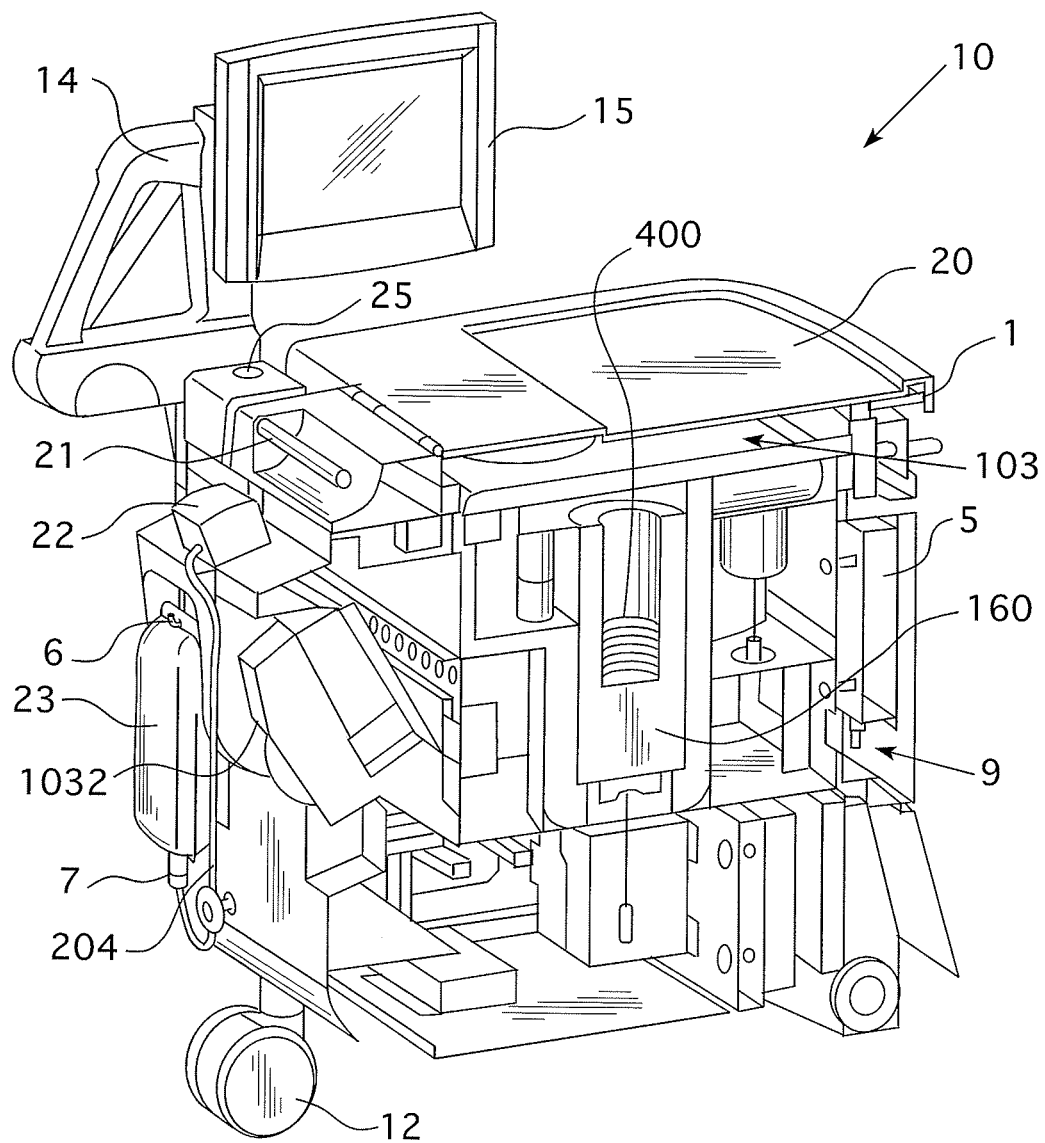
FIG. 1D is a cross-sectional view taken along line 1D-1D of FIG. 1A.
Figure 1E:
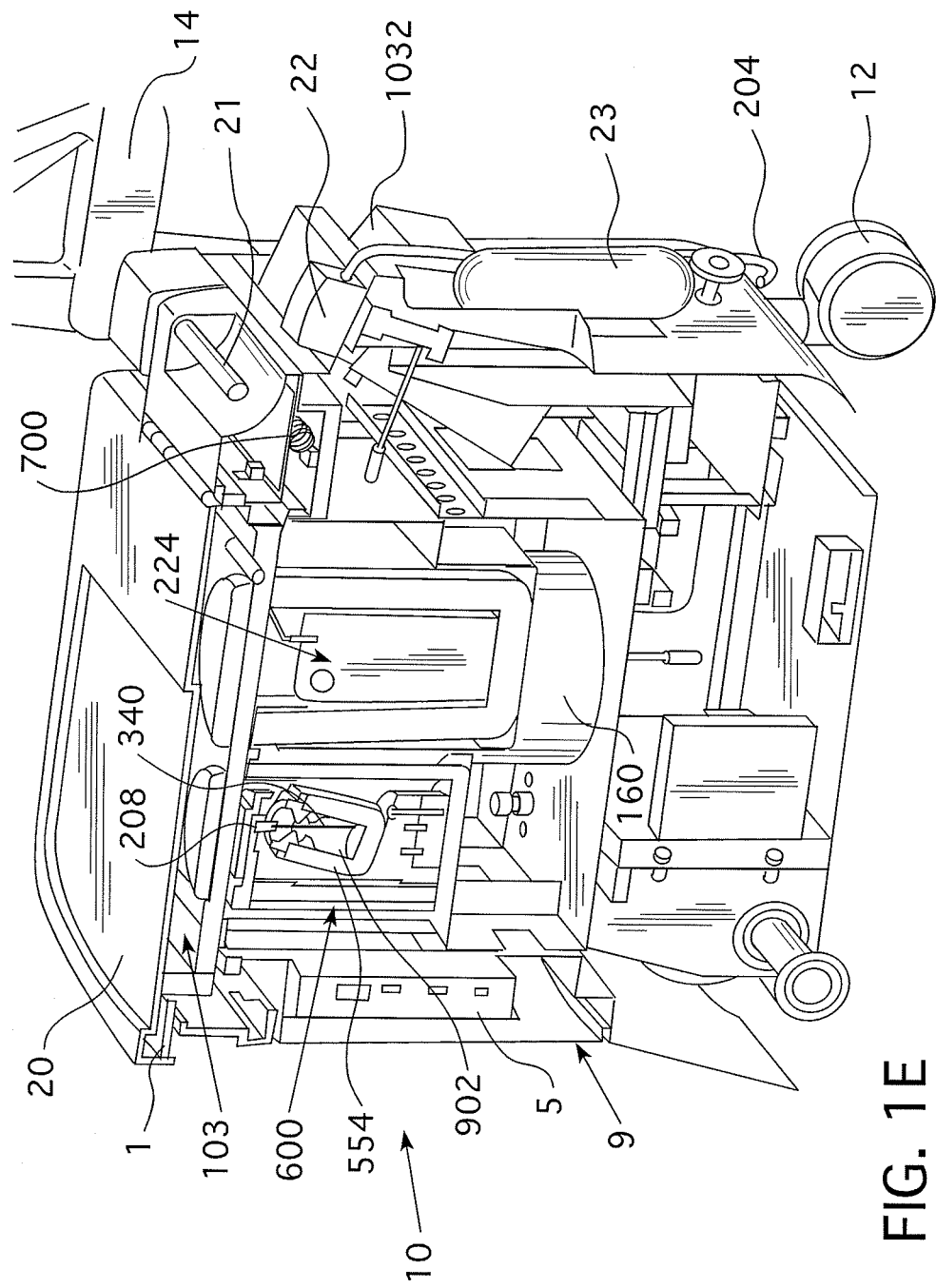
FIG. 1E is a cross-sectional view taken along line 1E-1E of FIG. 1A.
Figure 1F:
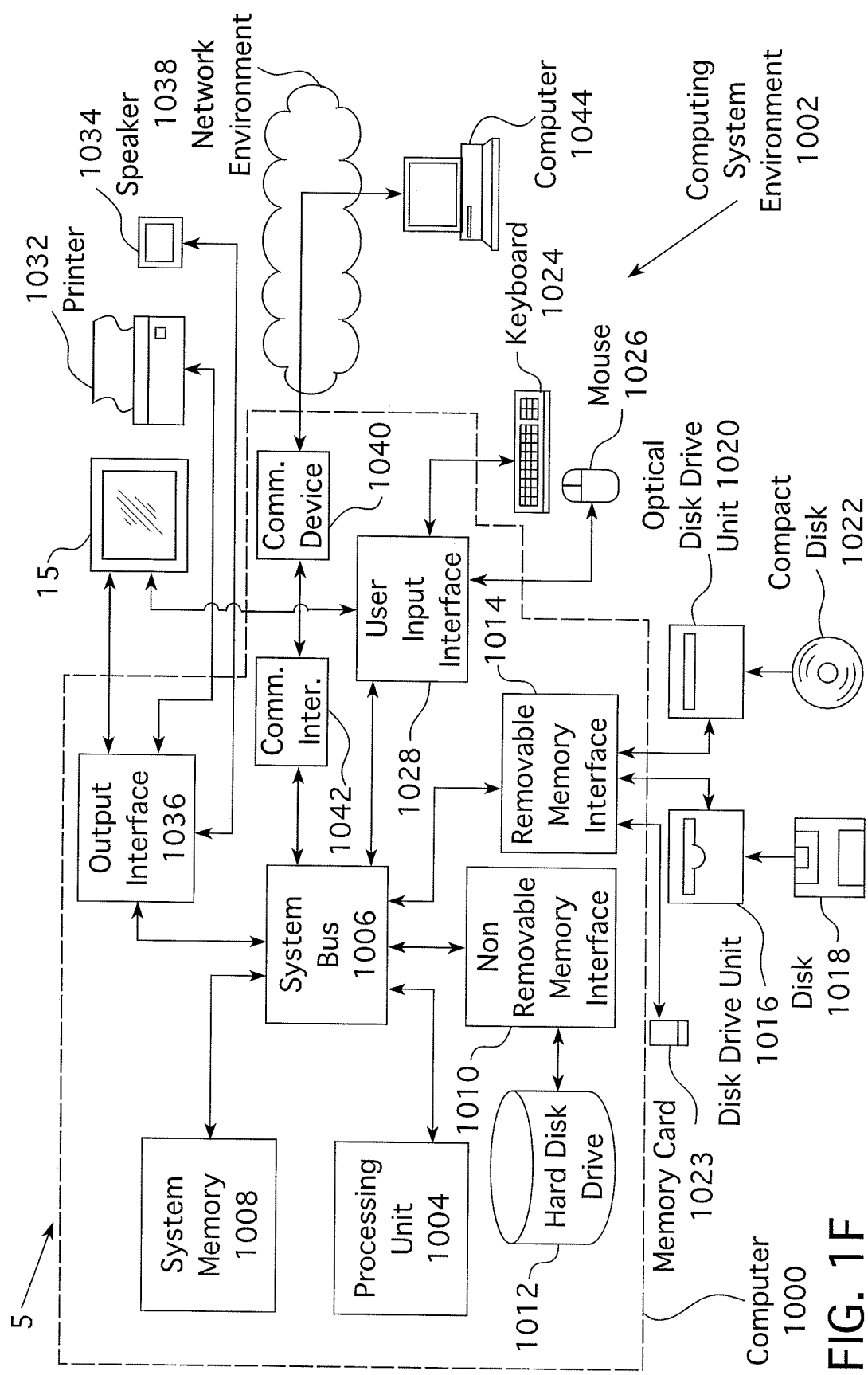
FIG. 1F is a block diagram illustrating a control system for use with the fluid delivery system of FIG. 1A.

With specific reference to FIG. 1F, GUI touch-screen display 15 may be part of a control system 5 embodied as a computer 1000 in a computing system environment 1002 used for controlling an injection procedure of the fluid delivery system 10. While any suitable computing device may be used to control the fluid delivery system 10, an exemplary embodiment of one computing system and computing system environment 1002 will be discussed hereinafter with reference to FIG. 1F. This computing system environment 1002 may include, but is not limited to, at least one computer 1000 having certain components for appropriate operation, execution of code, and creation and communication of data. For example, the computer 1000 includes a processing unit 1004 (typically referred to as a central processing unit or CPU) that serves to execute computer-based instructions received in the appropriate data form and format. Further, this processing unit 1004 may be in the form of multiple processors executing code in series, in parallel, or in any other manner for appropriate implementation of the computer-based instructions.

In order to facilitate appropriate data communication and processing information between the various components of the computer 1000, a system bus 1006 is utilized. The system bus 1006 may be any of several types of bus structures, including a memory bus or memory controller, a peripheral bus, or a local bus using any of a variety of bus architectures. In particular, the system bus 1006 facilitates data and information communication between the various components (whether internal or external to the computer 1000) through a variety of interfaces, as discussed hereinafter.

The computer 1000 may include a variety of discrete computer-readable media components. For example, this computer-readable media may include any media that can be accessed by the computer 1000, such as volatile media, non-volatile media, removable media, non-removable media, etc. As a further example, this computer-readable media may include computer storage media, such as media implemented in any method or technology for storage of information such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 1000. Further, this computer-readable media may include communications media, such as computer-readable instructions, data structures, program modules, or other data in a modulated data signal such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The computer 1000 further includes a system memory 1008 with computer storage media in the form of volatile and non-volatile memory, such as ROM and RAM. A basic input/output system (BIOS) with appropriate computer-based routines assists in transferring information between components within the computer 1000 and is normally stored in ROM. The RAM portion of the system memory 1008 typically contains data and program modules that are immediately accessible to or presently being operated on by processing unit 1004, e.g., an operating system, application programming interfaces, application programs, program modules, program data, and other instruction-based computer-readable code.

The computer 1000 may also include other removable or non-removable, volatile or non-volatile computer storage media products. For example, the computer 1000 may include a non-removable memory interface 1010 that communicates with and controls a hard disk drive 1012, i.e., a non-removable, non-volatile magnetic medium, a removable, non-volatile memory interface 1014 that communicates with and controls a magnetic disk drive unit 1016 (which reads from and writes to a removable, non-volatile magnetic disk 1018), an optical disk drive unit 1020 (which reads from and writes to a removable, non-volatile optical disk, such as a CD ROM 1022), a Universal Serial Bus (USB) port for use in connection with a removable memory card 1023, etc. However, it is envisioned that other removable or non-removable, volatile or non-volatile computer storage media can be used in the exemplary computing system environment 1002, including, but not limited to, magnetic tape cassettes, DVDs, digital video tape, solid state RAM, solid state ROM, etc. These various removable or non-removable, volatile or non-volatile magnetic media are in communication with the processing unit 1004 and other components of the computer 1000 via the system bus 1006. The drives and their associated computer storage media discussed above and illustrated in FIG. 1F provide storage of operating systems, computer-readable instructions, application programs, data structures, program modules, program data, and other instruction-based computer-readable code for the computer 1000 (whether duplicative or not of the information and data in the system memory 1008).

Desirably, an operator of the fluid delivery system 10 will enter commands, information, and data into the computer 1000 using the touch-screen of the GUI display 15 via an operator input interface 1028. However, it has been envisioned that an operator may enter commands, information, and data into the computer 1000 using other attachable or operable input devices, such as a keyboard 1024, a mouse 1026, etc., via the operator input interface 1028. Of course, a variety of such input devices may be utilized, e.g., a microphone, a trackball, a joystick, a touchpad, a scanner, etc., including any arrangement that facilitates the input of data and information to the computer 1000 from an outside source. As discussed, these and other input devices are often connected to the processing unit 1004 through the operator input interface 1028 coupled to the system bus 1006, but may be connected by other interface and bus structures, such as a parallel port, game port, or a USB. Still further, data and information can be presented or provided to an operator in an intelligible form or format through certain output devices, such as the GUI display 15 (to visually display this information and data in electronic form), a printer 1032 (to physically display this information and data in print form), a speaker 1034 (to audibly present this information and data in audible form), etc. All of these devices are in communication with the computer 1000 through an output interface 1036 coupled to the system bus 1006. It is envisioned that any such peripheral output devices be used to provide information and data to the operator.

The computer 1000 may operate in a network environment 1038 through the use of a communications device 1040, which is integral to the computer or remote therefrom. This communications device 1040 is operable by and in communication with the other components of the computer 1000 through a communications interface 1042. Using such an arrangement, the computer 1000 may connect with or otherwise communicate with one or more remote computers, such as a remote computer 1044 of a hospital information system, which typically includes many or all of the components described above in connection with the computer 1000. Using appropriate communications devices 1040, e.g., a modem, a network interface, or adapter, etc., the computer 1000 may operate within and communicate through a local area network (LAN) and a wide area network (WAN), but may also include other networks such as a virtual private network (VPN), an office network, an enterprise network, an intranet, the Internet, etc. It will be appreciated that the network connections shown are exemplary and other means of establishing a communications link between the computers 1000, 1044 may be used.

As used herein, the computer 1000 includes or is operable to execute appropriate custom-designed or conventional software to perform and implement the processing steps of the methods and systems disclosed herein, thereby forming a specialized and particular computing system. Accordingly, the presently-invented methods and systems may include one or more computers 1000 or similar computing devices having a computer-readable storage medium capable of storing computer-readable program code or instructions that cause the processing unit 1004 to execute, configure, or otherwise implement the methods, processes, and transformational data manipulations discussed herein. Still further, the computer 1000 may be in the form of a personal computer coupled to the fluid delivery system 10, a processor formed integrally with the fluid delivery system 10, a computer provided remotely from the fluid delivery system 10, or any other type of computing device having the necessary processing hardware to appropriately process data to effectively implement the presently-invented computer-implemented method and system.

Returning to FIGS. 1A-1E, the fluid delivery system 10 may include a retractable lid or cover 20 having a primary handle including a latch release 1 (see FIGS. 1D and 1E) and a secondary handle 21. The lid 20 may cover an upper surface 103 that defines a number of recessed portions, such as wells and troughs, into which a vial or container (see 902 in FIG. 4C) of a pharmaceutical or a radiopharmaceutical (discussed in more detail below) and various components of a multi-patient fluid path set 200 (hereinafter MPDS, discussed in more detail below) may be positioned during an injection procedure. A locking mechanism, such as a combination or a key lock (not shown), may be used to lock the lid 20 in a closed position to, for example, prevent use or access of the system 10 by unauthorized personnel. In another embodiment, the locking mechanism may be a software-implemented lock, such as a password-protected access point, that is accessible through the display 15 and is adapted to lock the cover in a closed position and/or to prevent unauthorized personnel from accessing or operating the system 10.

The lid 20 is slidable or retractable (by, for example, using primary handle and latch release 1) with respect to the cart 9 to allow for insertion and removal of the vial or container 902 and MPDS 200 from the fluid delivery system 10. The lid 20, upper surface 103, and various other portions of the cart 9 preferably include suitable radioactive shielding (such as lead) for minimizing potential radiation exposure from the radiopharmaceutical to the operator. In this manner, the radiopharmaceutical vial 902 and the components of the MPDS 200 can lie below the plane of surface 103, whereupon the surface 103 or one or more portions thereof can be covered by the lid 20 during use to limit radiation exposure to the operator or other medical personnel. Further, instead of a retractable lid 20, surface 103 itself could be disposed on a portion of the fluid delivery system 10 (e.g., a drawer-type mechanism) that slidably displaces with respect to a remainder of the fluid delivery system 10.

As further shown in FIGS. 1A, 1B, and 1D, the fluid delivery system 10 includes a pumping mechanism, such as a peristaltic pump 22, a removable/replaceable source of medical fluid 23 (such as saline), an output device such as printer 1032, and an interrupt button 25. The peristaltic pump 22 is shown in a closed position in FIG. 1A, but may be opened (see FIGS. 1B, 1C, and 2B) to receive a length of tubing 27 (see FIGS. 1C and 2A) in fluid connection with the source of medical fluid 23 to inject the fluid into a patient (discussed in more detail below). While a peristaltic pump 22 is currently preferred, any suitable type of pumping mechanism, such as a piston-driven syringe pump, gear pump, rotary pump, or in-line pump, may be used.

The printer 1032 may be used to generate records of the injection and/or imaging procedures performed on patients, for inclusion in patients' medical records or for billing or inventory purposes. The printer 1032 may be pivotally connected to the system 10 (see FIG. 1B) to allow an operator to load paper or labels into the printer 1032.

The interrupt button 25 allows an operator to quickly and easily pause or abort an injection procedure in the event of, for example, patient discomfort or an emergency, without having to resort to the GUI display 15 (which also can be manipulated to pause or abort an injection procedure). The interrupt button 25 may be connected to LEDs and/or a printed circuit board to provide visual and/or auditory alarms when the interrupt button 25 has been activated.

Turning to FIGS. 1C-1F, 2A, and 2B, additional features and components of the fluid delivery system 10, including the upper surface 103, the MPDS 200, a vial access system 600, and a single-patient fluid path set 700 (hereinafter SPDS), will be discussed.

As shown in FIG. 1C, the upper surface 103 generally defines wells and recesses or troughs into which various components of the MPDS 200 are situated. Specifically, a first recess or trough 107 accommodates a first tubing section 204 of the MPDS 200 and a tubing holder 150 for holding the tubing section 204 and preventing it from getting kinked or tangled with, for example, the SPDS 700. The first tubing section 204 may also include the tubing length 27 that is placed within the peristaltic pump 22 and is in fluid connection with the medical fluid source 23.

Figure 3A:
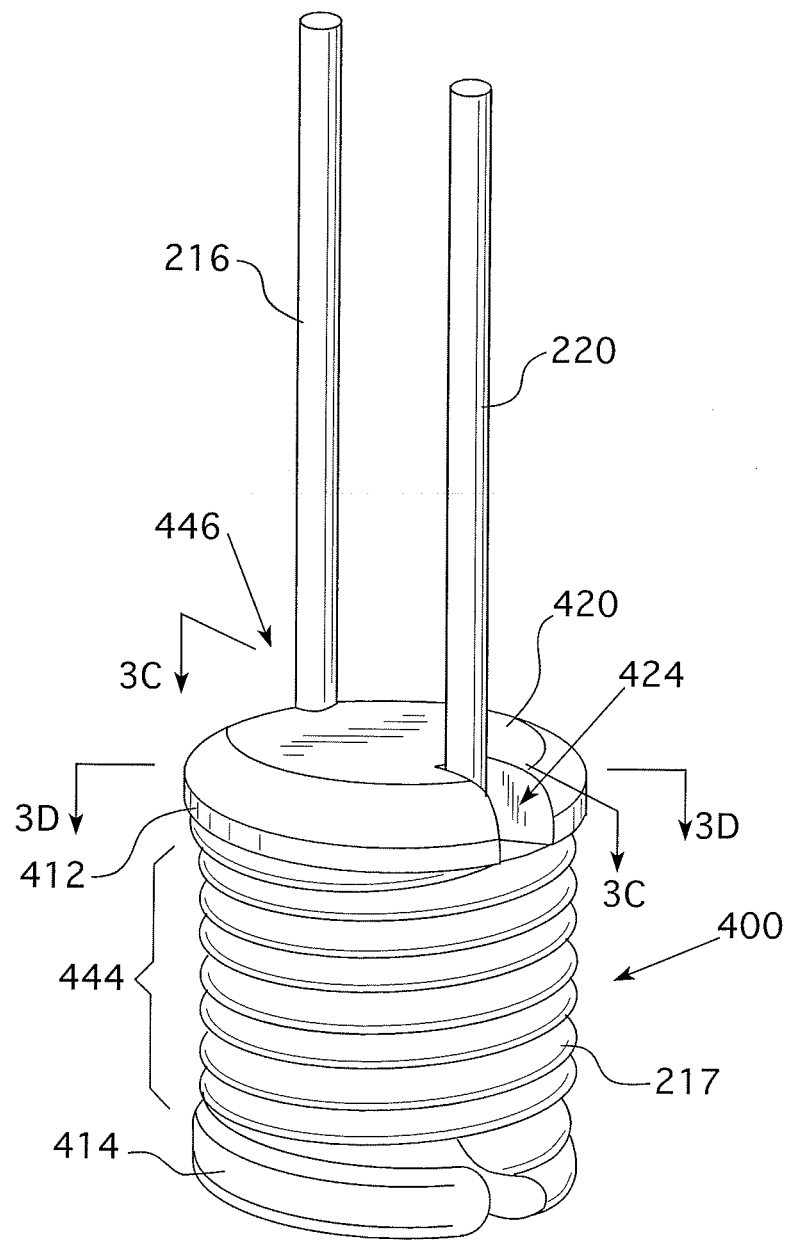
FIG. 3A is an elevational view of a coil assembly according to an embodiment.
Figure 3D:
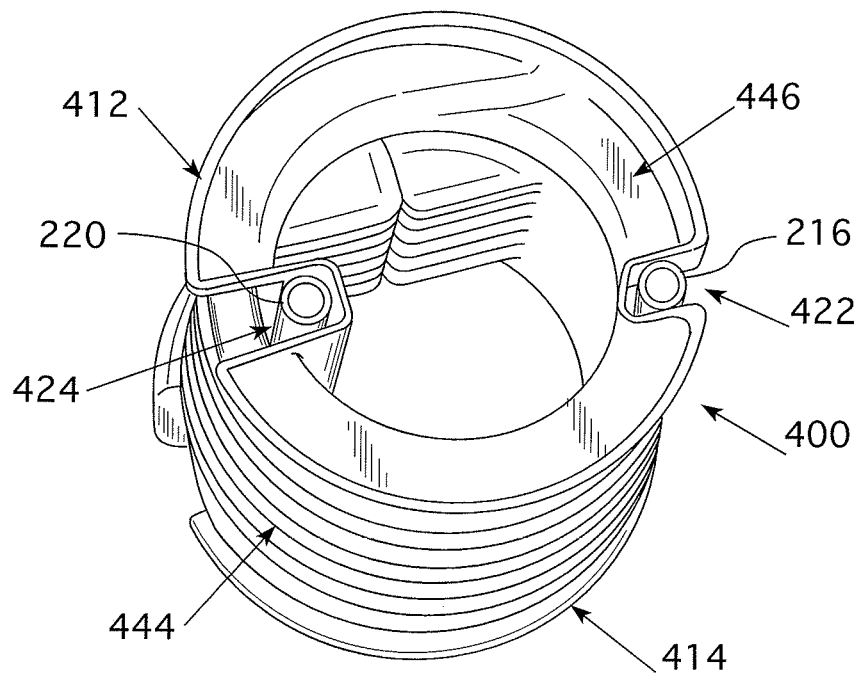
FIG. 3D is a cross-sectional view taken along line 3D-3D of FIG. 3A.

The first trough 107 leads into a second recess or trough 113 that accommodates a second pumping mechanism 180, such as a peristaltic pump, and a T-connector 205 (including check valves 214, 215) of the MPDS 200. As shown in FIG. 1C, the second trough 113 also leads to a first well 111 that accommodates a vial access system 600 and a radiopharmaceutical vial or container 902 disposed in a vial shield or PIG 554 (discussed in more detail below) and to a second well 121 that accommodates a dose calibrator or ionization chamber 160 for the fluid delivery system 10. As shown in FIGS. 1D and 3F, the ionization chamber 160 preferably accommodates a coil assembly 400 of the MPDS 200 (discussed in more detail below). Although the system is described as including an ionization chamber 160 for detecting activity of the radiopharmaceutical fluid, this is not to be considered as limiting the scope of this disclosure as any suitable activity detector may be used such as, but not limited to, a CZT crystal detector, a Geiger-Muller counter, a scintillating counter, and a parabolic detector, such as the parabolic sensor disclosed in U.S. patent application Ser. No. 12/664,653, now U.S. Pat. No. 8,198,599, which is hereby incorporated by reference.

A third recess or trough 125 extends from the second well 121 to a third well 127 and further along the surface 103 of the fluid delivery system 10. The trough 125 accommodates a T-connector 222 of the MPDS 200, two pinch valves 170, 172, an air detector 174, and a mount or retainer 176 for holding the connector end 228 of the MPDS 200. The pinch valves 170, 172 may be powered and controlled by the fluid delivery system 10, but alternately could be manually-operated. In another alternate embodiment, the pinch valves 170, 172 and the T-connector 222 of the MPDS 200 may be replaced with a manual or automated 3-way stopcock.

The third well 127 accommodates a waste receptacle or bag 224 for receiving medical fluid and/or pharmaceutical that is discarded during, for example, a priming procedure (discussed in more detail below) to prepare the system 10 for an injection procedure.

As shown in FIG. 1C, the SPDS 700 includes a length of tubing (preferably coiled, as shown) having a first end 702 that is attachable to the connector end 228 of the MPDS 200, and a patient end 704 having a luer connector that is attachable to, for example, a catheter (not shown) placed in a venous structure of a patient. As discussed in more detail below, the MPDS 200 may be used for multiple patients but the SPDS 700 is intended to be used on a per-patient basis and discarded after use with a single patient to prevent, for example, cross-contamination between patients.

As can be appreciated after reviewing FIG. 1A-1E, the secondary handle 21 of lid 20 overlies the tubing holder 150 and the mount 176 when the lid 20 and handle 21 are closed to cover the MPDS 200. The secondary handle 21 may be flipped open (from the closed position as shown in FIG. 1A) without retracting the cover 20 to allow an operator to connect the SPDS 700 to the MPDS 200 (as discussed in more detail below). As best shown in FIG. 1C, the SPDS 700 may be placed under the secondary handle 21 when it is closed.

The fluid delivery system 10 further includes the system controller 5 (see FIGS. 1D and 1E) in communication with the various components thereof, including the GUI 15, the pumps 22, 180, the dose calibrator or ionization chamber 160, the interrupt button 25, the air detector 174, the printer 1032, and motors 30, 31 (see FIG. 3F) for pinch valves 170, 172, respectively, for controlling the operation of the system 10. The system controller 5 may be embodied as the computer 1000 as discussed in greater detail hereinabove with reference to FIG. 1F.

As can be appreciated, the wells and troughs formed in the upper surface 103 can be sized, configured, or arranged as suitable for the length, design, or configuration of the MPDS 200 or other components thereof, including the radiopharmaceutical vial 902, vial shield 554, vial access system 600, ionization chamber 160, waste receptacle 224, etc.

It should be understood that FIG. 1C in no way is intended to convey dimensions or relative dimensions of the aforementioned recessed portions or MPDS components; instead, FIG. 1C conveys general positional relationships of such recessed portions with respect to one another.

It should further be understood and appreciated that the recessed portions shown and described with respect to FIG. 1C are encased throughout with suitable radioactive shielding to further minimize exposure to an operator.

Figure 2A:
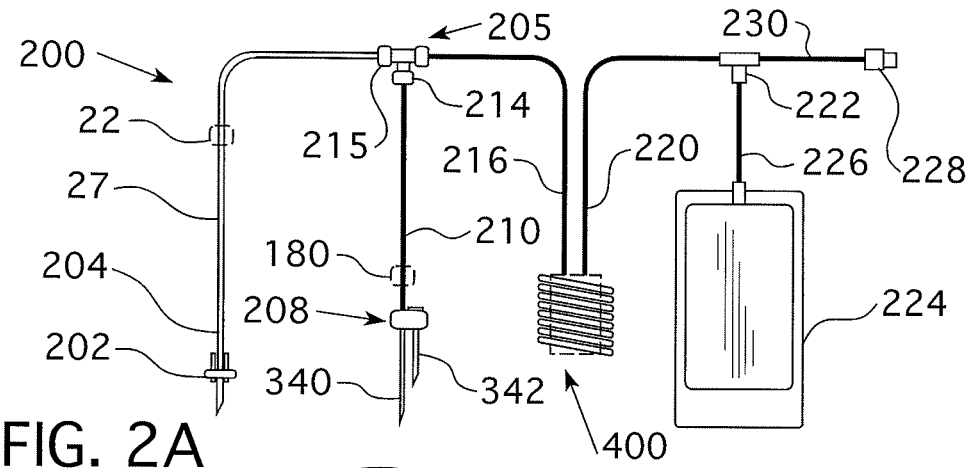
FIG. 2A is a schematic illustration of the multi-patient fluid path set and components thereof according to an embodiment.
Figure 2B:
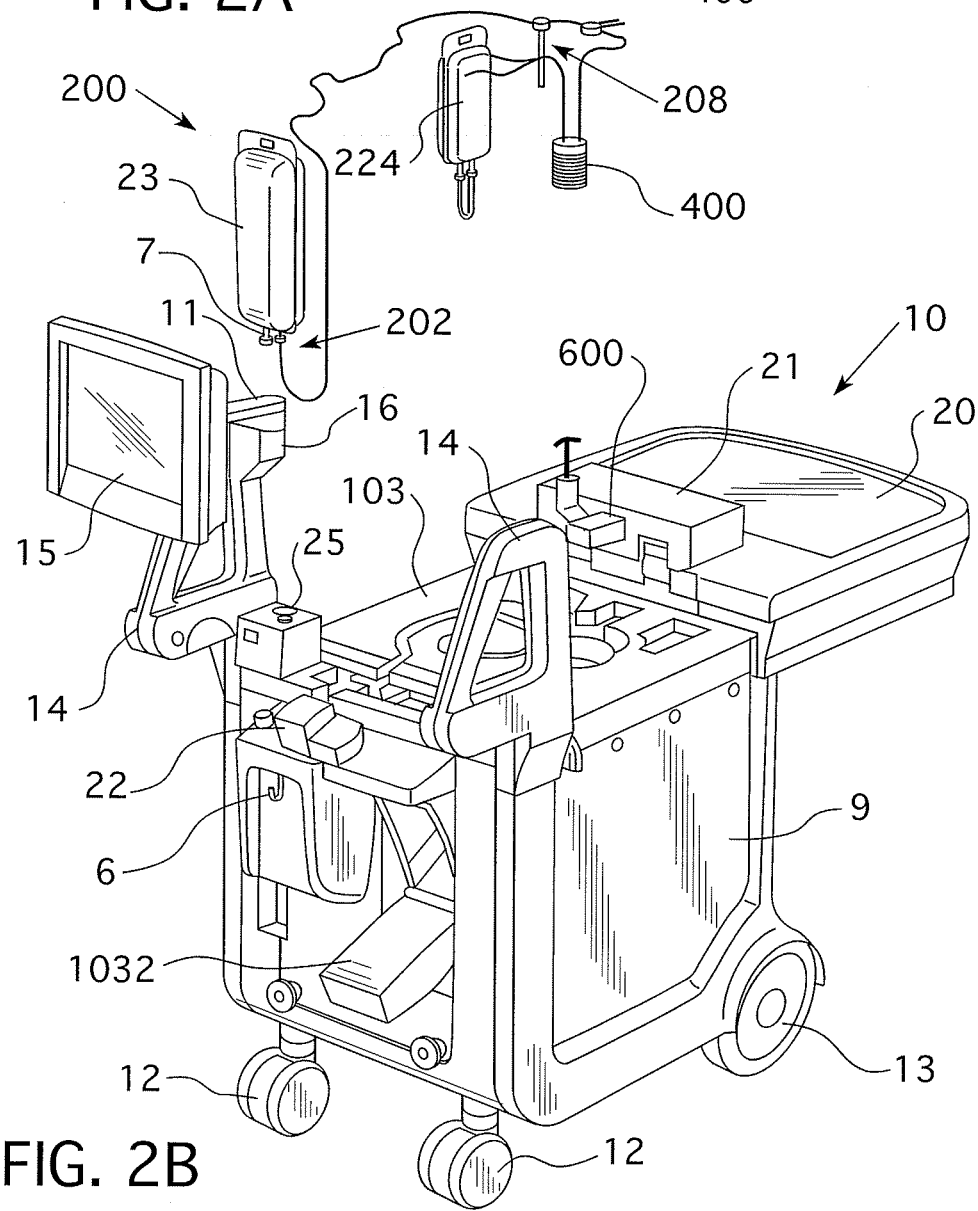
FIG. 2B is an exploded view showing the multi-patient fluid path set shown in FIG. 2A connected to a fluid source and disposed above the fluid delivery system shown in FIGS. 1A-1E.

Turning now to FIGS. 2A and 2B, an embodiment of the MPDS 200 and components thereof will be discussed. In addition, specific details of the coil assembly 400 employed in the MPDS 200 are shown and described with respect to FIGS. 3A-3F and FIG. 1D.

By way of a general overview, the MPDS 200 in accordance with at least one embodiment allows for FDG (or other radiopharmaceutical) to be drawn from a bulk radiopharmaceutical vial 902 and placed into a coil assembly 400 that allows an ionization chamber 160 to measure the amount of activity in the coil assembly 400. Once the system prepares a dose having the desired activity level, the fluid delivery system 10 will deliver the FDG dose to the patient (through the SPDS 700).

Generally, the MPDS 200 can be considered in terms of four components: (1) a medical fluid or saline component; (2) an FDG or pharmaceutical component; (3) a coil assembly component; and (4) a waste component. The saline component draws saline out of a bulk source 23 (e.g., via peristaltic pump 22). This is then used to prime the MPDS 200 (i.e., remove air therefrom), position FDG in the coil assembly 400 in the ionization chamber 160, and then deliver the dose to the patient.

The FDG component serves to draw FDG out of bulk radiopharmaceutical vial 902 (e.g., via peristaltic pump 180) and place the same into the fluid path to the ionization chamber 160.

The coil assembly component is employed to position the radiopharmaceutical to allow its radioactivity level to be optimally measured by the ionization chamber 160. Through the arrangement of the coil assembly 400 (as discussed in more detail below), the radiopharmaceutical can be optimally oriented and located within the "linear region" of the ionization chamber 160 to more accurately measure its activity level and prepare an optimal dose for injection into a patient.

The waste component holds the saline fluid and/or radiopharmaceutical that are discarded during the prime and dose preparation procedures, which are conducted to prepare the fluid path and the pharmaceutical dose for injection into a patient.

FIG. 2A schematically illustrates the MPDS 200 according to an embodiment. The MPDS 200 shown in FIG. 2A may be pre-connected as shown and may originally be stored in a sterile packet or container for use in an injector apparatus, such as fluid delivery system 10, when desired. For a non-restrictive and illustrative appreciation of a manner in which MPDS 200 can be incorporated in an injector apparatus, simultaneous reference may be made to FIGS. 1A-1E and 2B (and the discussion thereof hereinabove).

Primary components of MPDS 200 include, as shown: a spike 202 for connecting the MPDS 200 to the medical fluid or saline source 23; a vented cannula 208 for connecting with a source of FDG or other radiopharmaceutical; a coil assembly 400; a T-connector 205 with check valves 214, 215 for fluidly connecting the saline source 23, the radiopharmaceutical source, and the coil assembly 400; a waste bag 224; a connector end 228; and a T-connector 222 for fluidly connecting the coil assembly 400, the waste bag 224, and the connector end 228.

In general, MPDS 200 and fluid delivery system 10 are configured for priming (i.e., purging air from) the MPDS 200, delivering pharmaceutical (e.g., FDG) to a patient, and providing a saline flush, while minimizing or eliminating exposure of administering or operating personnel to the detrimental effects of the pharmaceutical and minimizing or eliminating creation of contaminated waste. Moreover, MPDS 200 and other elements disclosed herein also facilitate safe delivery of the pharmaceutical to multiple destinations (for example, dose delivery to a series of patients).

A T-connector 205 and check valves 214, 215 accommodate a first tubing section 204 that is in fluid connection with spike 202 and a second tubing section 210 in fluid connection with cannula 208. The check valves 214, 215 may be integrally formed with the T-connector 205 or may be separate components, or they could be combined into a single dual check valve. The check valves 214, 215 prevent saline from being pumped by peristaltic pump 22 into second tubing section 210 and the pharmaceutical from being pumped by peristaltic pump 180 into the first tubing section 204.

A third tubing section 216 leads to coil assembly 400 (including tube coil 444), and a fourth tubing section 220 leads from the coil assembly 400 to the T-connector 222. As described below, the tube coil 444 is formed from a tubing section 217 that has dimensions different from those of the third tubing section 216 and the fourth tubing section 220.

A fifth tubing section 226 leads from the T-connector 222 to the waste receptacle 224 and a sixth tubing section 230 leads from the T-connector 222 to the connector end 228. As shown above in FIG. 1C, the connector end 228 mates with the first end 702 of the SPDS 700 for delivery of a pharmaceutical to a patient.

The connector end 228 may be a swabable luer valve (Part No. 245204024 provided by Halkey-Roberts Corporation of St. Petersburg, Fla.) that is biased to close or seal off the connector end 228 of the MPDS 200 when the SPDS 700 is not connected thereto. The swabable luer valve prevents the MPDS 200 from being contaminated and allows an operator to swab or clean (by, for example, an alcohol wipe) the connector end 228 prior to connecting an SPDS 700 thereto. Alternately, however, the connector end 228 may be a standard luer connector as known in the art.

As schematically shown in FIG. 2A, the tubing length 27 of the first tubing section 204 can be placed within pump 22 (indicated by dotted lines) to pump saline or other medical fluid from source 23 and a portion of the second tubing section 210 can be placed within pump 180 (indicated by dotted lines) to pump a radiopharmaceutical from a radiopharmaceutical source.

Absolute and relative dimensions of the components shown in FIG. 2A, including tubing, may be chosen to best suit the applications at hand. The first tubing section 204 may be approximately 56.75 inches in length, has an outer diameter (OD) of approximately 0.188 inches and an inner diameter (ID) of approximately 0.062 inches, and has a 45 durometer. The second tubing section 210 may be approximately 8.75 inches in length and is formed of microbore tubing having an OD of about 0.094 inches and an ID of about 0.032 inches and a 45 durometer. The third tubing section 216 may be approximately 15 inches in length, has an OD of approximately 0.163 inches and an ID of approximately 0.062 inches, and has a 60 durometer. The fourth tubing section 220 may be approximately 12 inches in length, has an OD of approximately 0.163 inches and an ID of approximately 0.062 inches, and has a 60 durometer. The fifth tubing section 226 and the sixth tubing section 230 may each be approximately 5 inches in length, have an OD of approximately 0.163 inches and an ID of approximately 0.062 inches, and have a 60 durometer. The tubing in tube coil 444 may be approximately 41 inches in length, has an OD of about 0.218 inches and an ID of about 0.156 inches, and an 80 durometer. All of these dimensions are provided for exemplary purposes only and are not to be construed as limiting the present disclosure.

The microbore tubing of second tubing section 210 may be formed of, for example, silicone, C-Flex, or silicone-like PVC material. Essentially, the use of microbore tubing in second tubing section 210 improves volume accuracy and thereby improves measured activity accuracy (i.e., of pharmaceutical delivered to the patient) and reduces radiopharmaceutical waste.

By way of tubing material for the other tubing sections 204, 216, 220, 226, 230 and tube coil 444, essentially any suitable polymeric material, including standard PVC or pump tubing, may be employed.

Referring again to FIGS. 1A-2B, the placement of the MPDS 200 in the fluid delivery system 10 and the connection of the SPDS 700 will now be discussed. To set up the system 10 at, for example, the beginning of the day, the operator lifts the secondary handle 21, grasps the primary handle and latch release 1, and retracts the lid 20 to reveal the upper surface 103 of the system 10. If a used MPDS 200 is present in the system 10, the operator will remove and discard it.

A new MPDS 200 may be removed from its (typically sterile) packaging and placed in the system 10 as shown in FIG. 1C. This includes placing the waste receptacle 224 into well 127, placing coil assembly 400 into ionization chamber 160, placing second tubing section 210 into operative connection with pump 180, placing the tubing length 27 of the first tubing section 204 into operative connection with pump 22 and tubing holder 150, placing vented cannula 208 into fluid connection with radiopharmaceutical source or vial 902 located in well 111, placing fifth tubing section 226 in operative connection with pinch valve 170, and placing sixth tubing section 230 in operative connection with pinch valve 172, air detector 174, and mount 176. A saline source 23 may be hung on a hook 6 (see FIGS. 1A, 1B, and 2B) or otherwise mounted on fluid delivery system 10, and spike 202 is inserted into port 7 (see FIGS. 1A, 1B, and 2B) of source 23 to fluidly connect the MPDS 200 to the source 23. Of course, this installation procedure does not need to be completed in the order described above, but may be completed in any suitable order consistent with the description or drawings hereof.

After the MPDS 200 is installed and primed (as discussed below), the first end 702 of the SPDS 700 is connected to the connector end 228 of the MPDS 200 and the SPDS 700 is primed to provide a wet connection at the patient end 704 of the SPDS 700, which is then connected to a catheter (not shown) located in a patient. The SPDS 700 may be a coiled tubing formed of standard PVC, approximately 60 inches in length and having an OD of approximately 0.100 inches and an ID of approximately 0.060 inches and a 90 durometer.

As shown in FIGS. 2A and 2B, the MPDS 200 includes a coil assembly 400. In the broadest sense, coil assembly 400 may include a section of tubing (including portions of third and fourth tubing sections 216, 220) that is simply gathered (in a coiled or an uncoiled, amorphous fashion) and placed inside ionization chamber 160.

As shown in FIGS. 3A-3F, however, a more desirable embodiment of coil assembly 400 includes a (preferably thermoformed) core element or structure 446 that is preferably configured for allowing tubing section 217 to be wrapped thereupon and to assume the coiled tube section indicated at 444. As such, the coiled tube section or tube coil 444 may be formed on the core element 446 to facilitate optimal positioning of the tube coil 444 within the ionization chamber 160.

To facilitate positioning of the tube coil 444, the core element 446 may include a tube channel 410 defined by shoulders 412, 414 (see FIG. 3B) that retain tube coil 444 therebetween to hold the tube coil 444 in position and to prevent tube kinking. Further, the upper surface 420 of core element 446 defines an inlet channel or groove 422 and an outlet channel or groove 424 to accommodate third tubing section 216 and fourth tubing section 220, respectively.

The core element 446 preferably may be self-centering when inserted into the sleeve 162 of the ionization chamber 160 of the fluid delivery system 10 to thereby facilitate optimal performance (see FIG. 3F). This may be achieved either through structural features of the coil assembly 400, the structure of core element 446 itself, or a combination thereof when used with the sleeve 162 of the ionization chamber 160.

Figure 3E:
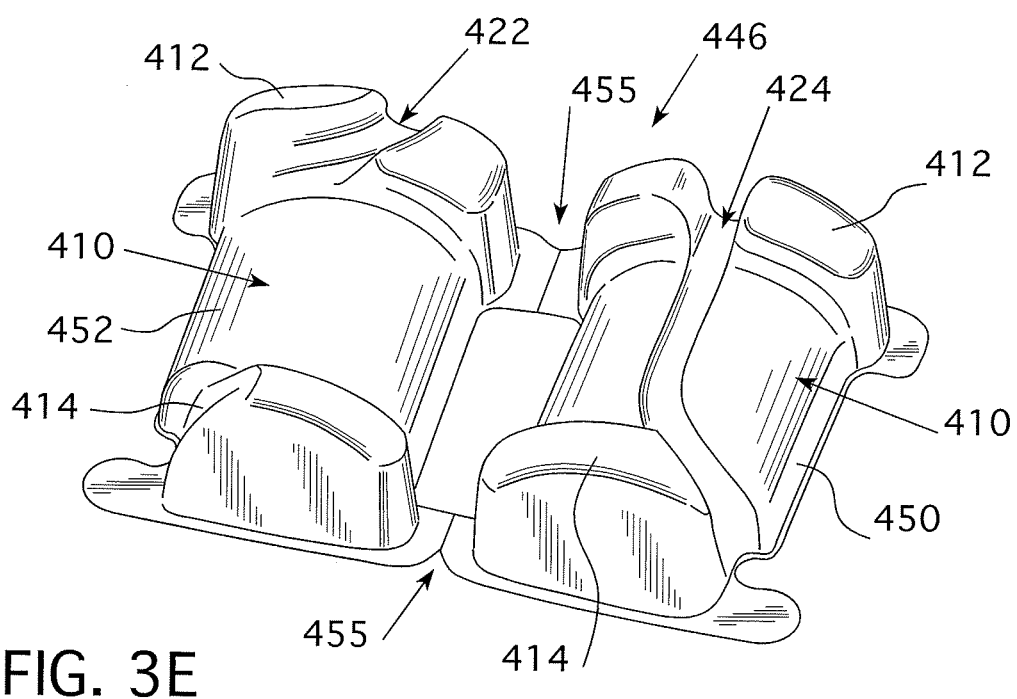
FIG. 3E is a perspective view of the core element of the coil assembly shown in FIG. 3A.
Figure 3F:
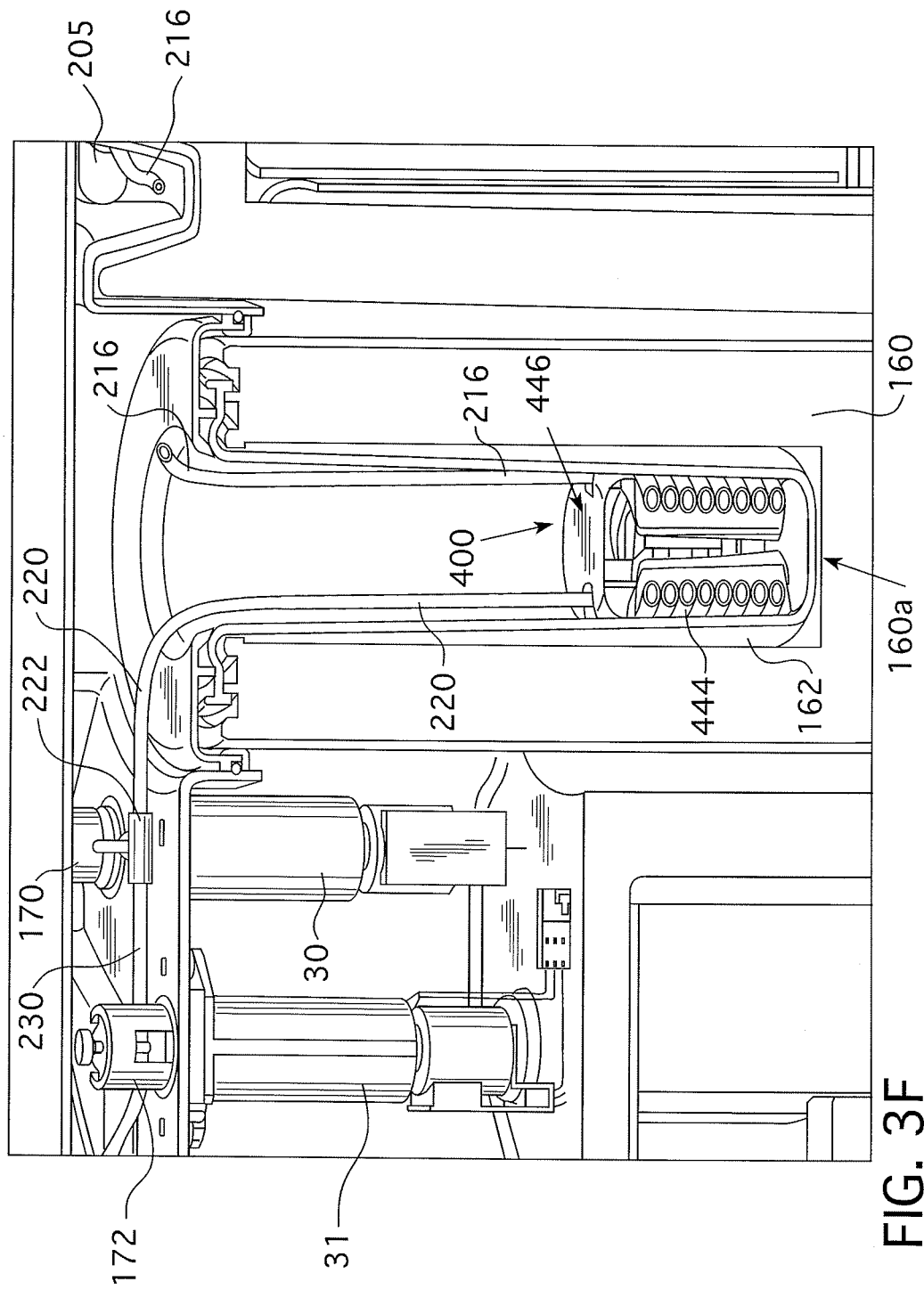
FIG. 3F is an enlarged view of FIG. 1D showing the coil assembly in the ionization chamber of the fluid delivery system.

As best shown in FIG. 3E, the core element 446 may be formed by folding two elements (450, 452) together along an integral hinge 455. Suitable form-locking mechanisms can be molded onto the core element 446 to facilitate clasping of the elements 450, 452 together.

FIGS. 1C, 1D, and 3F show coil assembly 400 positioned concentrically in the sleeve 162 of the ionization chamber 160. The core element 446 and the tube coil 444 are sized and dimensioned so that the coil assembly 400 is optimally positioned within the "linear region" of the ionization chamber 160 so that the ionization chamber 160 can accurately determine the activity level of one or more volumes of radiopharmaceutical that is located within the tube coil 444. The "linear region" of an ionization chamber is the region in which activity level measurements are repeatable and predictable. For an exemplary ionization chamber (Model IK-102 Short Ionization Chamber provided by Veenstra Instruments) used in system 10, the "linear region" is located within a window of 5 mm to 65 mm measured from the base or bottom wall 160a of the ionization chamber 160 (see FIG. 3F).

The tube coil 444 may be comprised of approximately 7 turns (see FIGS. 3A and 3B) formed from a length of tubing that is approximately 41.0 inches. As shown in FIG. 3B, the height h of the tube coil 444 is approximately 1.53 inches and the diameter w of the tube coil 444 is approximately 1.95 inches. The tube coil 444 is preferably formed from a tube having an OD of 0.218 inches and an ID of 0.156 inches. Further, based on the length and ID of the tubing, the tube coil 444 preferably has a volume capacity of approximately 12.5 ml.

As discussed heretofore, a source, container, or vial 902 (see FIG. 4C) of a pharmaceutical or radiopharmaceutical is placed into the fluid delivery system 10 (e.g., in well 111 formed in upper surface 103) to prepare and perform an injection procedure. A radiopharmaceutical container or vial 902 is typically placed in a conventional vial shield or PIG 554 for transport by personnel.

Figure 4A:
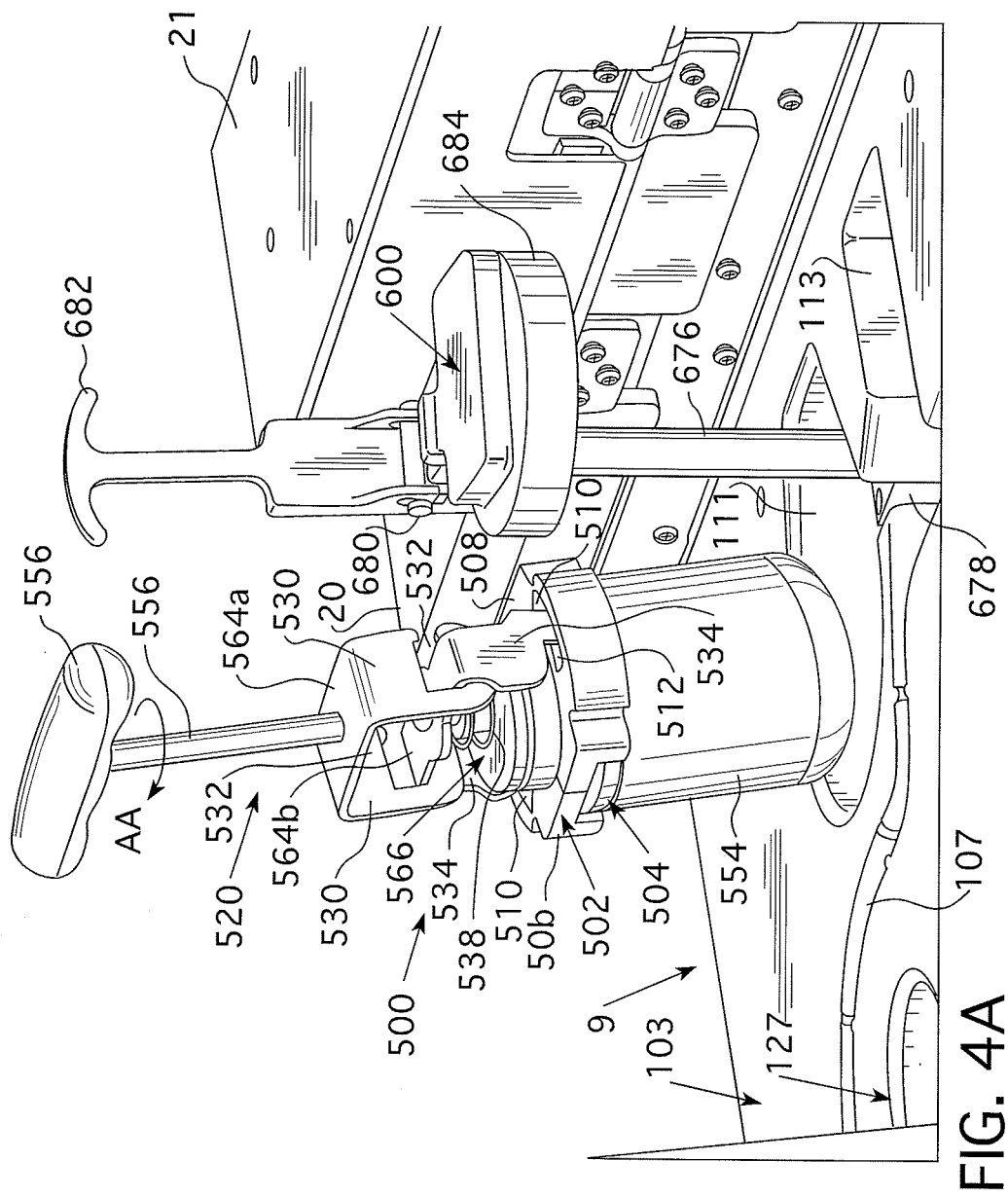
FIG. 4A is an elevational view of a vial shield carrying system and a vial access system according to an embodiment.
Figure 4B:
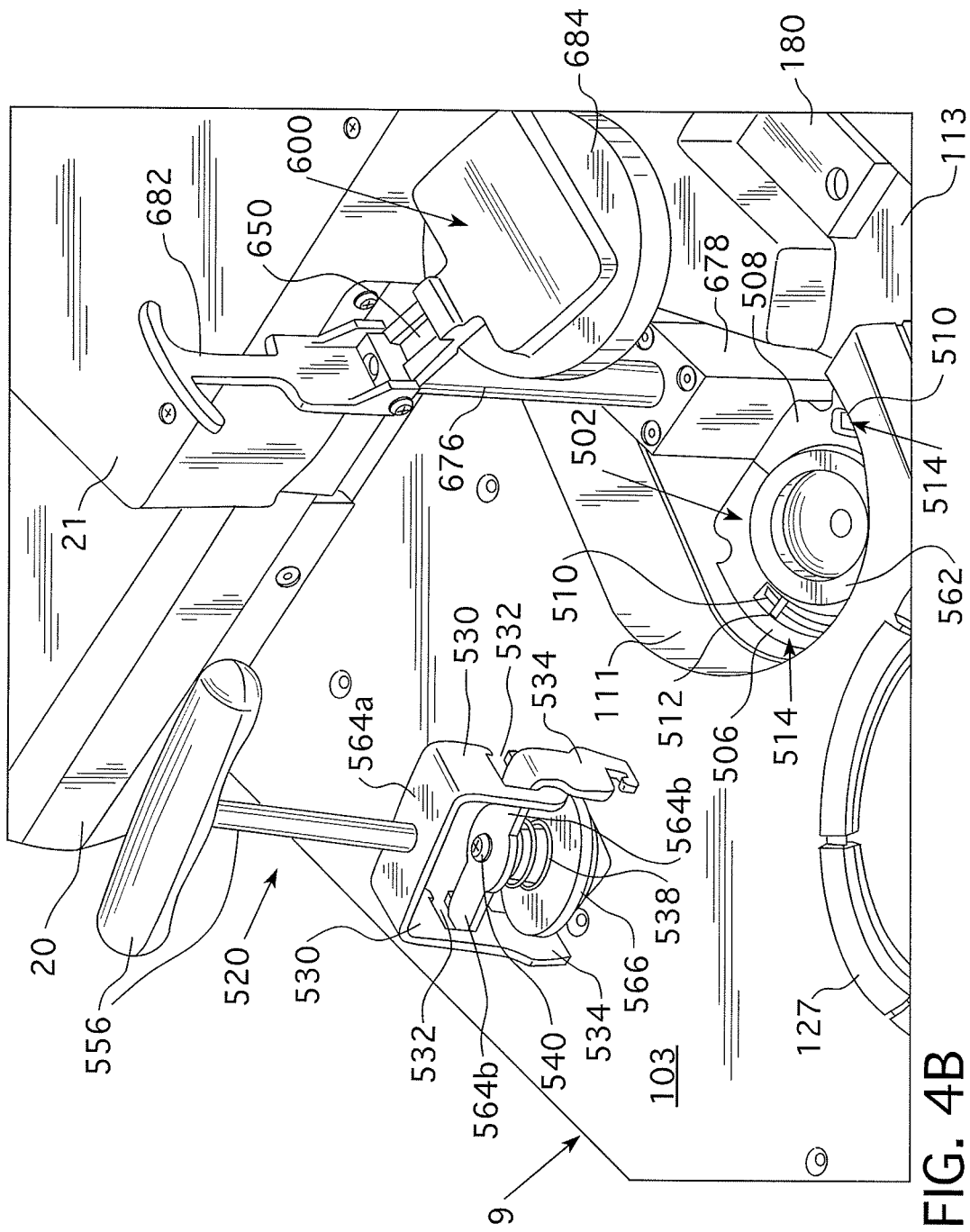
FIG. 4B is a perspective view showing the vial shield, the vial shield carrying system, and the vial access system of FIG. 4A.
Figure 4C:
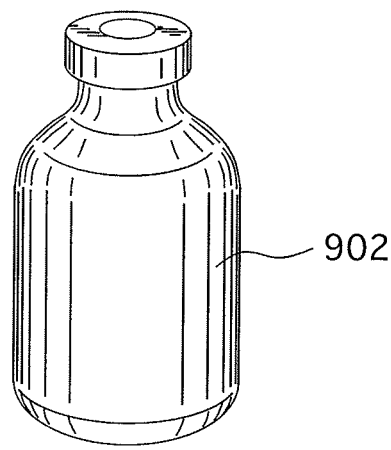
FIG. 4C is an elevational view of a pharmaceutical vial that may be used in the fluid delivery system according to an embodiment.

Turning now to FIGS. 4A and 4B, an exemplary embodiment of a vial shield carrying device or system 500 and a vial access system 600 are shown. Vial access system 600 is removably disposed within well 111 of fluid delivery system 10 and operates to hold vial shield 554 and to access the contents of the vial 902 contained therein.

As best shown in FIG. 4A, the vial shield 554 (containing a radiopharmaceutical vial 902) includes a flange 504 formed along a top end thereof and a removable septum cap 562 that is securely and removably engaged with the vial shield 554 (e.g., via threading) to allow insertion and removal of the vial 902 therefrom.

As shown in FIGS. 4A and 4B, the carrying system 500 includes a collar unit 502 that removably engages the flange 504 formed on the vial shield 554. The collar 502 may be formed in two pieces 506, 508 that are pivotally connected together (e.g., at one end thereof) to allow the collar 502 to engage and disengage the flange 504.

The collar 502 includes two elongated slots 510 formed in a top surface therein. As best shown in FIG. 4B, the slots 510 each include a pin 512 disposed therein and extending between two opposing walls 514 thereof.

The carrying system 500 further includes a handle unit 520 that engages with the collar unit 502 and the septum cap 562 to allow the vial shield 554 (and vial 902) to be carried and installed in the fluid delivery system 10. The handle unit 520 includes a handle 556 that is rigidly connected to a generally U-shaped cross piece 564a. The cross piece 564a defines two downwardly extending arms 530 having slots 532 formed thereon.

The slots 532 each form a slight hook on the ends thereof and are adapted to engage and retain a second cross piece 564b that supports a plunger 566 having a generally frustoconical shape that mates with a generally frustoconical recess of the septum cap 562 (see FIG. 4B).

The second cross piece 564b is also generally U-shaped and defines two downwardly extending arms 534 having hooks 536 formed therein. The open ends of the hooks 536 are formed on opposite ends of the arms 534 and are adapted to accept and retain the pins 512 in slots 510 of collar 502. The slots 510 are sized to provide sufficient clearance for the arms 534 to be inserted thereinto (in a downward direction) and for the hooks 536 to engage pins 512 (through rotation of handle 556).

The plunger 566 is connected to the second cross piece 564b by means of a connector (such as a screw 540) and a spring 538. The plunger 566 is biased by spring 538 to ensure a tight fit between the plunger 566 and the septum cap 562.

To engage and carry the vial shield 554, the collar 502 is connected to the flange 504 of the vial shield 554 as described above. The handle unit 520 is then moved into proximity to the vial shield 554 (by an operator grasping the handle 556 and moving the unit 520 into position) and the arms 534 are lowered into the slots 510 of the collar 502. At substantially the same time, the plunger 566 is engaged with the septum cap 562, with the spring 538 ensuring a tight fit between the two. The operator then turns the handle unit 520 in a clockwise direction (see arrow AA in FIG. 4A) to seat the pins 512 in slots 510 into the hooks 536 of arms 534.

The operator then lifts the combined vial shield 554 and vial carrying system 500 (by moving the handle unit 520 in an upward direction) and transports it to, for example, the fluid delivery system 10. The operator then lowers the vial shield 554 into the vial access system 600 disposed in well 111 (see FIG. 4A) and rotates the handle unit 520 in a counter-clockwise direction to disengage the hooks 536 from the pins 512. The operator then lifts the handle 556 in an upward direction to remove the arms 534 from the slots 510 and the plunger 566 from the septum cap 562, thereby leaving the vial shield 554 (with septum cap 562 and collar 502) in vial access system 600 in well 111 (see FIG. 4B).

In an exemplary embodiment, the plunger 566 includes radioactive shielding (such as lead) to shield the operator from radiation that would otherwise leak through or be emitted from the septum of the septum cap 562. Together with the vial shield 554 and the septum cap 562, the plunger 566 of the vial carrying system 500 shields the operator from the radiation emitted by the radiopharmaceutical and prevents unnecessary radiation exposure. Further, by extending the handle 556 from the vial shield 554, the distance between the two functions to lessen any possible radiation exposure to the operator.

As discussed above with respect to FIGS. 4A-4B, the fluid delivery system 10 includes a vial access system 600 that is removably disposed within well 111 of fluid delivery system 10 and is adapted to hold vial shield 554 and to provide access to the contents of the vial 902 within vial shield 554.

Because vials (such as vial 902 described herein) typically come in various sizes, such as 10 ml, 15 ml, 20 ml, and 30 ml, the fluid delivery system 10 is intended to accommodate various vial sizes. To do so, the fluid delivery system 10 may include one or more vial shields and vial access systems. Thus, depending on the size of the vial used at a clinical site or for a particular procedure, an operator of the fluid delivery system 10 can select the appropriate vial shield and vial access system and place it in the well 111 of the fluid delivery system to enable a fluid injection procedure.

Referring again to FIGS. 1C and 2A, once the MPDS 200 is installed in the fluid delivery system 10, the spike 202 is placed in fluid connection with the saline source 23 and the cannula 208 is inserted into the vial 902 and placed in fluid connection with the pharmaceutical therein, and an injection procedure can be implemented.

An exemplary injection procedure is discussed hereinafter with reference to FIGS. 5-11. Many variations on the injection procedure may be implemented within the scope of the present disclosure. For instance, the container 902 of radiopharmaceutical may be any suitable multi-dose container configuration. This multi-dose container configuration may include a dose of radiopharmaceutical for a plurality of patients provided in any suitable container for storing radiopharmaceuticals. The multi-dose container configuration may include a dose of radiopharmaceutical for a plurality of patients provided in a syringe. In addition, the multi-dose container configuration may be a plurality of containers suitable for storing radiopharmaceuticals where each container stores a certain amount of a radiopharmaceutical composition. A micro-fluidic device or other radiopharmaceutical generation technology capable of real-time generation of a certain amount of a radiopharmaceutical may also be utilized as the multi-dose container configuration. Furthermore, the multi-dose container configuration may be a plurality of suitable containers each holding a different radiopharmaceutical fluid. The multi-dose container configuration may also be a pre-loaded amount of radiopharmaceutical fluid in a coil of tubing of an administration set. Alternatively, a single dose container may also be utilized. Accordingly, the injection procedure described hereinafter is not to be construed as limiting this disclosure and while a container 902 is described hereinafter, this is not to be construed as limiting as any variety of radiopharmaceutical container may be used. Furthermore, the following procedure describes the use of a first volume, bolus, or slug 800 and a second volume, bolus, or slug 802 of radiopharmaceutical delivered to a patient. This also is not to be construed as limiting the injection procedure disclosed herein as any suitable number of slugs may be delivered to the patient.

An exemplary injection procedure can generally be divided into five phases. In an initialization phase 910, the device is brought into a well-defined initial state. In a calibration phase 920, steps are performed for calibrating the radioactivity in container 902. In a delivery phase 930, the radiopharmaceutical is delivered to the destination. In a step 940, it is decided whether another injection shall be performed. If yes, operation will continue again with the calibration phase 920. If no, a shutdown phase 950 will follow.

Before starting the operation, the operator will have to determine two quantities: the desired activity Ar to be injected to the patient; and the estimated concentration of activity in the vial (activity per unit of volume, e.g., expressed in MBq/ml) Cv. These data are provided to the system controller 5. Operation then starts with the initialization period 910.

Figure 5:
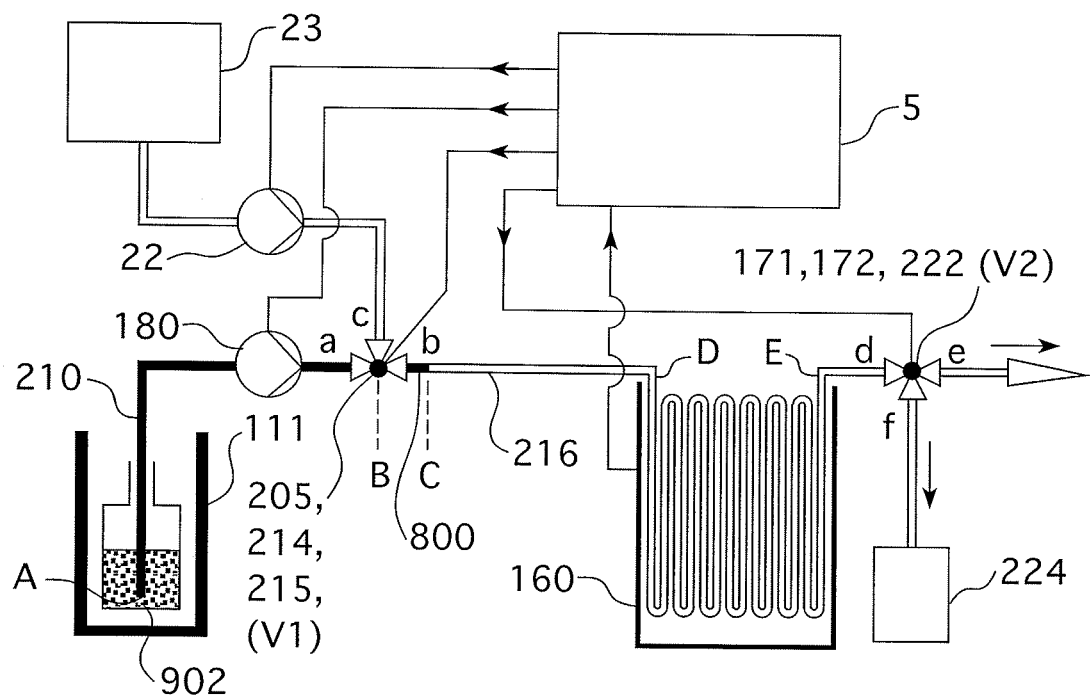
FIG. 5 is a simplified schematic illustration of the fluid delivery system of FIG. 1A in a first state of operation according to an embodiment.

The initialization period 910 comprises the following steps:

Step 911 (Initial filling of radiopharmaceutical to point C): In a first step, the complete tubing is filled with saline, thereby excluding air from the tubing system. For this, T-connector 205, check valve 214, and check valve 215 (hereinafter valve V1) are placed in a state that connects ports "c" and "b", while T-connector 222, pinch valve 170, and pinch valve 172 (hereinafter valve V2) are placed in positions "d" and "e". Pump 22 flushes saline up to point B (see FIG. 5). Then the tubing section 210 is inserted into a vial containing saline. Valve V1 is brought into a state that connects ports "a" and "b", while valve V2 still connects "d" and "e". Pump 180 now flushes saline until the tubing is completely filled with saline from point A (see FIG. 5) to the destination beyond valve V2, and air is thus completely purged from the system. The tubing section 210 is then inserted into the vial 902 containing the radiopharmaceutical. Valve V1 is brought into a state that connects ports "a" and "b", while valve V2 connects ports "d" and "f". Pump 180 is operated to pump radiopharmaceutical in vial 902 from inlet point A and past point B at valve V1 to some point C in the third tubing section 216. The volume of radiopharmaceutical between points B and C in the third tubing section 216 does not need to be known exactly; it suffices to ensure that the section of tubing from A to B is filled completely with radiopharmaceutical, and that the activity in the volume between B and C is not larger than the desired end activity Ar. The situation at the end of step 911 is illustrated in FIG. 5, where the volume of radiopharmaceutical between points B and C is designated by reference number 800.

Figure 6:
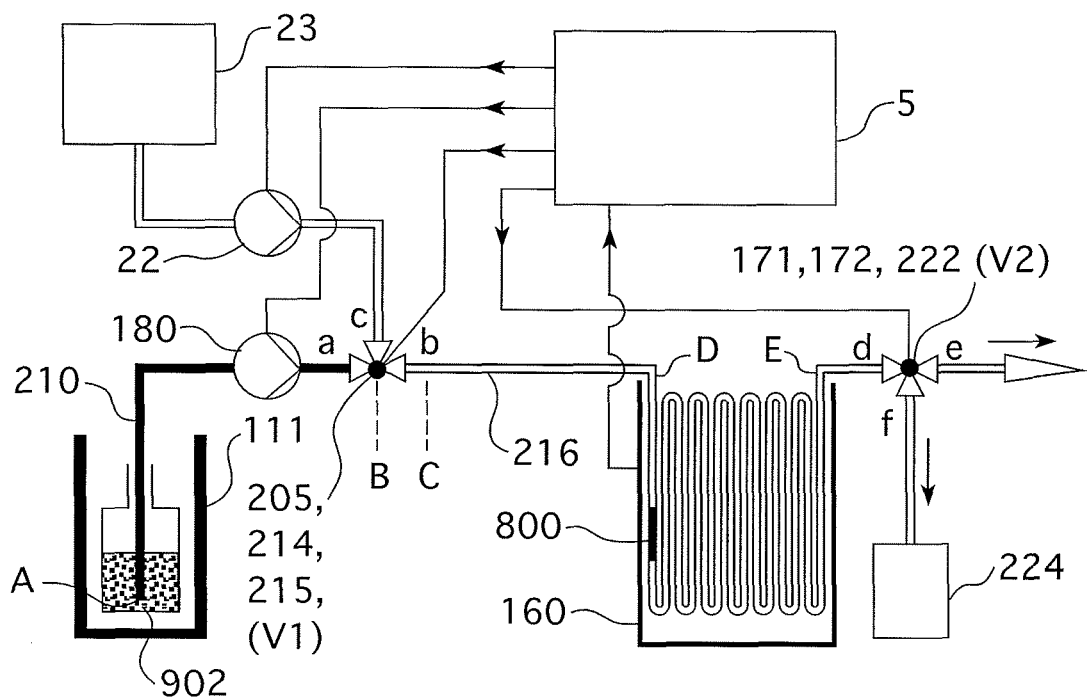
FIG. 6 is a simplified schematic illustration of the fluid delivery system of FIG. 1A in a second state of operation according to an embodiment.

Step 912 (Flushing of offset volume to dose calibrator): Valve V1 is now switched to a state in which it connects ports "c" and "b". Pump 22 is operated to pump saline from the source 23 towards valve V1. The volume to be pumped is slightly larger than the volume in the third tubing section 216, i.e., slightly larger than the volume between points B and D. This volume need not be known exactly. Thereby, the "offset volume" 800 is moved into the coil section 444. The situation at the end of this step is illustrated in FIG. 6.

Step 913 (Initial determination of activity): The activity of volume 800 in the coil section 444 is measured by the ionization chamber 160 (measurement M1). This activity will be called the "offset activity" A1. The system controller 5 now calculates the missing activity Am required to reach a total activity of Ar as shown in Equation 1 hereinafter:

$$Am = Ar - A1 \quad \text{(Equation 1)}$$

Figure 11:
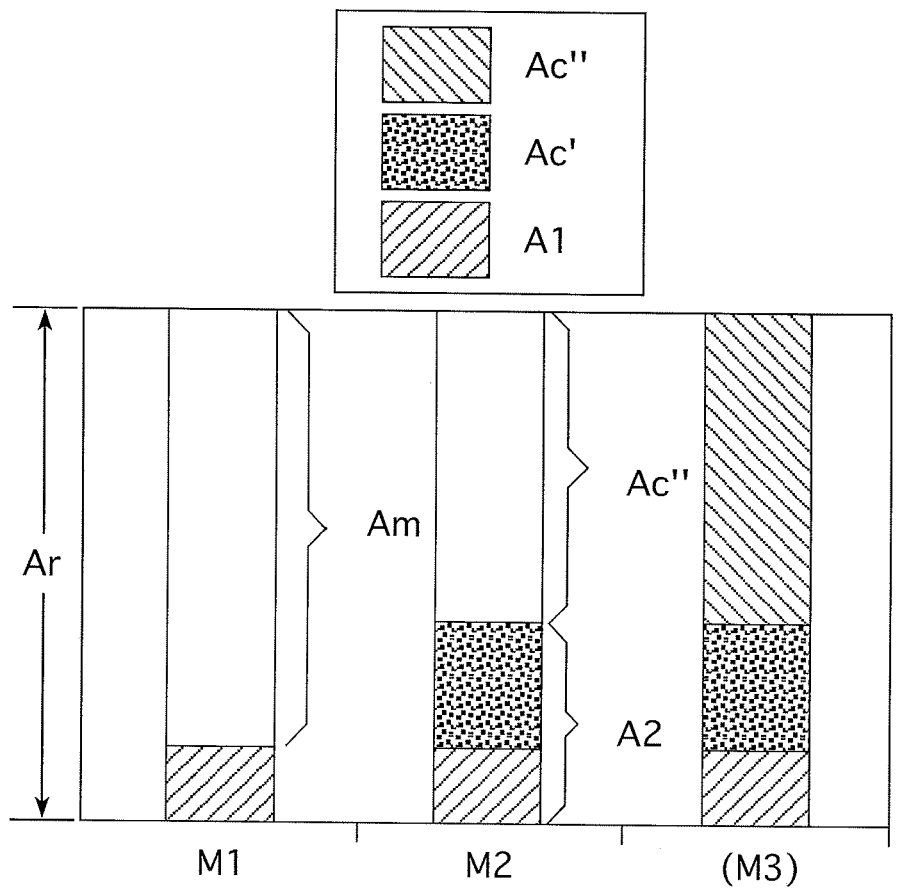
FIG. 11 is a bar graph showing the levels of activity measured in various stages of an injection procedure according to an embodiment.

This is illustrated in FIG. 11 in the leftmost column. From this and the estimated concentration of activity in the vial, Cv, the estimated missing volume Va1 still to be delivered is calculated as shown in Equation 2 hereinafter:

$$Va1 = \frac{Am}{Cv} \quad \text{(Equation 2)}$$

It is important to note that this calculation is still based on the estimate of the concentration of activity in the vial, and the result cannot be expected to be highly accurate. It is further important to note that no knowledge about the offset volume 800 is required in this calculation. In addition, ionization chamber 160 may be any suitable activity detector. Such detectors include standard Geiger-Müller counters, scintillating counters, an ionization chamber, a cadmium zinc telluride (CZT) crystal detector, etc., which should be calibrated to yield a sufficiently precise measure of the actual activity in the coil section 444. Desirably, the activity detector is an ionization chamber.

Figure 7:
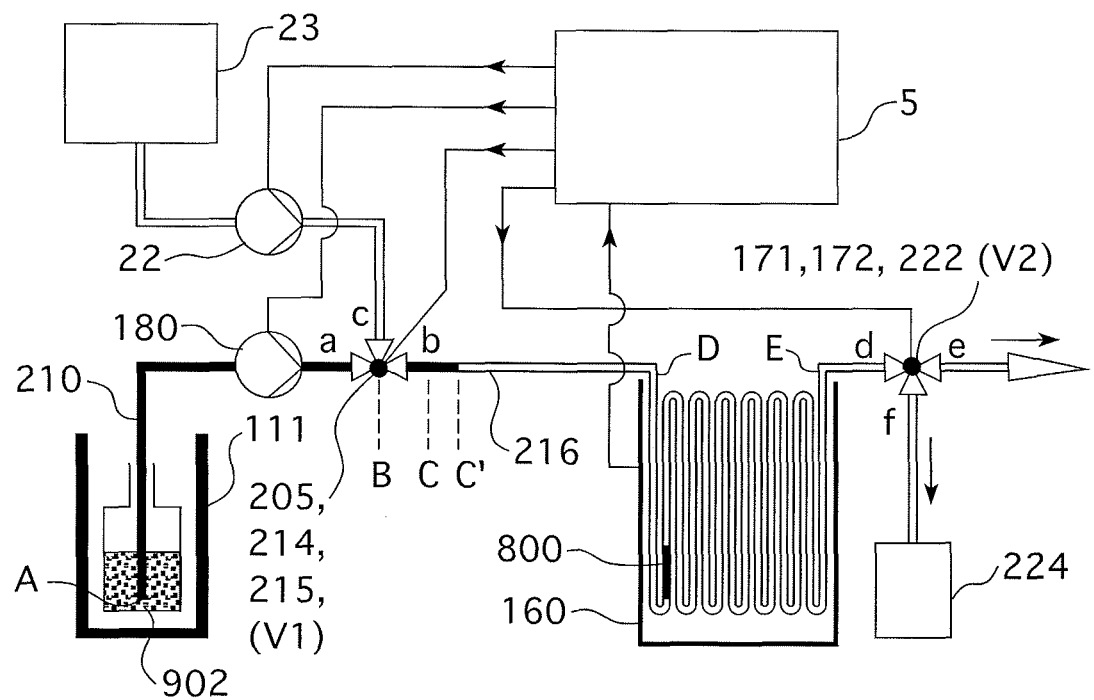
FIG. 7 is a simplified schematic illustration of the fluid delivery system of FIG. 1A in a third state of operation according to an embodiment.

This step concludes initialization 910. In the following calibration phase 920, the following steps are performed:

Step 921 (Filling of radiopharmaceutical to point C): Valve V1 is switched to a state in which it connects ports "a" and "b". Pump 180 is operated to pump a volume Vc' through valve V1, filling the fill-in section to point C. This situation is illustrated in FIG. 7, where this volume is designated by reference number 802. Volume Vc' is chosen to be approximately half of the estimated missing volume Va1 as set forth hereinafter in Equation 3:

$$Vc' \approx \frac{Va1}{2} \quad \text{(Equation 3)}$$

It is important to note that volume Vc' is known exactly in system internal units. The exact nature of these units depends on the type of pump used, e.g., the units could be pump revolutions, pump cycles, etc. If a volume flow meter is placed in-line with the pump, the units provided by the flow meter can be used as system internal units. Depending on the type of pump and the type of tubing, the resolution of volume in this step can be very small, and even small volumes can be delivered accurately. In addition, the predictive flow rate determination system as discussed in greater detail hereinafter may be used as system internal units.

Figure 8:
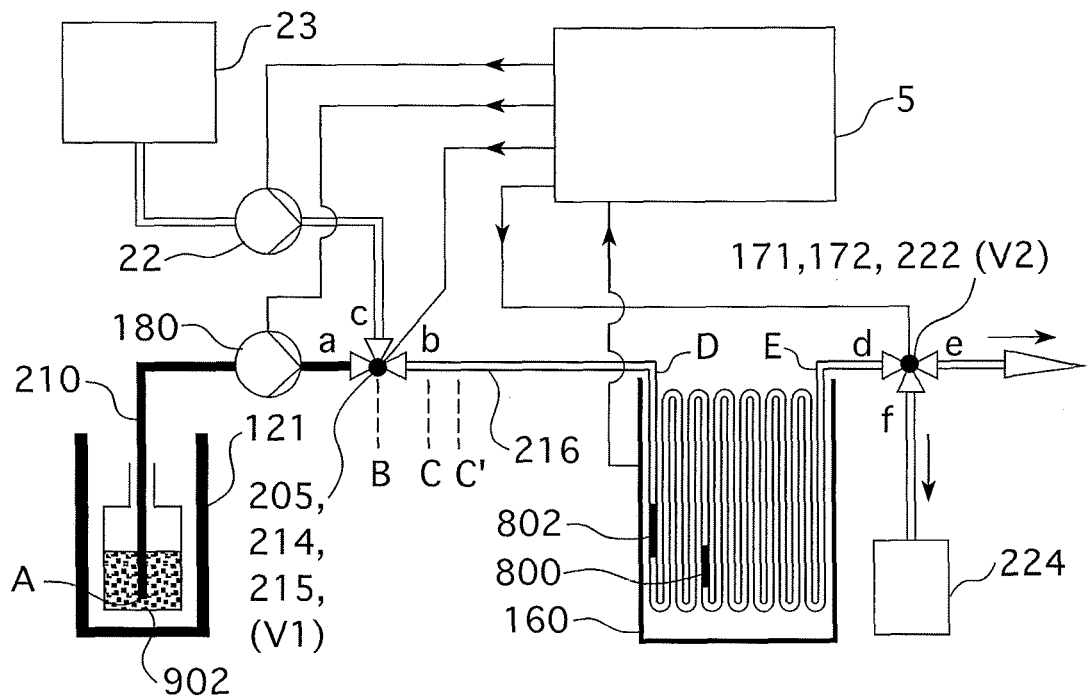
FIG. 8 is a simplified schematic illustration of the fluid delivery system of FIG. 1A in a fourth state of operation according to an embodiment.

Step 922 (Flushing of volume Vc' to the ionization chamber 160): Valve V1 is switched to connect ports "c" and "b". Pump 22 is operated to pump slightly more than the volume between points B and D of saline through valve V1. Thereby, volume 802, which is equal to Vc', of radiopharmaceutical is moved into the coil section 444. The situation at the end of this step is illustrated in FIG. 8.

Step 923 (Calibration of activity): The activity in the coil section 444 is measured by the ionization chamber (measurement M2). This activity level will be called A2. It corresponds to the sum of the offset activity A1 and the activity of the volume Vc', which will be called the "reference activity" Ac'. This is illustrated in the second column of FIG. 11. Now the activity concentration in the vial in system internal units, Cs, is calculated as set forth hereinafter in Equation 4:

$$Cs = \frac{Ac'}{Vc'} = \frac{(A2 - A1)}{Vc'} \quad \text{(Equation 4)}$$

The system is now calibrated in system internal units. Thereafter the volume Vc" is determined. The activity Ac" still required to reach a total activity of Ar is determined as set forth in Equation 5:

$$Ac'' = Ar - A2 \quad \text{(Equation 5)}$$

From this, the volume Vc" still to be delivered is calculated in system internal units as set forth in Equation 6 hereinafter:

$$Vc'' = \frac{Ac''}{Cs} = \frac{(Ar - A2)}{Cs} = \frac{(Ar - A2)}{(A2 - A1)Vc'} \quad \text{(Equation 6)}$$

Figure 9:
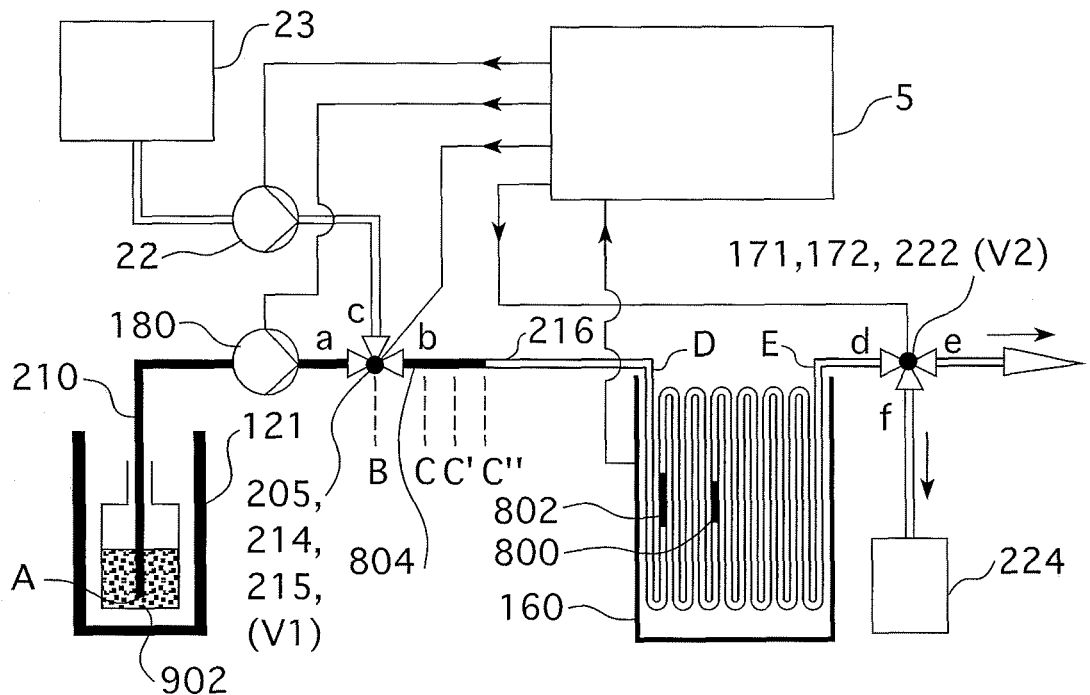
FIG. 9 is a simplified schematic illustration of the fluid delivery system of FIG. 1A in a fifth state of operation according to an embodiment.
Figure 10:
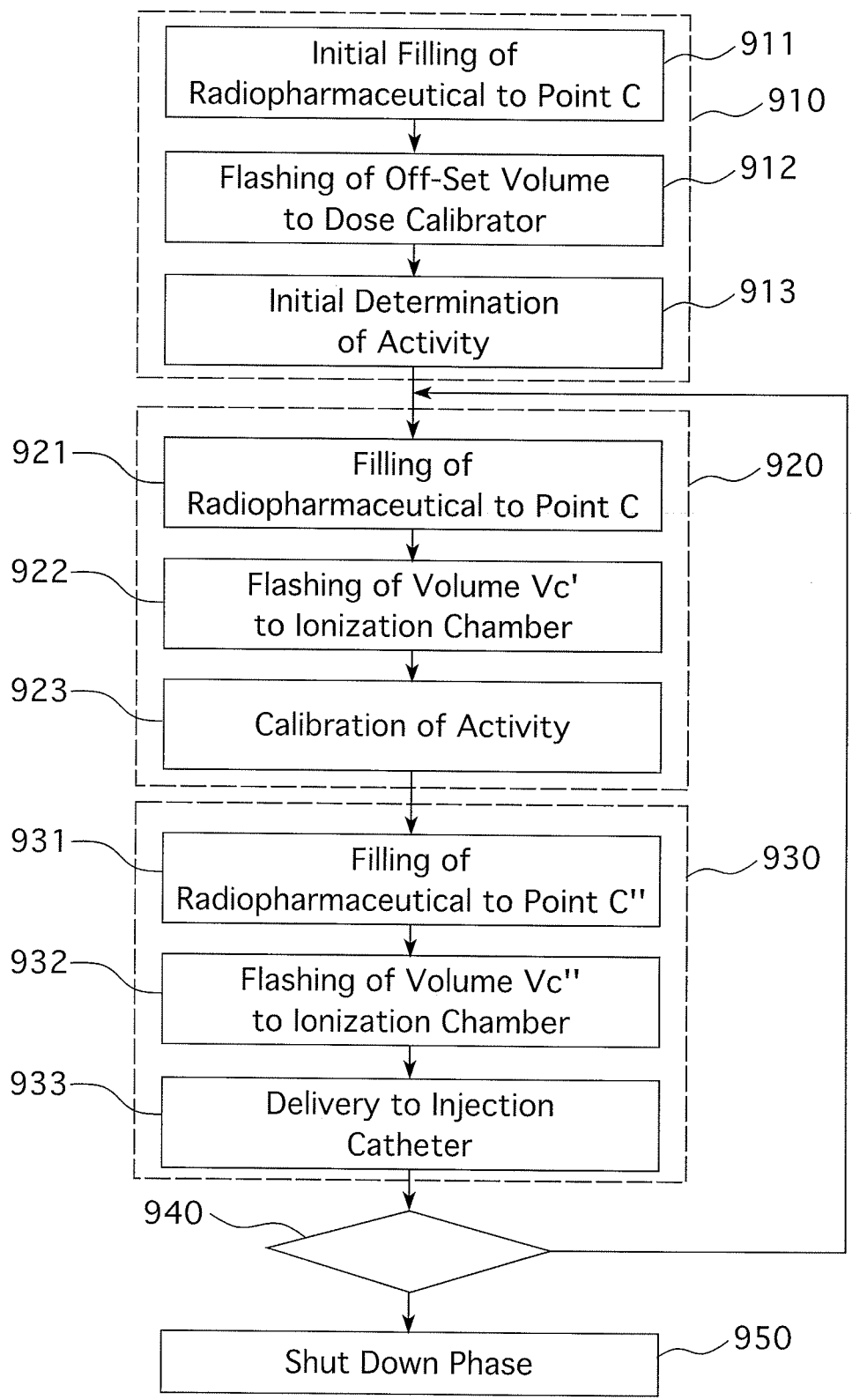
FIG. 10 is a flow diagram of a process for implementing an injection procedure according to an embodiment.

This completes the calibration phase 920. In the following delivery phase 930, the following steps are performed:

Step 931 (Filling of radiopharmaceutical to point C"): Valve V1 is switched to a state in which it connects ports "a" and "b". Pump 180 is operated to pump the volume Vc" through valve V1, filling third tubing section 216 to point C". This situation is illustrated in FIG. 9, where this volume is designated by reference number 804.

Step 932 (Flushing of volume Vc" to ionization chamber 160): Valve V1 is switched to connect ports "c" and "b". Pump 22 is operated to pump slightly more than the volume between points B and D of saline through valve V1. Thereby, volume 804, which is equal to Vc", of radiopharmaceutical is moved into the coil section 444. Alternatively, the total activity in the coil section 444 is now measured (optional measurement M3, see right column of FIG. 11). It should correspond exactly to the total desired activity Ar, provided that the volume of the coil section 444 is large enough to hold all three volumes 800, 802, and 804 within this section. The latter condition can always be fulfilled if the volume of the coil section 444 is at least five times the volume of the third tubing section 216. If a significant discrepancy is detected, the system is stopped.

Step 933 (Delivery to injection catheter): Valve V2 is switched to connect ports "d" and "e". Pump 22 is operated to pump at least the volume of the coil section 444, plus the volume of the tubing from the coil section 444 to the injection catheter and of the injection catheter itself, of saline through valve V1. Thereby, all liquid in the coil section 444 is flushed to the patient, and exactly the required dose of radioactivity is delivered to the patient.

This completes the delivery phase 930. If another injection of the same radiopharmaceutical (to the same or a different patient) is required, operation continues by repeating the calibration and delivery phases 920 and 930. Otherwise, operation stops by a suitable shutdown procedure, which may involve additional cycles of flushing with saline.

When repeating calibration phase 920, no additional initialization as in phase 910 is necessary, since the coil section 444 has been flushed with saline, and the radiopharmaceutical extends exactly to point B. No activity is present in the coil section 444. Therefore, in the above calculations, A1 can be set to zero in this case, and Am is set to Ar. No further changes are necessary. The three-phase procedure with phases 910, 920, and 930 now simplifies to a two-phase procedure with phases 920 and 930 only.

It will be appreciated that the various embodiments of the disclosed device and the associated methods of operation provide a number of inherent safety features. Specifically, there is a high degree of redundancy in the operation of the device, such that even in case of failure of one component, such as a pump or a valve, it is impossible that more than the desired dose will be delivered to the patient. Specifically, by its design the system will only allow the dose present within the coil section 444 to be delivered to the patient. This is because during the actual delivery of the radiopharmaceutical, there is no connection between the vial 902 and the fluid delivery line. The discrete nature of the sequential measurements of activity within the coil section 444 is another feature which increases safety. In step 932, the activity in the coil section 444 is actually known beforehand, and measurement M3 just serves to confirm that the right amount of activity is present in the coil section 444. If significant discrepancies are detected between the expected result and the actual measurement, operation will be stopped immediately, and an alarm will be given.

It will also be appreciated that, in normal operation, no radiopharmaceutical will enter the waste reservoir 224. Thus, generation of radioactive waste is minimized.

The disclosure now turns to particular embodiments, as illustrated in FIGS. 12-23, that could conceivably be employed in programming and operating a fluid delivery system as broadly contemplated herein.

Shown schematically in FIGS. 12-23 are various incarnations of a touch screen arrangement 1100 displayed on a graphical operator interface, such as GUI 15, that could be employed with the fluid delivery system 10. As a non-restrictive example, such a touch screen arrangement could be utilized in conjunction with the system controller 5 and/or computer 1000, 1044 of any of a variety of fluid delivery systems as broadly contemplated herein.

In order to clearly and unambiguously communicate to an operator the current status of the fluid delivery system 10, a GUI 15 with easily legible symbols and icons, including exceedingly operator-friendly data entry mechanisms, is broadly contemplated. An operator will thus be able to intuitively understand and undertake various tasks for operating fluid delivery system 10.

While a touch screen arrangement is contemplated in connection with FIGS. 12-23, it is to be understood that other types of data entry arrangements are conceivable that would achieve an equivalent purpose. For example, soft or hard key entry could be used, as well as trackball arrangements, mouse arrangements, or a cursor control touch pad (remote from the screen).

Figure 12:
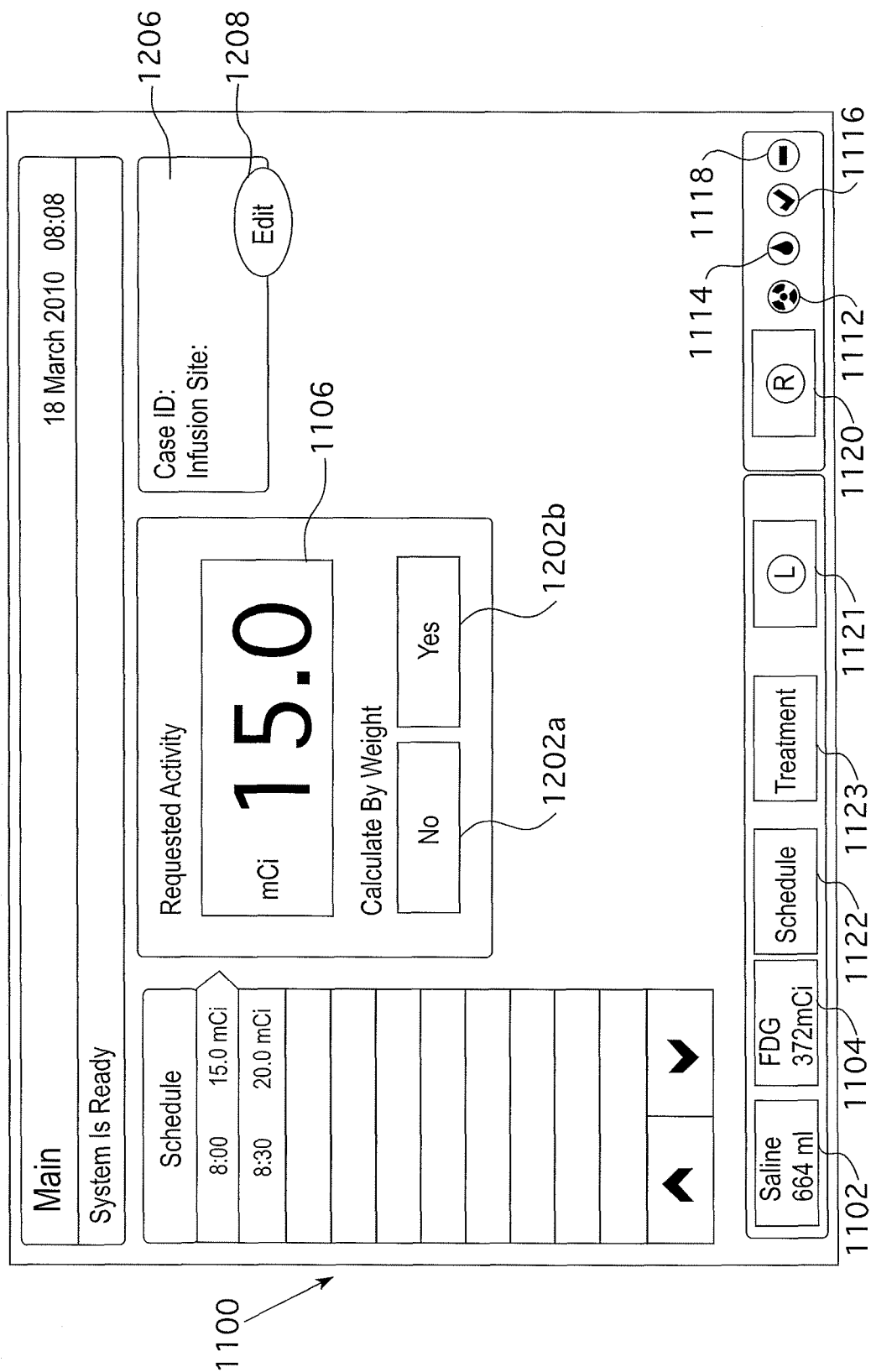

With continued reference to FIG. 12, a main operator interface provided on a touch screen is illustrated before an injection procedure has been started. After the operator prepares the system 10 for a fluid delivery procedure by, for example, completing the steps set forth in the initialization procedure 910 of FIG. 10, the system 10 generates the display 1100 shown in FIG. 12 which indicates in the upper left hand side thereof that the "System is ready". The touch screen includes a saline field 1102 and a pharmaceutical or FDG field 1104 providing an indication of the amount of saline in source 23 and FDG in vial 902, respectively. For example, the saline field 1102 indicates that 664 ml of saline is available and the FDG field 1104 indicates that 372 mCi of FDG are available, as shown. Indicated at 1106 is a touch field showing requested activity (currently displayed as 15.0 mCi) for an injection procedure to be performed. When the system 10 is activated, the requested activity field 1106 may display a default activity value that can be pre-programmed into the system 10 or pre-set by the operator. Alternatively, the requested activity field 1106 can default to the last activity level that was programmed into the system 10.

Indicated at 1112, 1114, 1116, and 1118, respectively, in FIG. 12 are circular status icons that provide quick and easy reference to different aspects of system status and, as such, will highlight when an aspect of system status is "on" or "active", or provide status information on the system 10. Thus, icons 1112-1118 from left to right, respectively, convey information on the following system aspects: activity present 1112, fluid motion/injection status 1114, check for air/priming status 1116, and system battery status 1118.

The system battery (not shown) provides power to the system controller 5 and to the ionization chamber 160 (to maintain the ionization chamber at its normal operating state) in the event that the system 10 is disconnected from an AC power source. The system battery is charged while the system 10 is connected to an AC power source.

FIG. 12 also shows four additional touch fields 1120-1123 along the bottom thereof. Reset button 1120 is activated to reset or clear information, such as case identification information, desired activity level, etc., from the treatment screens. Configuration button 1121 is activated to access the configuration screens for the system 10. Schedule button 1122 is activated to access a scheduling interface to allow an operator to schedule a plurality of injection procedures into the system 10. Treatment button 1123 is activated to access the injection control screen shown in FIG. 12.

As further shown in FIG. 12, the requested activity field 1106 indicates that 15.0 mCi is the current requested activity level. This 15.0 mCi activity level may be an operator-defined, default setting in the system 10, but also could be the desired activity level that was programmed for the last injection procedure.

The requested activity level may be set by the operator in one of two ways: (1) manual input; or (2) a calculation based on patient weight. If the operator wants to set the desired activity level by manual input rather than by patient weight, the operator activates the "No" button 1202a in requested activity field 1106. In response thereto, the system 10 generates, for example, a display and keypad that allows the operator to input the requested activity level.

If instead the operator wants to set the requested activity level based on patient weight, the operator activates the "Yes" button 1202b in FIG. 12. Upon activation of the "Yes" button 1202b, the system 10 generates a pop-up to prompt the operator to "Enter patient weight". Further, the operator can select the formula to be used in calculating the weight-based activity level. In one embodiment, the operator can select up to five operator-defined formulas. For example, the operator can select among three predefined formulas: (1) Standard (0.1 mCi/lb); (2) Melanoma (0.13 mCi/lb); and (3) Pediatric (0.07 mCi/lb). However, the system 10 can include more than preset or predefined weight-based formulas. For example, the system 10 can also include formulas based on other patient parameters, such as glucose-level or cardiac output, or scanner parameters, such as acquisition time. Once the formula is selected, the requested activity level is calculated using the formula and the patient's weight.

After the requested activity level is programmed or set by the system 10, the operator inputs case information including patient identification and injection site information into the system 10. When the operator activates the edit button 1208 in the case ID field 1206, a "Case Information" pop-up display is provided for inputting a patient or other identification number and an injection site at which the radiopharmaceutical will be administered or injected.

Figure 13:
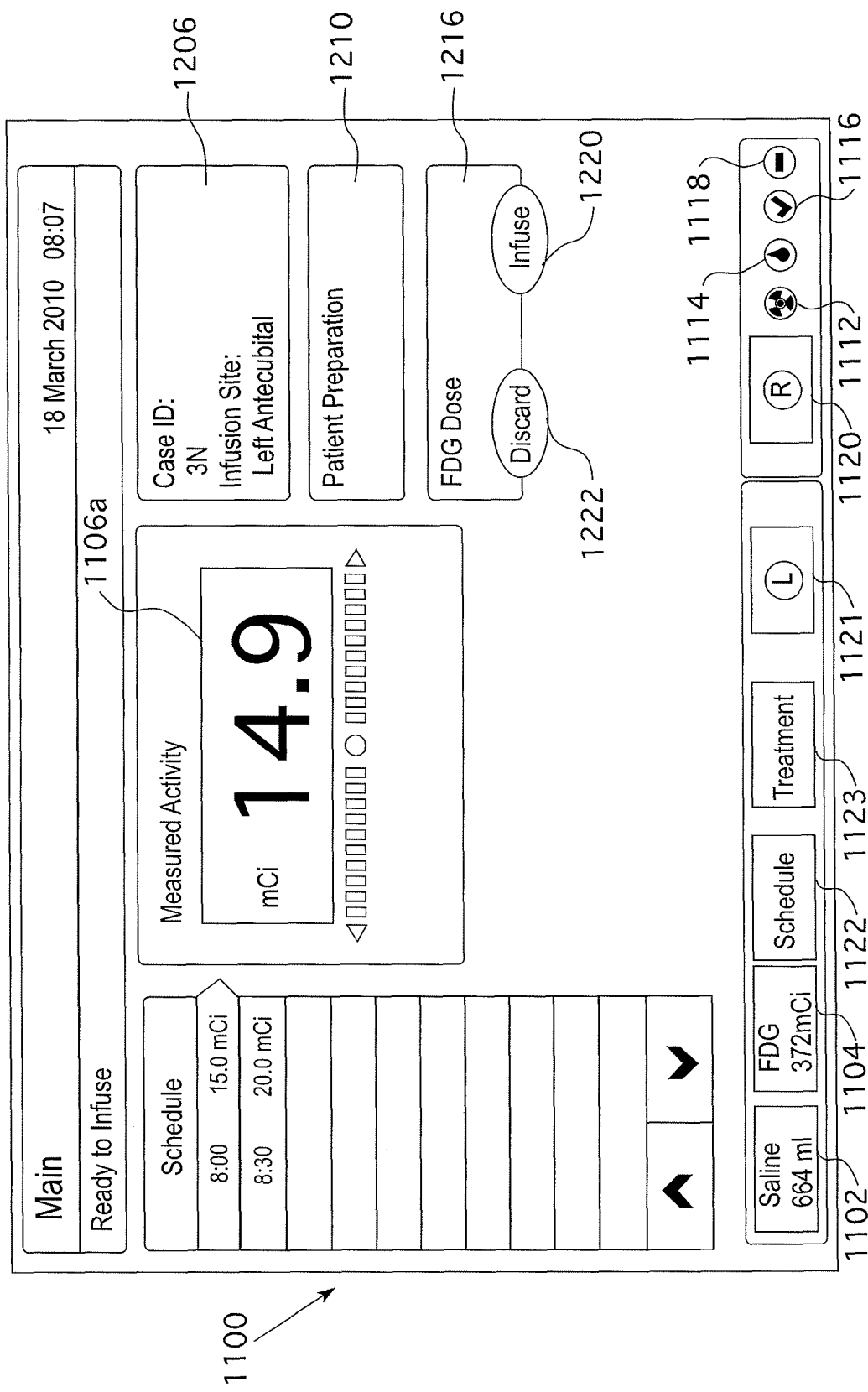

Once the identification and injection site information is input into the system 10, the information is displayed in the case ID field 1206, as shown in FIG. 13, for example. Further, after the requisite information is input into the system 10 and displayed in the case ID field 1206, a patient preparation field 1210 is generated and displayed for the operator.

After the SPDS priming operation is completed as discussed hereinabove, the patient end 704 of the SPDS 700 is connected to the patient, an FDG dose display 1216 appears having a corresponding "Prepare" button (not shown). After the operator activates the "Prepare" button, the system 10 begins to pump a volume of FDG (or other suitable pharmaceutical or radiopharmaceutical) from the vial 902 through the MPDS 200 to the tube coil 444 thereof disposed in the ionization chamber 160. The system 10 prepares the pharmaceutical dose in accordance with the methodology described hereinabove with reference to FIGS. 5-11, in which the activity level of a first amount of a radioactive liquid is measured and used to calculate a second amount of the radioactive liquid that is required for the combined amounts to have a pre-determined level of radioactivity to be delivered to a patient. The dimensions of the coil assembly 400 and the core structure 446, including the height, diameter, and volume of the tube coil 444, the length, number of turns, OD and ID of the tubing that forms the tube coil 444, and the dimensional location of the "linear region" of the Veenstra IK-102 ionization chamber provided above are necessary to optimally and accurately prepare the pharmaceutical dose.

The stated tube coil 444 dimensions are necessary to optimally position within the "linear region" of ionization chamber: (1) the volume(s) of pharmaceutical required to deliver the desired activity level to the patient; and (2) the volume of saline necessary to position the total volume of pharmaceutical in the tube coil. The tube coil 444 could be formed from tubing having a larger ID than that stated above (i.e., 0.156 inches), but larger IDs tend to allow the radiopharmaceutical to be diffused with the saline (which is used to place or position the radiopharmaceutical within the tube coil 444), which may result in the radiopharmaceutical volume or a portion thereof being positioned outside of the tube coil 444 and thus outside of the "linear region" of the ionization chamber (resulting in inaccurate activity level measurements and delivery). Likewise, the tube coil 444 could be formed from tubing having a smaller ID than 0.156 inches (which would possibly further decrease or prevent the diffusion of the radiopharmaceutical with the saline), but the dimensions of the tube coil 444 (e.g., length of tubing, coil tube height, number of turns) required to maintain a tube coil volume of 12.5 ml would result in the tube coil 444 extending beyond the "linear region" of the ionization chamber (resulting in inaccurate activity level measurements and delivery).

Further, the core structure 446 operates to maintain the desired tube coil geometry (e.g., tube coil diameter and height) and to properly position the tube coil 444 axially and vertically within the sleeve 162 so that the tube coil 444 thereby resides within the "linear region" of the ionization chamber 160 (see FIG. 3F).

The 12.5 ml volume of the tube coil 444 is designed to accommodate two volumes of a radiopharmaceutical from vial 902 separated by a volume of saline from source 23, regardless of whether the dose is prepared shortly after the radiopharmaceutical was assayed (when a small volume of the radiopharmaceutical is required to deliver a desired activity level) or after a significant amount of time has passed (e.g., in relation to the radioisotope's half-life) since the radiopharmaceutical was assayed (when a greater volume of the radiopharmaceutical is required to deliver the same desired activity level). As a specific example of the above, the 12.5 ml tube coil 444 is designed to accommodate: (1) two $\frac{1}{16}$ ml volumes or "slugs" of a pharmaceutical (for a total volume of $\frac{1}{8}$ ml) at a concentration of 40 mCi/ml (i.e., highest concentration that the system 10 is designed to handle), separated by a calculated volume of saline necessary to fill or substantially fill the remaining tube coil volume; and (2) two 1.5 ml "slugs" of a pharmaceutical (for a total volume of 3 ml) at a concentration of 1.67 mCi/ml (i.e., lowest concentration that the system 10 is designed to handle), separated by a calculated volume of saline necessary to fill or substantially fill the remaining tube coil volume.

After the dose is pumped by the system 10 into the tube coil 444 disposed within the ionization chamber 160, the activity level of the dose is measured by the system 10. With reference to FIG. 13, the touch screen arrangement 1100 now includes a display that includes the measured activity level. A new display field 1106a is generated by the system, showing the measured "Calibrated Activity" (here 14.9 mCi) of the prepared dose. Just below field 1106a is a "plus/minus" range indicator 1224. Range indicator 1224, as shown, includes a center circle 1224a, flanked on each side by 10 rectangles. Left and right arrows are also included, respectively, at the far left and far right of indicator 1224. Preferably, as shown in FIG. 13, center circle 1224a highlights when the measured "Calibrated Activity" level is the same as the previously programmed, desired activity level. Otherwise, if the measured activity level is greater or lesser than the desired activity level, corresponding rectangles or, in some cases, arrows will highlight to the right of the center circle 1224a (for measured activity>desired activity) or to the left of the center circle 1224a (for measured activity<desired activity) to visually indicate to the operator the difference between the measured and desired activity levels.

In one embodiment, each of the rectangles represents a default value of a 1% discrepancy in the desired measured activity level, such that three rectangles to the right of the center circle 1224a would be highlighted if the measured activity level was 3% greater than the requested activity level of 15.0 mCi. If the measured activity exceeds the requested activity by more than 10%, then all the rectangles to the right of the center circle 1224a and the right arrow would highlight. The extent of the rectangles in indicator 1224 will convey an acceptable range within which the measured activity may fall. Thus, such an acceptable range could be plus or minus 10% or could be another range as deemed appropriate, with each rectangle representing $\frac{1}{10}$ of the positive or negative extent of that range. Alternately, however, the default value of each rectangular could be pre-set to another value (such as 0.1 mCi) or could be changed by the operator to another value more suitable for the intended application.

In addition to displaying the measured activity level as shown in FIG. 13, the display 1100 also generates a "Discard" button 1222 and an "Infuse" button 1220 in the FDG dose display 1216. If, for example, the measured activity is outside of a clinically acceptable range for the intended procedure, the operator can activate the "Discard" button 1222 to have the system 10 discard the measured dose (i.e., by pumping the dose to the waste receptacle 224, as discussed in detail above) and to prepare another dose for delivery to the patient.

Figure 14:
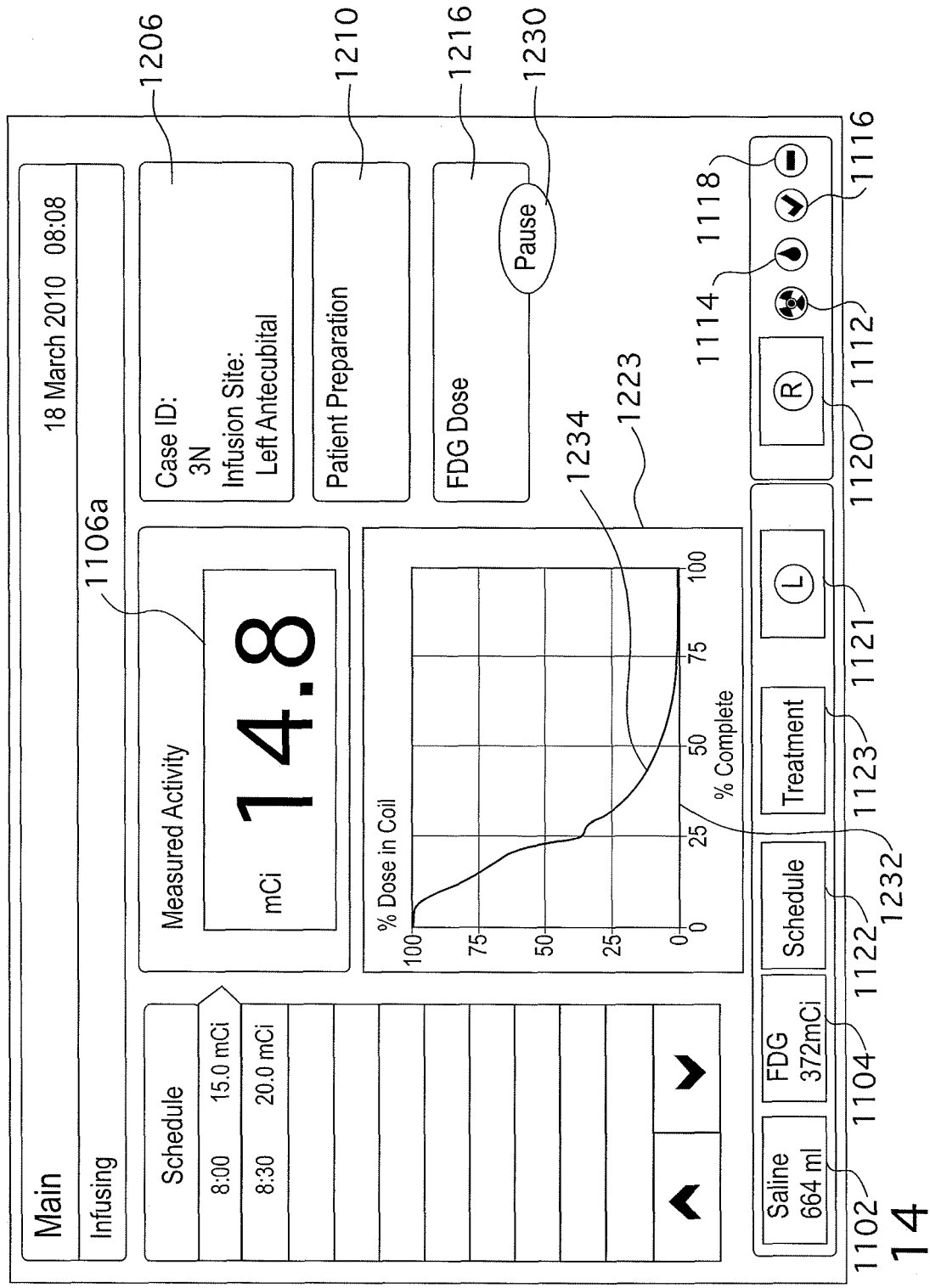

If the operator desires to inject the measured dose and thus activates the "Infuse" button 1220 shown in FIG. 13, the system 10 generates the display shown in FIG. 14 which indicates to the operator that the system 10 is "Infusing" and, via activity monitor 1223, the stage of completion of the injection procedure. Further, the system 10 generates a "Pause" button 1230 in FDG dose display 1216. The operator can activate the "Pause" button 1230 to pause the injection procedure.

The activity monitor 1223 provides a visual display to the operator of the status of the injection procedure and operates in the following manner. First, the radiopharmaceutical activity of the FDG remaining in the tube coil 444 is continuously measured and monitored using the ionization chamber 160 or any other suitable activity detector. These values are continuously sent to the processing unit 1004 of the system controller 5. The processing unit 1004 converts these values to a graphical display that is displayed to the operator such that the operator is provided with an indication of the radiopharmaceutical activity of the FDG remaining in the tube coil 444. As shown in FIG. 14, this graphical display may be an x-y plot 1232 with the X-axis indicating the percent of the infusion that has been completed from 0 to 100 and the Y-axis indicating the percent of the dose that is remaining in the tube coil 444 from 0 to 100. Accordingly, the operator will see a downwardly sloping line 1234 appear as the injection procedure progresses in real-time. Anything other than a downwardly sloping line 1234 will provide an instantaneous indication to an operator that a problem has occurred with the injection procedure.

While activity monitor 1223 has been described hereinabove as including a graphical display in the form of an x-y plot 1232 with the X-axis indicating the percent of the infusion that has been completed from 0 to 100 and the Y-axis indicating the percent of the dose that is remaining in the tube coil 444 from 0 to 100, this is not to be construed as limiting the present disclosure. For instance, various other values can be monitored against the percent of the dose remaining in the tube coil 444 to provide the operator with an indication of the status of the injection procedure such as, but not limited to, time, the percent of saline that has been injected, flow rate of saline or FDG, volume of saline or FDG injected, etc. In addition, the graphical display is not limited to an x-y plot and various other 1-dimensional and 2-dimensional graphical indications of the status of the injection procedure may be provided. For instance, the graphical representation may be a numeric display, a bar graph, or a scatter plot. In addition, the graphical representation may be a graphical display of vial 902 which is shown emptying as the injection procedure occurs.

Figure 15:
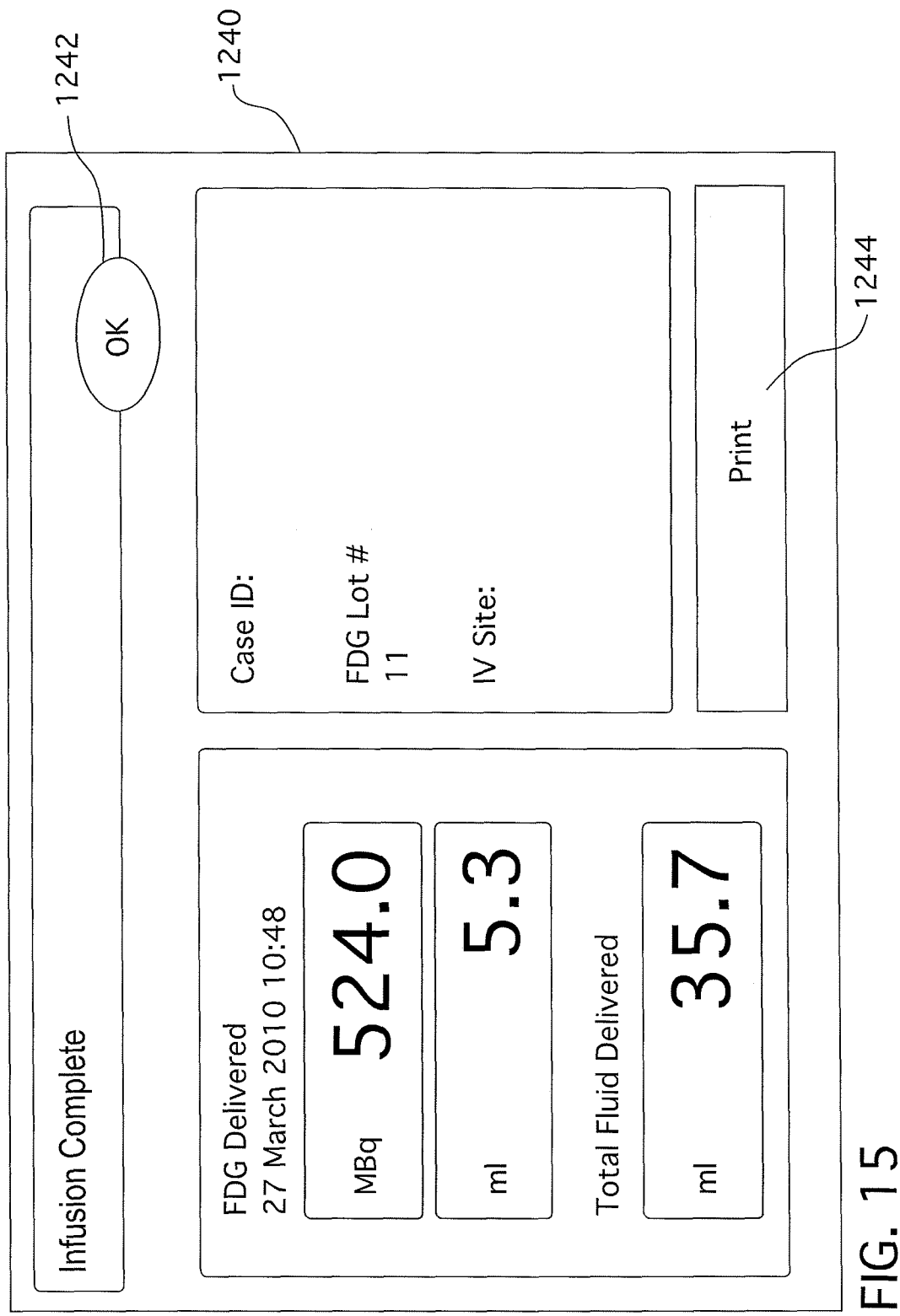
Figure 16:
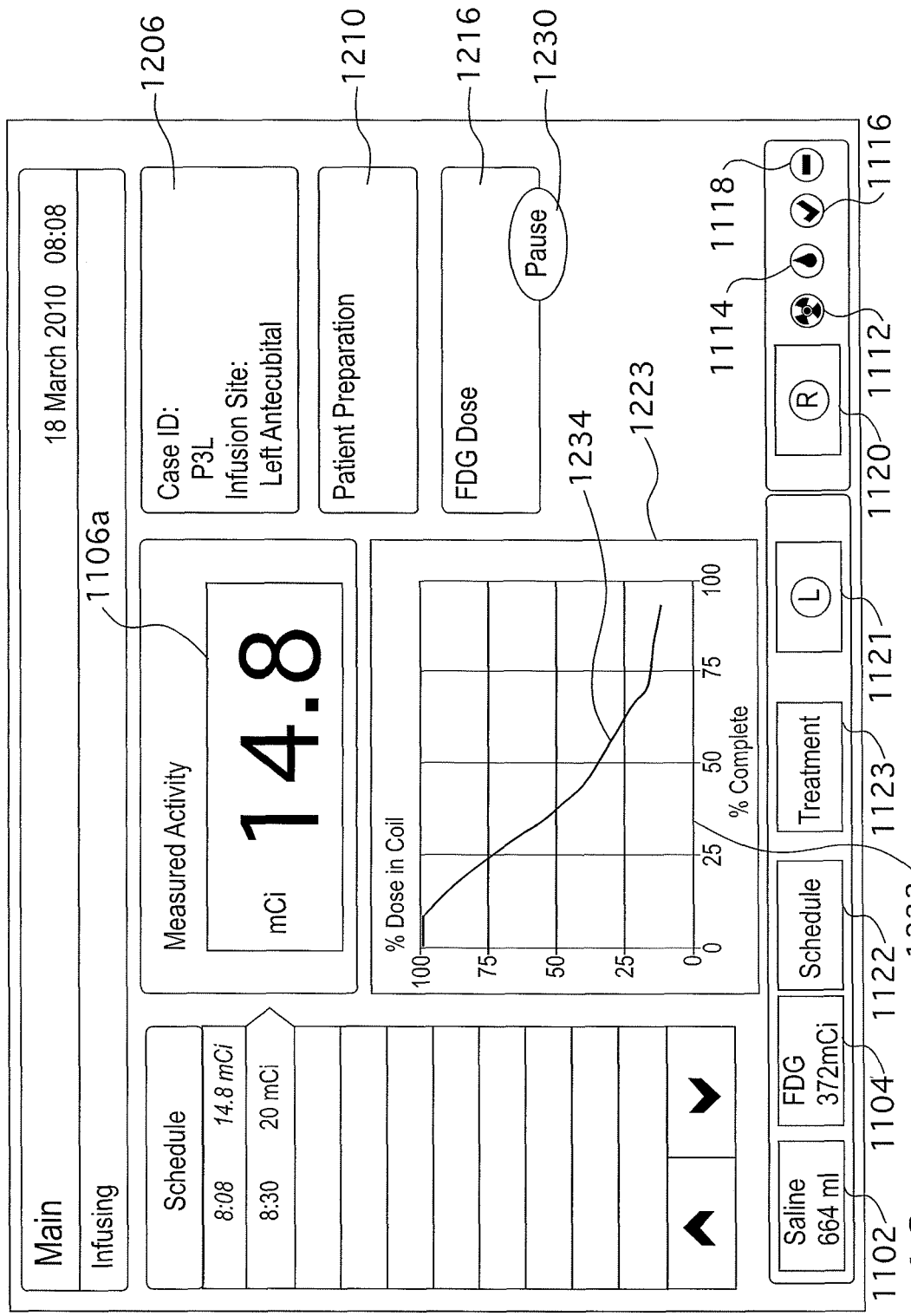

Assuming the injection procedure was completed normally, a pop-up 1240 appears as shown in FIG. 15. This pop-up 1240, as shown, contains information about the activity and volume of the dose (e.g., FDG) just delivered to the patient, the total fluid delivered (which would include saline) and other identifying information including, for example, the patient identification number, radiopharmaceutical lot number, and patient injection site (as shown on the right of pop-up 1240). Activating the "OK" button 1242 causes pop-up 1240 to disappear and the system to revert to a "Ready" state (as shown in FIG. 12), while activating the "Print" button 1244 prompts the injection information to be printed out by the printer 1032 for patient, billing, inventory, or other suitable records.

With reference to FIGS. 16-19, a situation in which activity monitor 1223 provides an indication to an operator that a partial occlusion may have occurred is provided. The operator begins the infusion by activating the "Infuse" button 1220 shown in FIG. 13 such that the system 10 generates the display shown in FIG. 16 which indicates to the operator that the system 10 is "Infusing" and, via activity monitor 1223, the stage of completion of the injection procedure. As the procedure progresses, sloping line 1234 of activity monitor 1223 begins to appear. However, in this instance, sloping line 1234 never reaches the X-axis indicating that the injection procedure has completed. This provides an indication to the operator that a delivery issue may have occurred.

Figure 17:
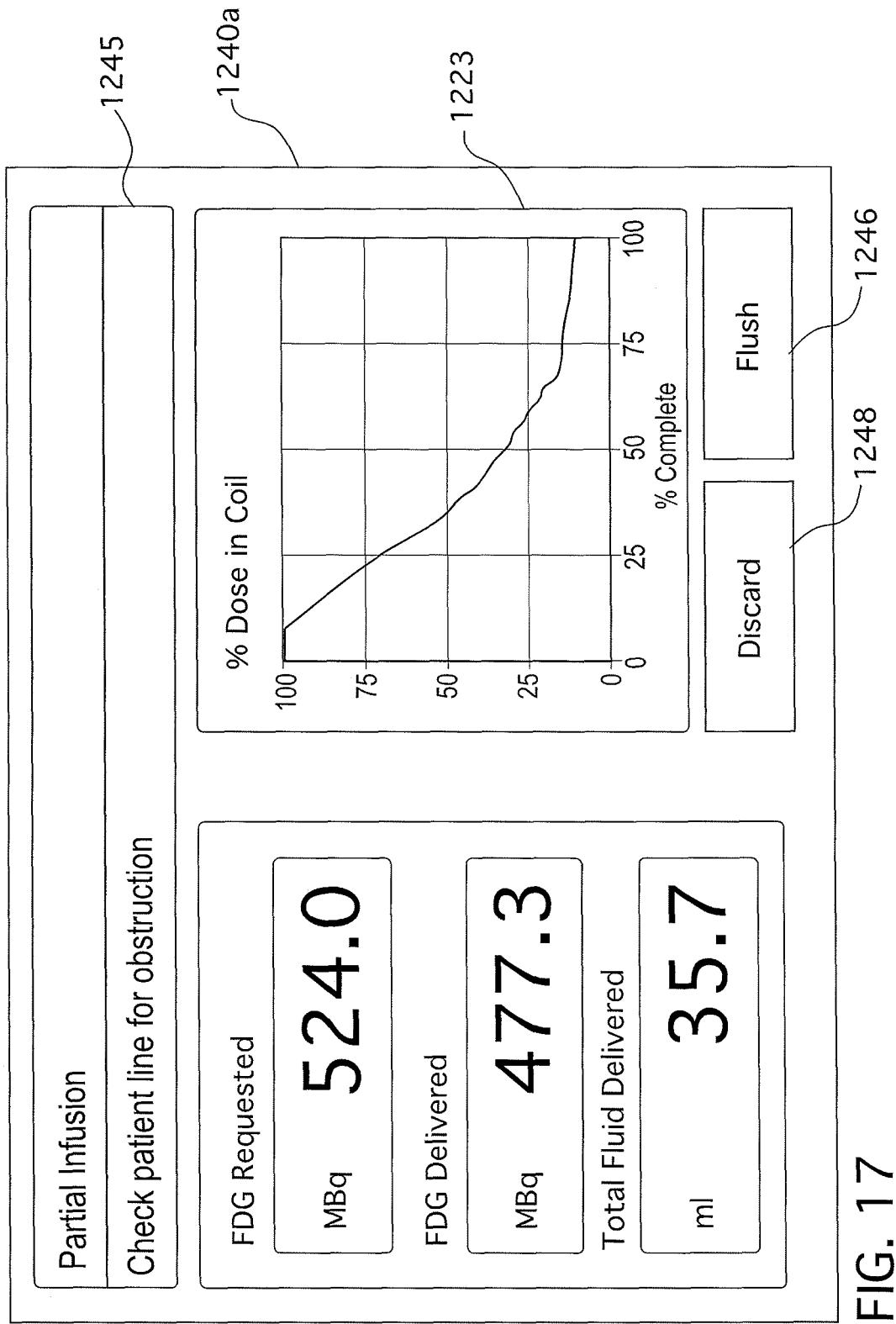

With reference to FIG. 17, a pop-up 1240*a* advising the operator to check the patient line for an obstruction at information line 1245 appears on display screen 15. The operator may also be advised by any other suitable alarm mechanism such as an audible alarm. The pop-up 1240*a* may also contain information about the activity and volume of the dose (e.g., FDG) just delivered to the patient, the total fluid delivered (which would include saline) up to this point, and a close-up of activity monitor 1223 so that the operator can clearly see the progress of the injection procedure. At this point, the operator can check SPDS 700 to determine whether it has been pinched or obstructed in some manner. In addition, the operator can flush the patient line with saline by pressing the "Flush" button 1246. In addition, system controller 5 may also be programmed to automatically flush the patient line with saline if the activity monitor 1223 detects an obstruction. If the operator determines that the obstruction has not been cleared based on information from the activity monitor 1223, the operator can activate the "Discard" button 1248 to have the system 10 discard the measured dose (i.e., by pumping the dose to the waste receptacle 224, as discussed in detail above) and to prepare another dose for delivery to the patient.

Figure 18:
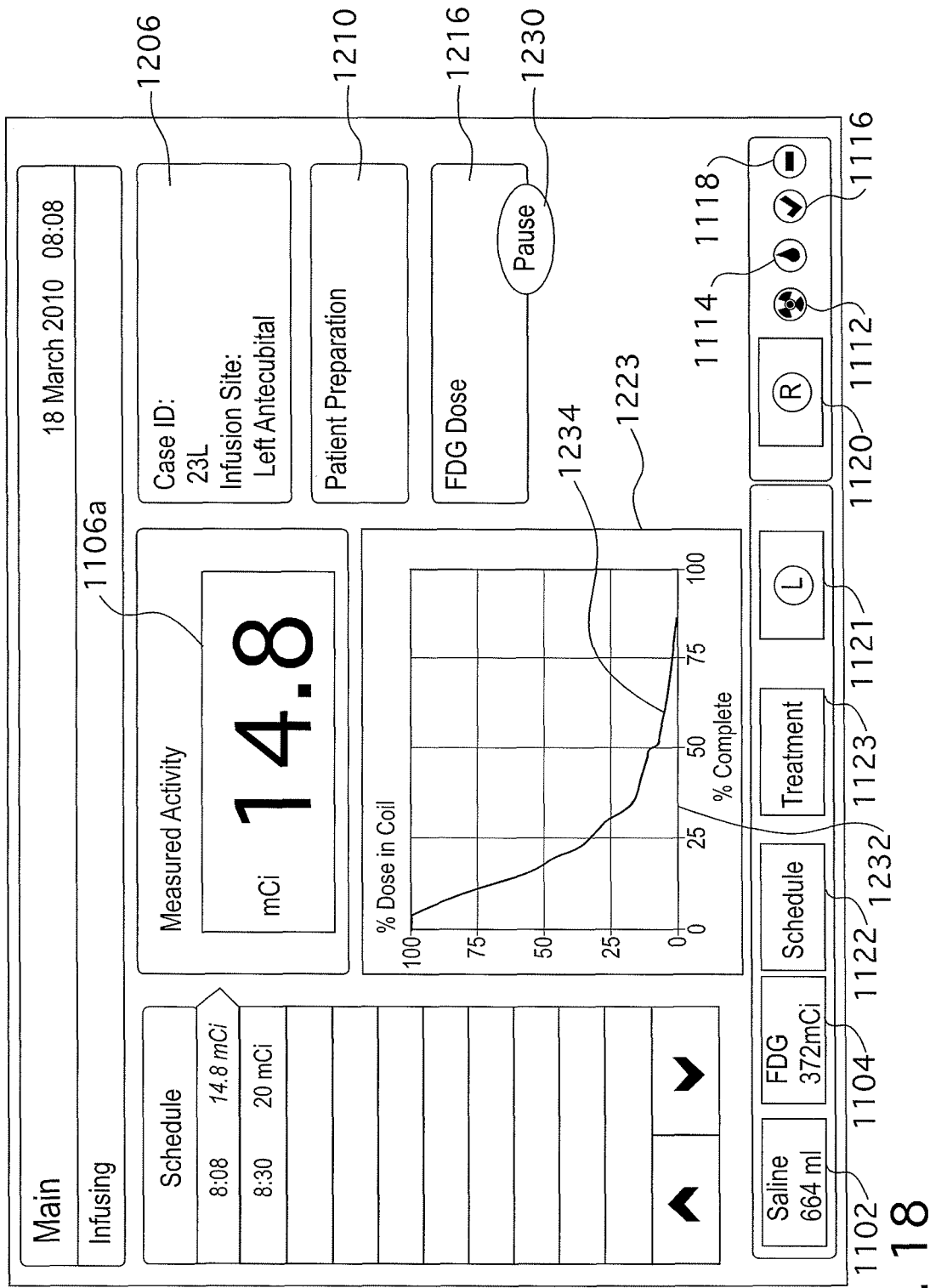
Figure 19:
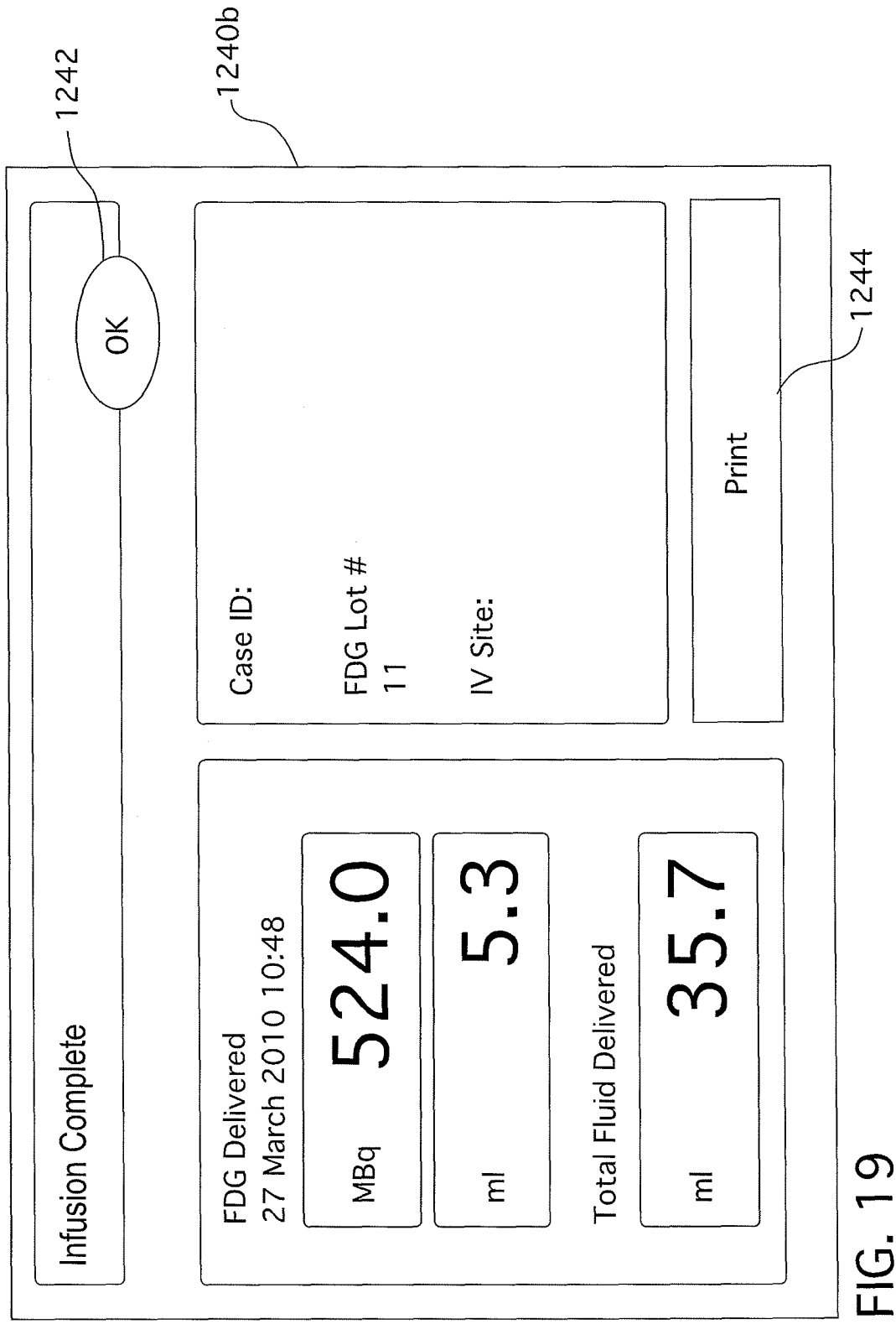

On the other hand, if the system controller 5 determines that the obstruction has been cleared based on information from the activity monitor 1223, system controller 5 will restart the injection procedure and pop-up 1240*a* will disappear from display 15 to leave a screen that looks like the screen in FIG. 18. Assuming the injection procedure was thereafter completed normally, a pop-up 1240*b* appears as shown in FIG. 19. This pop-up 1240*b*, as shown, contains information about the activity and volume of the dose (e.g., FDG) just delivered to the patient, the total fluid delivered (which would include saline), and other identifying information including, for example, the patient identification number, radiopharmaceutical lot number, and patient injection site (as shown on the right of pop-up 1240*b*). Activating the "OK" button 1242 causes pop-up 1240*b* to disappear and the system to revert to a "Ready" state (as shown in FIG. 12), while activating the "Print" button 1244 prompts the injection information to be printed out by the printer 1032 for patient, billing, inventory, or other suitable records.

Finally, with reference to FIGS. 20-23, a situation in which activity monitor 1223 provides an indication to an operator that a complete occlusion or obstruction may have occurred is provided. The operator begins the infusion by activating the "Infuse" button 1220 shown in FIG. 13 such that the system 10 generates the display shown in FIG. 20, which indicates to the operator that the system 10 is "Infusing" and, via activity monitor 1223, the stage of completion of the injection procedure. As the procedure progresses, sloping line 1234 of activity monitor 1223 begins to appear. However, in this instance, sloping line 1234 never even comes close to reaching the X-axis indicating that the injection procedure has completed. This provides an instantaneous indication to the operator that a delivery issue has occurred.

Figure 21:
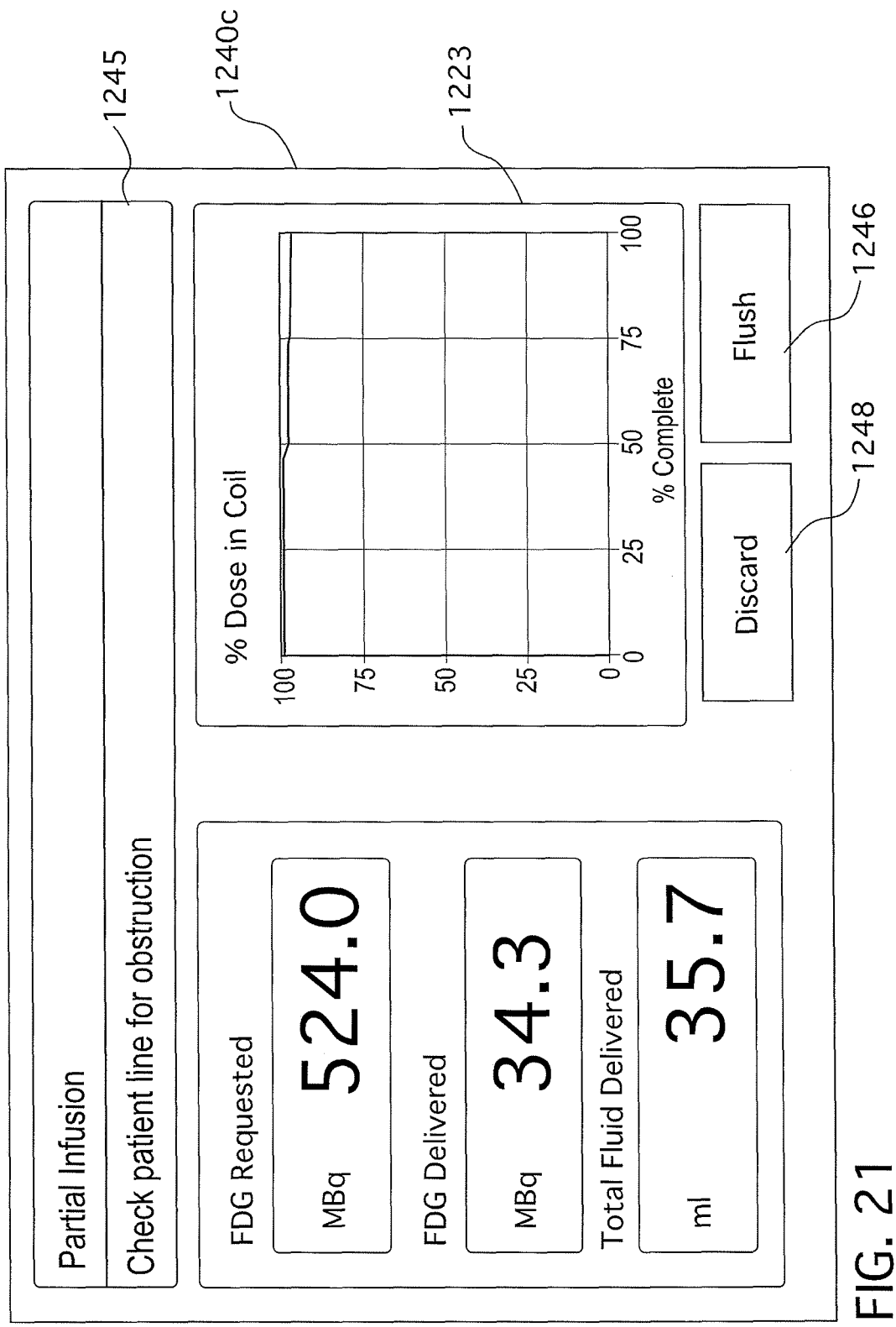

With reference to FIG. 21, a pop-up 1240c advising the operator to check the patient line for an obstruction at information line 1245 appears on display screen 15. The operator may also be advised by any other suitable alarm mechanism such as an audible alarm. The pop-up 1240c may also contain information about the activity and volume of the dose (e.g., FDG) just delivered to the patient, the total fluid delivered (which would include saline) up to this point, and a close-up of activity monitor 1223 so that the operator can clearly see the progress of the injection procedure. At this point, the operator can check SPDS 700 to determine whether it has been pinched or obstructed in some manner. The operator can also flush the patient line with saline by pressing the "Flush" button 1246. In addition, system controller 5 may also be programmed to automatically flush the patient line with saline if the activity monitor 1223 detects an obstruction. If the operator determines that the obstruction has not been cleared based on information from the activity monitor 1223, the operator can activate the "Discard" button 1248 to have the system 10 discard the measured dose (i.e., by pumping the dose to the waste receptacle 224, as discussed in detail above) and to prepare another dose for delivery to the patient.

Figure 20:
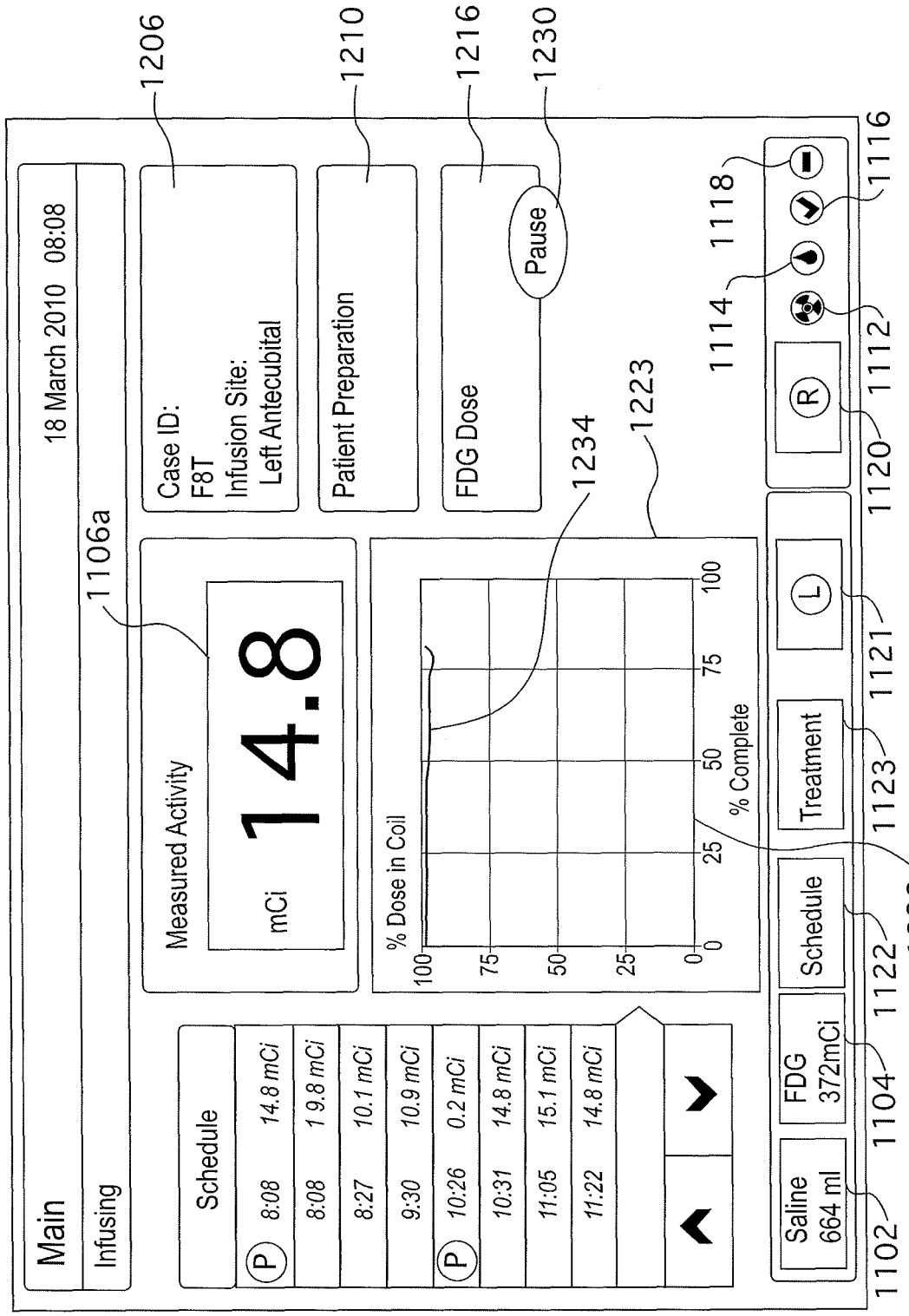
Figure 22:
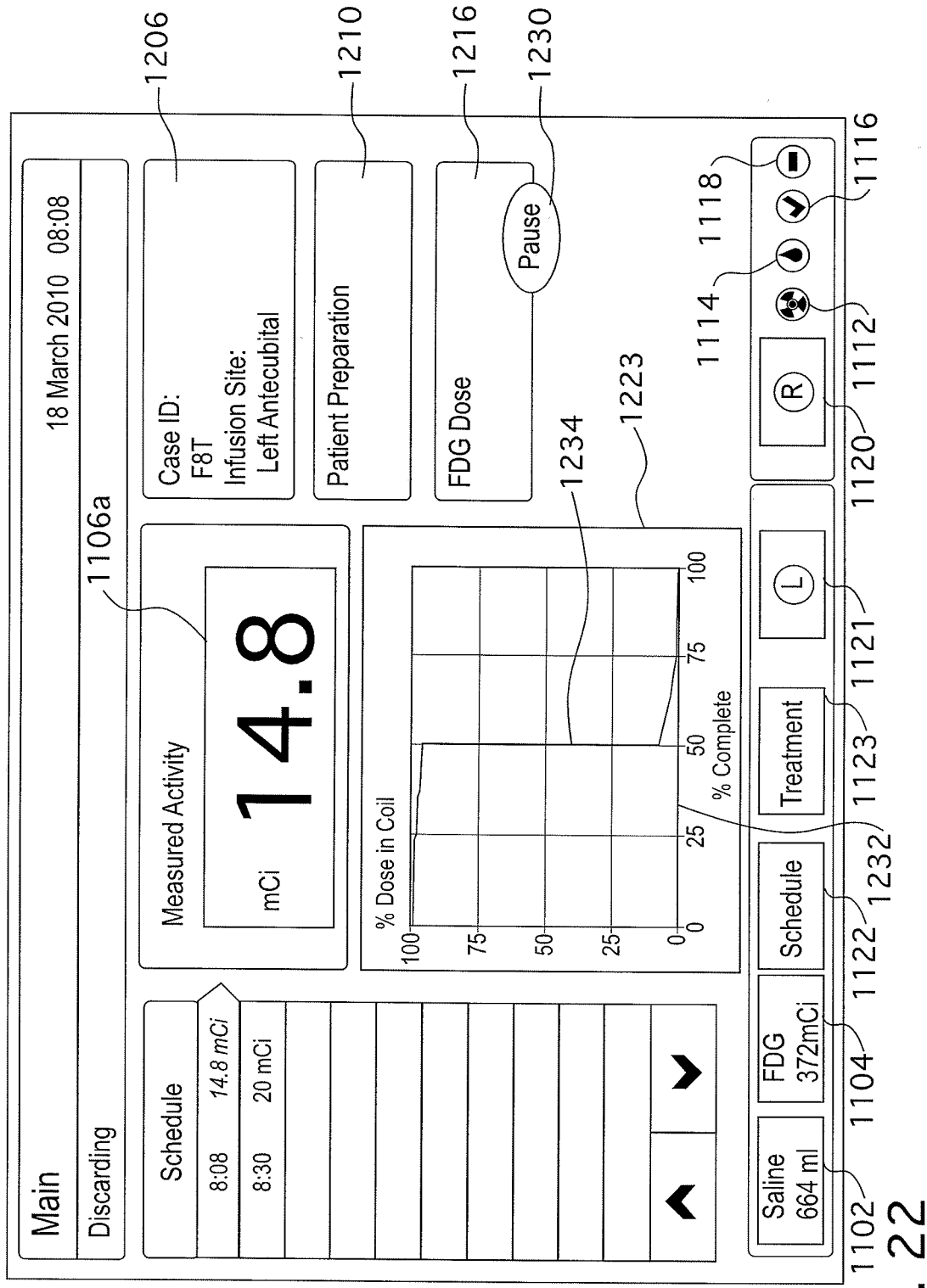

Once the "Discard" button 1248 has been pressed, the pop-up 1240c will disappear from display 15 to leave a screen that looks like the screen in FIG. 22. As can be seen in the activity monitor 1223, the percent dose in tube coil 444 immediately drops to close to zero as the dose is deposited in the waste receptacle 224. Upon completion of the discarding process, a pop-up 1240d appears as shown in FIG. 23. This pop-up 1240d, as shown, contains information about the activity and volume of the dose (e.g., FDG) just delivered to the patient, the total fluid delivered (which would include saline), and other identifying information including, for example, the patient identification number, radiopharmaceutical lot number, and patient injection site (as shown on the right of pop-up 1240d). In addition, information line 1245 lets the operator know that a partial dose has been delivered to the patient. Accordingly, the operator can check the patient line, reinsert the catheter, and take any other precautionary measures before activating the "Retry Patient" button 1250. This button causes pop-up 1240d to disappear and the system to revert to an infusing state as shown in FIG. 20. Activating the "Print" button 1244 prompts the injection information to be printed out by the printer 1032 for patient, billing, inventory, or other suitable records.

Alternatively, the operator may choose to end the injection procedure on the current patient and start a new injection procedure on a new patient by pressing the "Next Patient" button 1252. Upon the pressing of this button, the pop-up 1240d disappears and the system reverts to a "Ready" state as shown in FIG. 12.

Other capabilities and functions not expressly discussed hereinabove or shown in the drawings are of course conceivable in accordance with the embodiments disclosed herein. For instance, if the extraction of a pharmaceutical dose (e.g., FDG) from a vial is interrupted for an unforeseeable reason and is not prompted by a desired "pause", the system could alert the operator to discard the dose (and in that connection present a button for the purpose).

In addition, a flow estimation algorithm can be used to determine the average flow rate of a radiopharmaceutical, based on the average rate of change of activity (slope) of the radiopharmaceutical. An amount of known volume of a radiopharmaceutical is pumped into the ionization chamber 160 and then pumped out of the ionization chamber 160 by pumping in additional fluid, such as saline. The activity of the radiopharmaceutical in the ionization chamber 160 is measured repeatedly during the process and the slope of the radioactive emissions is calculated from the measured activity values. Based on the emissions slope and the volume of the ionization chamber 160, the average rate at which the radiopharmaceutical is being replaced by saline may be calculated and corresponds to the rate at which the fluid is flowing. Because the radiopharmaceutical and chamber materials may be chosen such that radioactive emissions from the radiopharmaceutical penetrate the walls of the ionization chamber 160 before being measured, it is possible to measure the flow rate of the fluid without placing mechanical measuring devices in the fluid stream.

More specifically, the activity monitor can be used to determine: 1) the flow rate of a radiopharmaceutical to a patient; and 2) determine the location of a radiopharmaceutical volume, such as volume 800 or volume 802, within the MPDS 200.

Assumed known items are: 1) $A_c$: Activity in the ionization chamber at the beginning of the infusion. This is measured directly. (MBq); 2) $A_t$: Activity in the tubing at the beginning of the infusion. This value is assumed to be approximately 0 for the first attempt to deliver a dose. Thereafter, it is determined from the following algorithm for resumed dose delivery attempts. (MBq); 3) C: Activity concentration determined from vial assay information (e.g., MBq/ml). 4) T: The total time for the infusion attempt; and 5) $K_t$: Volume of tubing between the ionization chamber 160 and the end of the patient line.

Figure 24A:
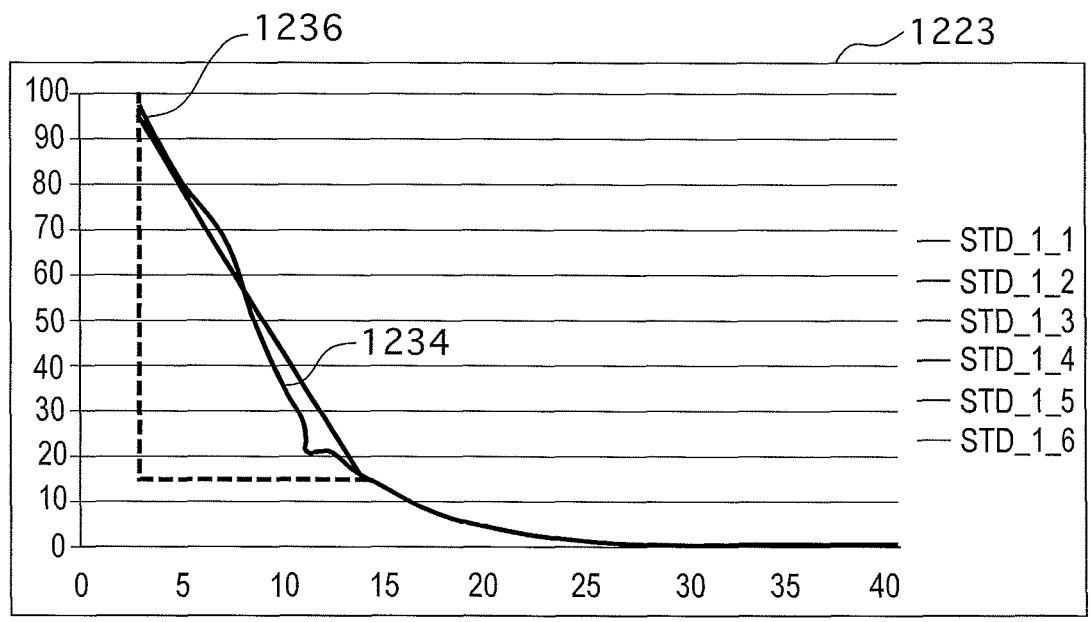
FIGS. 24A-24C are depictions of activity monitors according to an embodiment showing how the monitors can be used to determine flow rate.
Figure 24B:
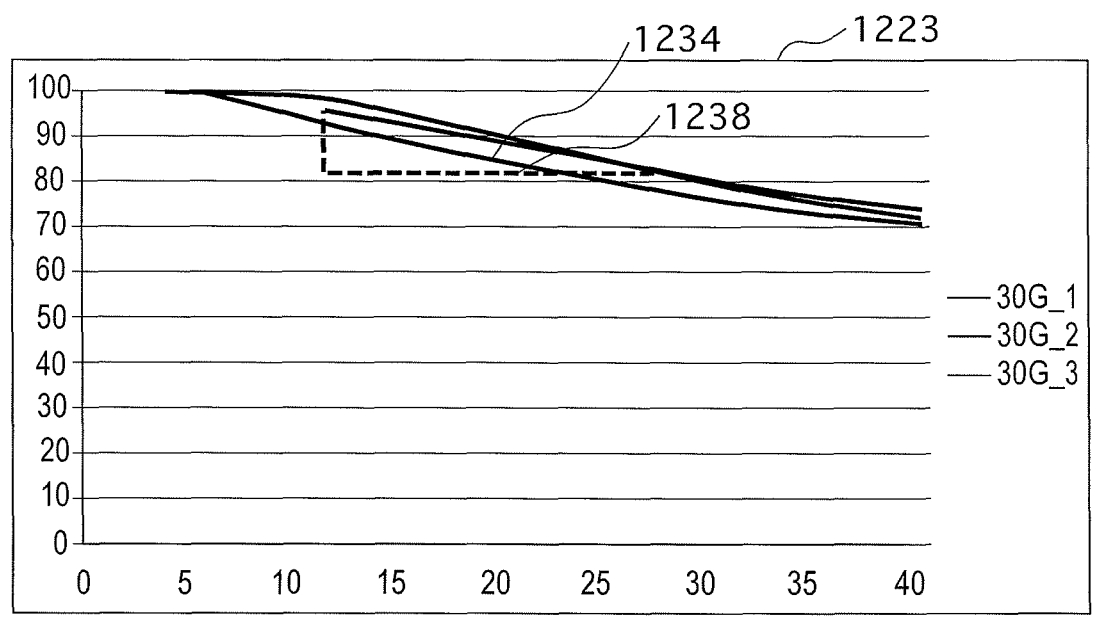
Figure 24C:
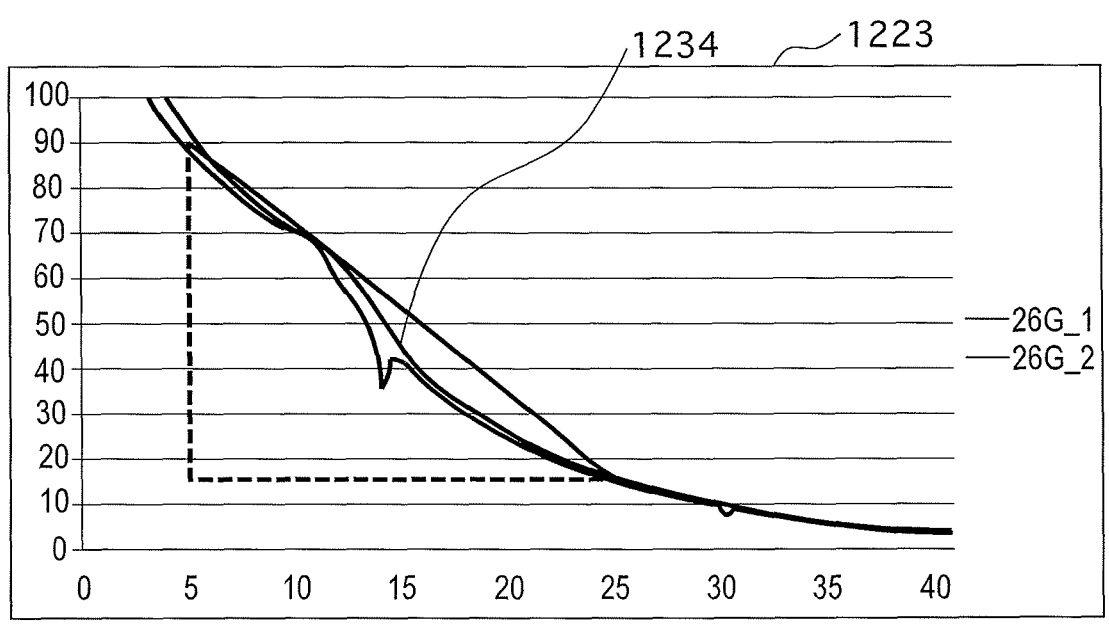

FIGS. 24A-24C illustrate exemplary activity monitors 1223 for instances when an injection procedure has been run to completion, a full occlusion has occurred, and a partial occlusion has occurred, respectively. With reference to FIG. 24A, for example, when volume 800 leaves the ionization chamber 160 it can be modeled linearly from the information provided by the sloping line 1234 in the activity monitor 1223. Linear regression can be utilized on sloping line 1234 as shown in FIG. 24A to find the minimum squared error fit for a line over an appropriate linear range. The appropriate linear range starts with the first sample 1236 representing a 1% decline from $A_c$ and ends with the last sample 1238 that differs from the preceding sample by at least 1% of $A_c$. If such a sample is not detected, then the last sample in the fluid run is used. While the above-described linear range may be used, this is not to be construed as limiting the present disclosure as other linear ranges may be used to achieve the desired results within the scope of this disclosure. The following description is for exemplary purposes only. Then the regression equation is used to determine the flow relationship as follows:

Regression Equation: $A' = A_o + F_a t;$

Slope: $F_a = (N\Sigma At - (\Sigma t)(\Sigma A))/(N\Sigma t^2 - (\Sigma t)^2)$

Intercept: $A_0 = (\Sigma A - F(\Sigma t))/N$

Where, 1) N is the number of measured samples in the region of interest; 2) t is the time associated with each sample, with the first sample in the region of interest being aligned to t=0. The sample rate will likely depend on the load we can handle, but will likely minimally be on the order of 0.25 ms (the rate at which we supply % complete estimates); 3) A is the measured activity at t; and 4) A'=estimated activity from the linear fit. $F_a$ is the activity flow rate (MBq/s). $A_0$ is approximately equal to $A_c$. By determining $F_a/C$, the system can provide the flow rate (ml/s) of the radiopharmaceutical through the MPDS 200 without the need for any expensive flow rate monitors added to the system. $F_a$ is calculated as the injection procedure is performed. Instead of determining the above described activity levels using the ionization chamber 160, these levels may be determined by placing a radiation sensing mechanism, such as a CZT crystal detector, a Geiger-Müller counter, a scintillating counter, or any other suitable sensing device, near the start of the patient line. However, this solution is less desirable than utilizing the ionization chamber because the addition of such a sensing mechanism adds additional cost to the system. In addition, while a linear regression model was discussed hereinabove, this is not to be construed as limiting the present disclosure as other models, such as a logarithmic model, may be utilized to determine the flow rate of the radiopharmaceutical through the MPDS 200.

Once the average flow rate of the radiopharmaceutical through the MPDS 200 is determined, this information can be used to determine the location or distribution of a radiopharmaceutical volume, such as volume 800 or volume 802, within the MPDS 200. Once the average flow rate is determined, this information, along with fluid mechanical properties of the tubing such as diameter and surface treatment, can be used to determine the location of the leading edge and the trailing edge of the radiopharmaceutical volume. Accordingly, by knowing the location of the radiopharmaceutical volumes within the administration set, the system parameters can be adjusted to ensure that the injection procedures are fully complete. In addition, this information may allow the injection system to shape the radiopharmaceutical volume, thereby yielding more accurate images during the imaging procedure.

As discussed in greater detail hereinabove, the present disclosure allows for the use of a discrete radiation monitor, such as ionization chamber 160, to provide a dynamic sensor that provides an operator with the real-time status of an injection procedure, the flow rate of the fluid passing through the administration set, and the location of the radiopharmaceutical volumes within the administration set. Therefore, this system allows an operator to maximize the amount of the requested radiopharmaceutical dose that reaches the patient.

Figure 25:
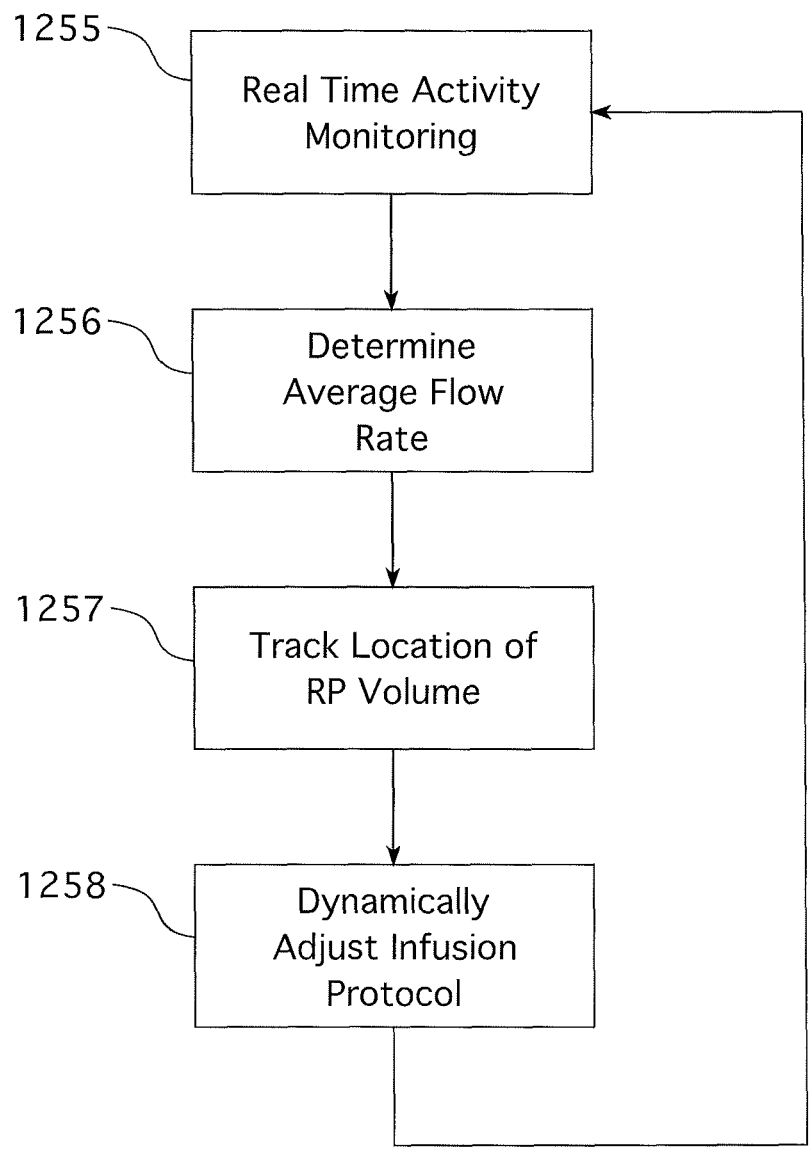
FIG. 25 is a flow diagram illustrating a method according to an embodiment.

With reference to FIG. 25, the system can be briefly summarized as follows. First, at step 1255, the radioactivity of the radiopharmaceutical fluid remaining in at least a portion of a disposable administration set used with a radiopharmaceutical fluid delivery system is measured and monitored to determine a plurality of radiopharmaceutical activity values during the injection procedure. Thereafter, at step 1256, an average flow rate the radiopharmaceutical fluid passing through the disposable administration set is determined. Then, at step 1257, a location of the radiopharmaceutical volume within the disposable administration set is determined based at least in part on the average flow rate of the radiopharmaceutical fluid passing through the disposable administration set. Next, at step 1258, parameters of the injection procedure are automatically adjusted based at least in part on the location of the radiopharmaceutical fluid within the disposable administration set. Thereafter, the injection procedure again monitored and the above-described steps are repeated until the injection procedure is completed.

Although various embodiments have been described in detail for the purpose of illustration, it is to be understood that such detail is solely for that purpose and that the disclosure is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

What is claimed is:

1. A method for monitoring progress of a radiopharmaceutical injection procedure comprising:
    measuring and monitoring a radiopharmaceutical activity of a radiopharmaceutical remaining in a portion of a disposable administration set used with a radiopharmaceutical fluid delivery device, wherein the measuring and monitoring are performed continuously during the radiopharmaceutical injection procedure as the radiopharmaceutical is being injected into a patient;
    displaying the radiopharmaceutical activity of the radiopharmaceutical remaining in the portion of the disposable administration set, wherein the displaying is performed during the radiopharmaceutical injection procedure as the radiopharmaceutical is being injected into the patient;
    detecting whether the radiopharmaceutical activity of the radiopharmaceutical remaining in the portion of the disposable administration set differs from an expected value of radiopharmaceutical activity remaining in the portion of the disposable administration set at a given time during the radiopharmaceutical injection procedure as the radiopharmaceutical is being injected into the patient;
    determining that the radiopharmaceutical activity of the radiopharmaceutical remaining in the portion of the disposable administration set differs from the expected value of radiopharmaceutical activity remaining in the portion of the disposable administration set at the given time; and
    determining that a delivery issue has occurred during the radiopharmaceutical injection procedure as the radiopharmaceutical is being injected into the patient based on the determination that the radiopharmaceutical activity of the radiopharmaceutical remaining in the portion of the disposable administration set differs from the expected value.

2. The method of claim 1, wherein the measuring and monitoring is performed by one of an ionization chamber, a CZT crystal detector, a Geiger-Miller counter, and a scintillating counter.

3. The method of claim 1, wherein displaying the radiopharmaceutical activity comprises:
    displaying a representation of the radiopharmaceutical activity of the radiopharmaceutical remaining in the portion of the disposable administration set on a display device of the radiopharmaceutical fluid delivery device.

4. The method of claim 1, wherein the measured radiopharmaceutical activity of the radiopharmaceutical remaining in the portion of the disposable administration set is the measured radiopharmaceutical activity as a function of at least one of time, flow rate, and volume.

5. The method of claim 1, wherein the disposable administration set comprises:
    a medical fluid component;
    a radiopharmaceutical component;
    a coil component coupled to the medical fluid component and the radiopharmaceutical component and configured to have the radiopharmaceutical activity of the radiopharmaceutical remaining therein measured and monitored; and a waste component coupled to the medical fluid component, the coil component, and the radiopharmaceutical component.

6. The method of claim 1, wherein the delivery issue is an occlusion in the disposable administration set.

7. An article comprising a non-transitory machine-readable storage medium comprising instructions that enable a processor to:

measure and monitor a radiopharmaceutical activity of a radiopharmaceutical remaining in a portion of a disposable administration set used with a radiopharmaceutical fluid delivery system, wherein the measuring and monitoring are performed continuously during a radiopharmaceutical injection procedure as the radiopharmaceutical is being injected into a patient;

display the radiopharmaceutical activity of the radiopharmaceutical remaining in the portion of the disposable administration set, wherein the displaying is performed during the radiopharmaceutical injection procedure as the radiopharmaceutical is being injected into the patient;

detect whether the radiopharmaceutical activity of the radiopharmaceutical remaining in the portion of the disposable administration set differs from an expected value of radiopharmaceutical activity remaining in the portion of the disposable administration set at a given time during the radiopharmaceutical injection procedure as the radiopharmaceutical is being injected into the patient; and determine that a delivery issue has occurred during the radiopharmaceutical injection procedure as the radiopharmaceutical is being injected into the patient based on the detection that the radiopharmaceutical activity of the radiopharmaceutical remaining in the portion of the disposable administration set differs from the expected value of radiopharmaceutical activity remaining in the portion of the disposable administration set at the given time.

8. The article of claim 7, wherein the non-transitory machine readable storage medium further comprises instructions that enable the processor to:

provide an alert that the delivery issue has occurred.

9. The article of claim 7, wherein the delivery issue is an occlusion in the disposable administration set.

10. The article of claim 7, wherein the non-transitory machine readable storage medium further comprises instructions that enable the processor to:

automatically adjust at least one of saline volume and saline flow rate to the disposable administration set to flush the radiopharmaceutical remaining in the portion of the disposable administration set if the delivery issue has occurred.

11. The article of claim 10, wherein the non-transitory machine readable storage medium further comprises instructions that enable the processor to:

end the radiopharmaceutical injection procedure in response to failing to cure the delivery issue by automatically adjusting at least one of saline volume and saline flow rate.

12. A progress monitoring software stored on a non-transitory storage medium to monitor progress of a radiopharmaceutical injection procedure, the software comprising programming instructions that enable a processor to:

measure and monitor a radiopharmaceutical activity of a radiopharmaceutical remaining in a portion of a disposable administration set used with a radiopharmaceutical fluid delivery system, wherein the measuring and monitoring are performed continuously during the radiopharmaceutical injection procedure as the radiopharmaceutical is being injected into the patient;

display the radiopharmaceutical activity of the radiopharmaceutical remaining in the portion of the disposable administration set, wherein the displaying is performed during the radiopharmaceutical injection procedure as the radiopharmaceutical is being injected into a patient;

detect whether the radiopharmaceutical activity of the radiopharmaceutical remaining in the portion of the disposable administration set differs from an expected value of radiopharmaceutical activity remaining in the portion of the disposable administration set at a given time during the radiopharmaceutical injection procedure as the radiopharmaceutical is being injected into the patient; and determine that a delivery issue has occurred during the radiopharmaceutical injection procedure as the radiopharmaceutical is being injected into the patient based on the detection that the radiopharmaceutical activity of the radiopharmaceutical remaining in the portion of the disposable administration set differs from the expected value of radiopharmaceutical activity remaining in the portion of the disposable administration set at the given time.

13. The progress monitoring software of claim 12, wherein the software further comprises programming instructions that enable the processor to:

automatically adjust at least one of saline volume and saline flow rate to the disposable administration set to flush the radiopharmaceutical remaining in the portion of the disposable administration set if the delivery issue has occurred; and end the radiopharmaceutical injection procedure in response to failing to cure the delivery issue by automatically adjusting at least one of saline volume and saline flow rate.

14. The progress monitoring software of claim 12, wherein the delivery issue is an occlusion in the disposable administration set.

15. A radiopharmaceutical fluid delivery device for performing a radiopharmaceutical injection procedure, the radiopharmaceutical fluid delivery device comprising:

a disposable administration set operable to allow fluid flow from a radiopharmaceutical source associated with the radiopharmaceutical fluid delivery device to a patient;

an activity measuring unit operable to continuously determine a level of radioactivity of a radiopharmaceutical fluid within a portion of the disposable administration set during the radiopharmaceutical injection procedure as the radiopharmaceutical fluid flows to the patient;

a control unit operatively coupled to the activity measuring unit operable to convert activity measurements taken by the activity measuring unit to a representation of a radiopharmaceutical activity remaining in the portion of the disposable administration set during the radiopharmaceutical injection procedure as the radiopharmaceutical fluid flows to the patient; and a display unit operatively coupled to the control unit operable to display the radiopharmaceutical activity remaining in the portion of the disposable administration set during the radiopharmaceutical injection procedure as the radiopharmaceutical fluid flows to the patient, wherein the control unit is configured to detect whether the radiopharmaceutical activity remaining in the portion of the disposable administration set differs from an expected value of radiopharmaceutical activity remaining in the portion of the disposable administration set at a given time during the radiopharmaceutical injection procedure as the radiopharmaceutical fluid flows to the patient and determine that a delivery issue has occurred during the radiopharmaceutical injection procedure as the radiopharmaceutical fluid flows to the patient based on the detection that radiopharmaceutical activity remaining in the portion of the disposable administration set differs from the expected value of radiopharmaceutical activity remaining in the portion of the disposable administration set at the given time.

16. The radiopharmaceutical fluid delivery device of claim 15, wherein the control unit is further configured to provide an alert that the delivery issue has occurred and adjust at least one of saline volume and saline flow rate to the disposable administration set to flush the radiopharmaceutical remaining in the portion of the disposable administration set if the delivery issue has occurred.

17. The radiopharmaceutical fluid delivery device of claim 16, wherein the control unit is further configured to end the radiopharmaceutical injection procedure in response to failing to cure the delivery issue by adjusting at least one of saline volume and saline flow rate.

18. The radiopharmaceutical fluid delivery device of claim 15, wherein the control unit is further configured to cause the display unit to display a representation of the radiopharmaceutical activity remaining in the portion of the disposable administration set.

19. The radiopharmaceutical fluid delivery device of claim 18, wherein the representation of the radiopharmaceutical activity remaining in the portion of the disposable administration set is at least one of a numeric display, a bar graph, an x-y plot, and a scatter plot.

20. The radiopharmaceutical fluid delivery device of claim 15, wherein the disposable administration set comprises:
   a medical fluid component;
   a radiopharmaceutical component;
   a coil component coupled to the medical fluid component and the radiopharmaceutical component; and
   a waste component coupled to the medical fluid component, the coil component, and the radiopharmaceutical component.

21. The radiopharmaceutical fluid delivery device of claim 20, wherein the coil component is the portion of the disposable administration set for which the activity measuring unit is operable to determine the level of radioactivity.

22. The radiopharmaceutical fluid delivery device of claim 15, wherein the delivery issue is an occlusion in the disposable administration set.

* * * * *

UNITED STATES PATENT AND TRADEMARK OFFICE
CERTIFICATE OF CORRECTION

| | | |
|---|---|---|
| PATENT NO. | : 9,242,119 B2 | Page 1 of 1 |
| APPLICATION NO. | : 13/700299 | |
| DATED | : January 26, 2016 | |
| INVENTOR(S) | : Agamaite et al. | |

It is certified that error appears in the above-identified patent and that said Letters Patent is hereby corrected as shown below:

IN THE DRAWINGS:
In Fig. 11, Sheet 18 of 33, delete "(M3)" and insert -- M3 --, therefor.

IN THE SPECIFICATION:
In Column 3, Lines 66-67, delete "diluent dilutent" and insert -- diluent --, therefor.
In Column 7, Line 7, delete "multipatient" and insert -- multi-patient --, therefor.
In Column 14, Line 14, delete "FIG. 1A-1E," and insert -- FIGS. 1A-1E, --, therefor.
In Column 30, Line 36, delete "Kt;" and insert -- Kt: --, therefor.

IN THE CLAIMS:
In Column 32, Line 49, in Claim 2, delete "Geiger-Miller" and insert -- Geiger-Müller --, therefor.

Signed and Sealed this
Twenty-sixth Day of April, 2016

Michelle K. Lee
*Director of the United States Patent and Trademark Office*